(12) United States Patent
Seo

(10) Patent No.: US 12,120,900 B2
(45) Date of Patent: Oct. 15, 2024

(54) LIGHT-EMITTING DEVICE, LIGHT-EMITTING APPARATUS, ELECTRONIC DEVICE, AND LIGHTING DEVICE

(71) Applicant: Semiconductor Energy Laboratory Co., Ltd., Kanagawa-ken (JP)

(72) Inventor: Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 698 days.

(21) Appl. No.: 17/274,514

(22) PCT Filed: Aug. 27, 2019

(86) PCT No.: PCT/IB2019/057171
§ 371 (c)(1),
(2) Date: Mar. 9, 2021

(87) PCT Pub. No.: WO2020/053689
PCT Pub. Date: Mar. 19, 2020

(65) Prior Publication Data
US 2021/0343965 A1    Nov. 4, 2021

(30) Foreign Application Priority Data
Sep. 14, 2018  (JP) ................. 2018-172929

(51) Int. Cl.
*H01L 51/50* (2006.01)
*H10K 50/11* (2023.01)
(Continued)

(52) U.S. Cl.
CPC .......... *H10K 50/11* (2023.02); *H10K 85/342* (2023.02); *H10K 85/615* (2023.02);
(Continued)

(58) Field of Classification Search
None
See application file for complete search history.

(56) References Cited

U.S. PATENT DOCUMENTS

| | | |
|---|---|---|
| 7,906,226 B2 | 3/2011 | Matsuura et al. |
| 8,105,701 B2 | 1/2012 | Matsuura et al. |
| (Continued) | | |

FOREIGN PATENT DOCUMENTS

| | | |
|---|---|---|
| CN | 107108585 A | 8/2017 |
| CN | 108140740 A | 6/2018 |
| (Continued) | | |

OTHER PUBLICATIONS

Tanaka.D et al., "Ultra High Efficiency Green Organic Light-Emitting Devices", Jpn. J. Appl. Phys. (Japanese Journal of Applied Physics), Dec. 22, 2006, vol. 46, No. 1, pp. L10-L12, The Japan Society of Applied Physics.

(Continued)

*Primary Examiner* — Gregory D Clark
(74) *Attorney, Agent, or Firm* — Husch Blackwell LLP

(57) ABSTRACT

To provide a light-emitting device not only including a light-emitting layer in which energy is efficiently transferred from a host material to a guest material but also having high reliability. The light-emitting device not only includes a light-emitting layer in which the T1 levels and the S1 levels of a host material and a guest material fall within certain ranges so that energy can be efficiently transferred from the host material to the guest material and but also has improved reliability.

21 Claims, 48 Drawing Sheets

(51) Int. Cl.
*H10K 85/30* (2023.01)
*H10K 85/60* (2023.01)
*H10K 101/10* (2023.01)
*H10K 101/30* (2023.01)
*H10K 101/40* (2023.01)

(52) U.S. Cl.
CPC ......... *H10K 85/636* (2023.02); *H10K 85/654* (2023.02); *H10K 85/657* (2023.02); *H10K 85/6572* (2023.02); *H10K 85/6576* (2023.02); *H10K 2101/10* (2023.02); *H10K 2101/30* (2023.02); *H10K 2101/40* (2023.02)

(56) References Cited

U.S. PATENT DOCUMENTS

| | | | |
|---|---|---|---|
| 8,470,455 | B2 | 6/2013 | Matsuura et al. |
| 10,096,658 | B2 | 10/2018 | Watabe et al. |
| 10,177,329 | B2 | 1/2019 | Kim et al. |
| 10,529,939 | B2 | 1/2020 | Kim |
| 10,693,094 | B2 | 6/2020 | Seo et al. |
| 10,916,707 | B2 | 2/2021 | Kawakami et al. |
| 11,152,583 | B2 | 10/2021 | Kim et al. |
| 2014/0084274 | A1* | 3/2014 | Yamazaki ............... H10K 50/11 257/40 |
| 2015/0069352 | A1 | 3/2015 | Kim et al. |
| 2017/0062752 | A1 | 3/2017 | Ihn et al. |
| 2017/0271610 | A1 | 9/2017 | Takahashi |
| 2019/0027542 | A1 | 1/2019 | Watabe et al. |
| 2019/0031673 | A1 | 1/2019 | Yamaguchi et al. |
| 2020/0083462 | A1 | 3/2020 | Kurihara et al. |
| 2020/0199135 | A1 | 6/2020 | Kurihara et al. |
| 2020/0350508 | A1 | 11/2020 | Seo et al. |
| 2021/0159410 | A1 | 5/2021 | Kawakami et al. |
| 2021/0408421 | A1 | 12/2021 | Kim et al. |
| 2023/0269954 | A1 | 8/2023 | Seo et al. |

FOREIGN PATENT DOCUMENTS

| | | |
|---|---|---|
| CN | 109305971 A | 2/2019 |
| CN | 109651384 A | 4/2019 |
| DE | 10 2018 212 379 A1 | 1/2019 |
| JP | 2010-182699 A | 8/2010 |
| JP | 2014-078699 A | 5/2014 |
| JP | 2016-092194 A | 5/2016 |
| JP | 2018-154622 A | 10/2018 |
| JP | 2019-006763 A | 1/2019 |
| JP | 2019-085393 A | 6/2019 |
| JP | 2019-085418 A | 6/2019 |
| KR | 2013-0115027 A | 10/2013 |
| KR | 2014-0038886 A | 3/2014 |
| KR | 2016-0080090 A | 7/2016 |
| KR | 2017-0026075 A | 3/2017 |
| KR | 10-2017-0078573 * 6/2017 ............. C09K 11/06 |
| KR | 2017-0078573 A | 7/2017 |
| KR | 2018-0038834 A | 4/2018 |
| KR | 2019-0013567 A | 2/2019 |
| TW | 201824599 | 7/2018 |
| TW | 201831439 | 9/2018 |
| TW | 201839095 | 11/2018 |
| TW | 201906846 | 2/2019 |
| TW | 201910337 | 3/2019 |
| WO | WO 2013/154342 A1 | 10/2013 |
| WO | WO 2016/108596 A2 | 7/2016 |
| WO | WO 2017/055963 A1 | 4/2017 |
| WO | WO 2018/167606 A1 | 9/2018 |
| WO | WO 2018/234926 A1 | 12/2018 |

OTHER PUBLICATIONS

Sun.J et al., "A Fluorescent Organic Light-Emitting Diode with 30% External Quantum Efficiency", Adv. Mater. (Advanced Materials), May 30, 2014, vol. 26, No. 32, pp. 5684-5688.

Shin.H et al., "Blue Phosphorescent Organic Light-Emitting Diodes Using an Exciplex Forming Co-Host With the External Quantum Efficiency of Theoretical Limit", Adv. Mater. (Advanced Materials), May 19, 2014, vol. 26, No. 27, pp. 4730-4734.

Tsuboi. T et al., "Photoluminescence characteristics of blue phosphorescent Ir3+-compounds FIrpic and FIrN4 doped in mCP and SimCP", Optical Materials, Oct. 1, 2008, vol. 31, No. 2, pp. 366-371.

Kondakova.M et al., "High-efficiency, low-voltage phosphorescent organic light-emitting diode devices with mixed host", J. Appl. Phys. (Journal of Applied Physics) , Nov. 4, 2008, vol. 104, pp. 094501-1-094501-17.

Tsuboyama.A et al., "Homoleptic Cyclometalated Iridium Complexes with Highly Efficient Red Phosphorescence and Application to Organic Light-Emitting Diode", J. Am. Chem. Soc. (Journal of the American Chemical Society), 2003, vol. 125, No. 42, pp. 12971-12979.

Chinese Office Action (Application No. 201980060079.8) Dated Oct. 21, 2023.

Taiwanese Office Action (Application No. 108131461) Dated Mar. 24, 2023.

International Search Report (Application No. PCT/IB2019/057171) Dated Nov. 5, 2019.

Written Opinion (Application No. PCT/IB2019/057171) Dated Nov. 5, 2019.

* cited by examiner

LIGHT-EMITTING DEVICE, LIGHT-EMITTING APPARATUS, ELECTRONIC DEVICE, AND LIGHTING DEVICE

This application is a 371 of international application PCT/IB2019/057171 filed on Aug. 27, 2019 which is incorporated herein by reference.

TECHNICAL FIELD

One embodiment of the present invention relates to a light-emitting device, a light-emitting apparatus, an electronic device, and a lighting device. Note that one embodiment of the present invention is not limited thereto. That is, one embodiment of the present invention relates to an object, a method, a manufacturing method, or a driving method. One embodiment of the present invention relates to a process, a machine, manufacture, or a composition of matter.

BACKGROUND ART

A light-emitting device including an EL layer between a pair of electrodes (also referred to as an organic EL device) has characteristics such as thinness, light weight, high-speed response to input signals, and low power consumption; thus, a display including such a light-emitting device has attracted attention as a next-generation flat panel display.

In a light-emitting device, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting device is considered to be S*:T*=1:3. Since the spectrum of light emitted from a light-emitting substance depends on the light-emitting substance, the use of different types of organic compounds as light-emitting substances makes it possible to obtain light-emitting devices which exhibit various colors.

In order to improve the device characteristics and reliability of such a light-emitting device, improvement of a device structure, development of a material, and the like have been actively carried out (see Patent Document 1, for example).

REFERENCE

[Patent Document 1] Japanese Published Patent Application No. 2010-182699

DISCLOSURE OF INVENTION

To improve the device characteristics and reliability of a light-emitting device, it is important to reduce damage due to driving of the device while considering the mechanism of energy transfer between a host material and a guest material in a light-emitting layer of the light-emitting device.

In view of the above, one embodiment of the present invention provides a light-emitting device not only including a light-emitting layer in which energy is efficiently transferred from a host material to a guest material but also having high reliability.

Note that the descriptions of these objects do not disturb the existence of other objects. One embodiment of the present invention does not have to achieve all the objects. Other objects will be apparent from and can be derived from the descriptions of the specification, the drawings, the claims, and the like.

One embodiment of the present invention is a light-emitting device not only including a light-emitting layer in which the T1 levels and the S1 levels of a host material and a guest material fall within certain ranges so that energy can be efficiently transferred from the host material to the guest material and but also having improved reliability.

One embodiment of the present invention is a light-emitting device which includes an EL layer between a pair of electrodes and in which the EL layer includes a light-emitting layer, the light-emitting layer contains a first organic compound, a second organic compound, and a light-emitting substance, a T1 level ($T_{D(edge)}$) of the light-emitting substance and the lower ($T_{H(edge)}$) of a T1 level of the first organic compound and a T1 level of the second organic compound satisfy Formula (1) below, and a difference between an S1 level ($S'_{H(edge)}$) of a mixed material of the first organic compound and the second organic compound and $T_{H(edge)}$ satisfies Formula (2) below.

[Formula 1]

$$0.07 \text{ eV} \leq T_{H(edge)} - T_{D(edge)} \leq 0.27 \text{ eV} \quad (1)$$

Note that $T_{H(edge)}$ represents the lower of the T1 levels derived from emission edges on a short wavelength side of phosphorescent spectra of the first organic compound and the second organic compound. $T_{D(edge)}$ represents the T1 level derived from an absorption edge of an absorption spectrum of the light-emitting substance. $S'_{H(edge)}$ represents the S1 level derived from an emission edge on a short wavelength side of a fluorescent spectrum of the mixed material of the first organic compound and the second organic compound.

[Formula 2]

$$0.2 \text{ eV} \leq S'_{H(edge)} - T_{H(edge)} \leq 0.5 \text{ eV} \quad (2)$$

Another embodiment of the present invention is a light-emitting device which includes an EL layer between a pair of electrodes and in which the EL layer includes a light-emitting layer, the light-emitting layer contains a first organic compound, a second organic compound, and a light-emitting substance, a T1 level ($T_{D(edge)}$) of the light-emitting substance and the lower ($T_{H(edge)}$) of a T1 level of the first organic compound and a T1 level of the second organic compound satisfy Formula (3) below, and a difference between an S1 level ($S'_{H(edge)}$) of a mixed material of the first organic compound and the second organic compound and $T_{H(edge)}$ satisfies Formula (4) below.

[Formula 3]

$$0.07 \text{ eV} \leq T_{H(edge)} - T_{D(edge)} \leq 0.17 \text{ eV} \quad (3)$$

Note that $T_{H(edge)}$ represents the lower of the T1 levels derived from emission edges on a short wavelength side of phosphorescent spectra of the first organic compound and the second organic compound. $T_{D(edge)}$ represents the T1 level derived from an absorption edge of an absorption spectrum of the light-emitting substance. $S'_{H(edge)}$ represents the S1 level derived from an emission edge on a short wavelength side of a fluorescent spectrum of the mixed material of the first organic compound and the second organic compound.

[Formula 4]

$$0.2 \text{ eV} \leq S'_{H(edge)} - T_{H(edge)} \leq 0.5 \text{ eV} \quad (4)$$

In each of the above structures, the first organic compound and the second organic compound form an exciplex in combination. The S1 level ($S'_{H(edge)}$) is derived from an emission edge on a short wavelength side of a fluorescent spectrum of the exciplex.

In each of the above structures, the first organic compound is preferably a π-electron deficient heteroaromatic compound. The first organic compound preferably has a pyridine ring structure, a diazine ring structure, or a triazine ring structure. It is particularly preferred that the first organic compound have a structure where an aromatic ring is fused to a furan ring of a furodiazine skeleton.

One embodiment of the present invention includes a light-emitting device having any of the above structures in which the light-emitting substance is a phosphorescent substance. One embodiment of the present invention also includes a light-emitting device having any of the above structures in which the second organic compound is a carbazole derivative, preferably a bicarbazole derivative. As the second organic compound, a 3,3'-bicarbazole derivative is particularly preferred. Note that it is preferred that these carbazole derivatives not have an aromatic amine skeleton (specifically, a triarylamine skeleton).

One embodiment of the present invention includes, in its category, in addition to a light-emitting apparatus including the light-emitting device described above, an electronic device including a light-emitting device or a light-emitting apparatus (specifically, an electronic device including a light-emitting device or a light-emitting apparatus and a connection terminal or an operation key) and a lighting device including a light-emitting device or a light-emitting apparatus (specifically, a lighting device including a light-emitting device or a light-emitting device and a housing). Accordingly, the light-emitting device in this specification refers to an image display device or a light source (including a lighting device). In addition, a light-emitting apparatus includes, in its category, a module in which a light-emitting apparatus is connected to a connector such as a flexible printed circuit (FPC) or a tape carrier package (TCP), a module in which a printed wiring board is provided on the tip of a TCP, and a module in which an integrated circuit (IC) is directly mounted on a light-emitting device by a chip on glass (COG) method.

One embodiment of the present invention can provide a novel light-emitting device having improved reliability as well as including a light-emitting layer in which energy is efficiently transferred from a host material to a guest material.

Note that the descriptions of the effects do not disturb the existence of other effects. One embodiment of the present invention does not need to have all the effects listed above. Other effects will be apparent from and can be derived from the descriptions of the specification, the drawings, the claims, and the like. A novel light-emitting device with improved reliability can be provided.

BEST MODE FOR CARRYING OUT THE INVENTION

Figure 1:
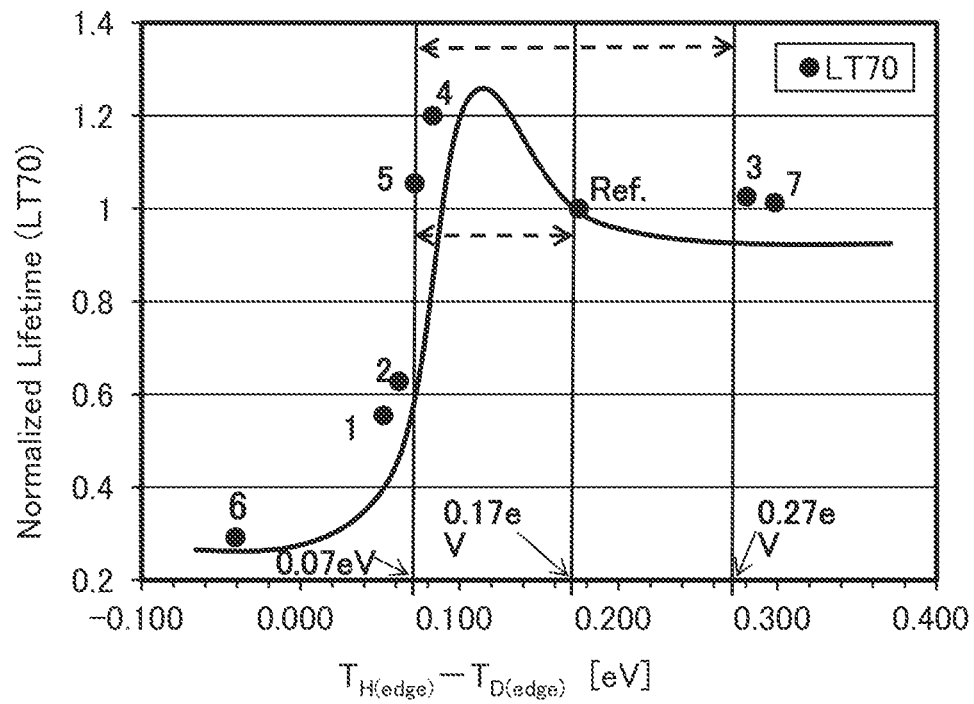
FIG. 1 is a graph showing the relation between $T_{H(edge)} - T_{D(edge)}$ and normalized lifetime.

Embodiments and examples of the present invention will be described in detail below with reference to the drawings. Note that the present invention is not limited to the following description, and the modes and details of the present invention can be modified in various ways without departing from the spirit and scope of the present invention. Therefore, the present invention should not be construed as being limited to the description in the following embodiments and examples.

Note that the position, size, range, or the like of each component illustrated in drawings and the like is not accurately represented in some cases for easy understanding.

Therefore, the disclosed invention is not necessarily limited to the position, size, range, or the like disclosed in the drawings and the like.

In the description of modes of the present invention with reference to the drawings in this specification and the like, the same components in different diagrams are denoted by the same reference numeral.

Embodiment 1

In this embodiment, light-emitting devices of embodiments of the present invention will be described. Note that the light-emitting devices each have a structure in which an EL layer is positioned between a pair of electrodes. The EL layer includes at least a light-emitting layer and may further include functional layers such as a hole-injection layer, a hole-transport layer, an electron-transport layer, and an electron-injection layer.

The light-emitting layer is a layer containing a light-emitting substance (guest material) and also contains a host material. Note that a light-emitting layer of the light-emitting device of one embodiment of the present invention contains a plurality of organic compounds (e.g., a first organic compound and a second organic compound (or a host material and an assist material)) which function as host materials.

Light emission from a light-emitting device is obtained when in a light-emitting layer, energy is transferred from a host material in an excited state generated by recombination of carriers (holes and electrons) to a guest material and the guest material emits light. The light-emitting device described in this embodiment contains a plurality of host materials (a first organic compound and a second organic compound), and can emit phosphorescence as a result of energy transfer from the excited state of a mixture of the host materials (regardless of whether the host materials form an exciplex or not) to a guest material (phosphorescent substance). As to energy transfer from the triplet excited state of the mixed material to the guest material, energy is transferred from a material having a lower T1 level than the rest in the mixed material in the case where reverse intersystem crossing is unlikely to occur (in the case where reverse intersystem crossing is not dominant).

In the case where reverse intersystem crossing is unlikely to occur (in the case where reverse intersystem crossing is not dominant) in the mixed host material of the first organic compound and the second organic compound, at least one of the following two conditions is considered to be satisfied.

The first condition is that at least the first organic compound and the second organic compound are each unlikely to cause reverse intersystem crossing, specifically, that the first organic compound and the second organic compound each have ΔEst, a difference between the singlet excitation level (S1 level) and the triplet excitation level (T1 level), of 0.2 eV or more. In that case, unless the first organic compound and the second organic compound form an exciplex, a difference between the S1 level ($S'_{H(edge)}$) of the mixed material of the first organic compound and the second organic compound ($S'_{H(edge)}$ is derived from the fluorescent spectrum of the mixed material) and the lower ($T_{H(edge)}$) of the T1 level of the first organic compound and the T1 level of the second organic compound is always 0.2 eV or more. Thus, reverse intersystem crossing is unlikely to occur also in the mixed host material of the first organic compound and the second organic compound.

As to the second condition, the case where the first organic compound and the second organic compound form an exciplex needs to be considered. When the exciplex is formed, a new S1 level lower than the S1 levels of the first organic compound and the second organic compound is formed. That is, the S1 level of the exciplex is the S1 level ($S'_{H(edge)}$) of the mixed material (derived from the fluorescent spectrum of the exciplex). Here, when the T1 levels of the first organic compound and the second organic compound are sufficiently high, reverse intersystem crossing occurs in the exciplex. Therefore, the condition under which reverse intersystem crossing is unlikely to occur in the exciplex is also that the difference between the S1 level (i.e., $S'_{H(edge)}$) of the exciplex and the $T_{H(edge)}$ is 0.2 eV or more.

Thus, whether the mixed host material of the first organic compound and the second organic compound forms an exciplex or not, reverse intersystem crossing is unlikely to occur in the mixed host material under the condition that a difference between the S1 level ($S'_{H(edge)}$) of the mixed host material ($S'_{H(edge)}$ is derived from the fluorescent spectrum of the mixed material) and the lower ($T_{H(edge)}$) of the T1 level of the first organic compound and the T1 level of the second organic compound is 0.2 eV or more. Under such a condition, triplet excitation energy transfer from the first organic compound or the second organic compound whichever has a lower T1 level than the other in the mixed host material to the guest material becomes dominant. That is, the present inventor has conceived that the lifetime of such a light-emitting device depends on the lower ($T_{H(edge)}$) of the T1 level of the first organic compound and the T1 level of the second organic compound of the mixed host material.

Figure 2:
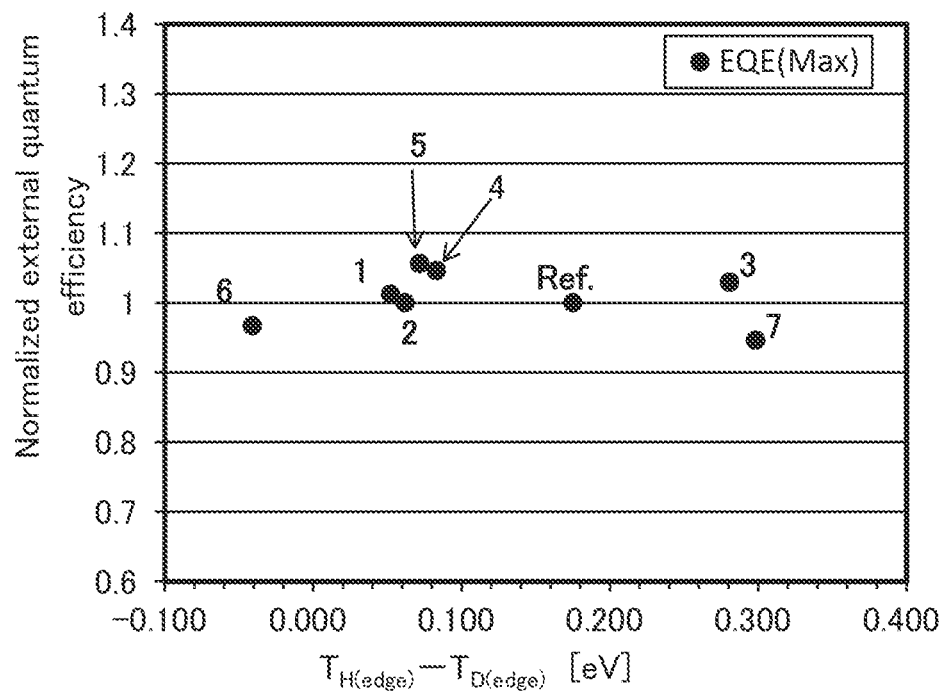
FIG. 2 is a graph showing the relation between $T_{H(edge)} - T_{D(edge)}$ and normalized external quantum efficiency.

First, to examine an influence on external quantum efficiency by the energy difference ($T_{H(edge)}-T_{D(edge)}$) between the $T_{H(edge)}$ of the host material from which energy is transferred and the $T_{D(edge)}$ of the guest material, $T_{H(edge)}$ and $T_{D(edge)}$ were derived from the phosphorescent spectra of the plurality of host materials and the absorption spectrum of the guest material, and normalized external quantum efficiency was calculated based on the value of a reference device, as described in Example 1. As shown in FIG. 2, the influence was approximately the same regardless of the above energy difference ($T_{H(edge)}-T_{D(edge)}$). Therefore, it can be said that the position of the $T_{H(edge)}$ of the host material has a small influence on emission efficiency.

However, the lifetime of the light-emitting device was shortened and the reliability thereof was reduced when endothermic triplet excitation energy transfer occurred, as shown by a light-emitting device 6 (the dot 6 in FIG. 1) among light-emitting devices denoted by reference numerals in FIG. 1. In contrast, a light-emitting device 4 (the dot 4 in FIG. 1) and a light-emitting device 5 (the dot 5 in FIG. 1) had a significantly increased lifetime longer than that of the reference device (Ref.). Thus, a requirement of the present invention is that the value ($T_{H(edge)}-T_{D(edge)}$) needs not only to be 0 or more but also to exceed a certain positive value, so that a long lifetime is ensured. According to FIG. 1, it is necessary that the value ($T_{H(edge)}-T_{D(edge)}$) be 0.07 eV or more. According to Example 3 and Example 4 below, a long lifetime was obtained when the value ($T_{H(edge)}-T_{D(edge)}$) was approximately the lower limit+0.2 eV, that is, 0.27 eV or less; thus, the upper limit of the value ($T_{H(edge)}-T_{D(edge)}$) was set 0.27 eV or less.

Even when the value ($T_{H(edge)}-T_{D(edge)}$) was 0.07 eV or more, the lifetimes of the reference device, a light-emitting device 3, and a light-emitting device 7 were shorter than those of the light-emitting device 4 and the light-emitting device 5. In host materials of the devices with shorter lifetimes, reverse intersystem crossing is likely to occur (the value ($S'H_{(edge)}-T_{H(edge)}$) is less than 0.2 eV). These results suggest that reverse intersystem crossing reduces the lifetime; accordingly, the value ($S'_{H(edge)}-T_{H(edge)}$) is set 0.2 eV or more. In addition, in Example 3 below, a long lifetime is obtained even when the value ($S'_{H(edge)}-T_{H(edge)}$) is approximately 0.4 eV; thus, the upper limit of the value ($S'_{H(edge)}-T_{H(edge)}$) is set 0.5 eV. That is, as a condition under which reverse intersystem crossing is unlikely to occur in the host material and a long lifetime is obtained, the range of the $\Delta E_{s't}=S'_{H(edge)}-T_{H(edge)}$ is set to greater than or equal to 0.2 eV and less than or equal to 0.5 eV. The above conditions are parameters to obtain a light-emitting device with a long lifetime.

In the reference device, the upper limit of the value ($T_{H(edge)}-T_{D(edge)}$) might be more influential than reverse intersystem crossing in the host material; thus, the upper limit of the value ($T_{H(edge)}-T_{D(edge)}$) is preferably 0.17 eV.

The above is summarized as follows: in the light-emitting device of one embodiment of the present invention, the energy difference between the $T_{H(edge)}$ of the host material and the $T_{D(edge)}$ of the guest material in the light-emitting layer ($T_{H(edge)}-T_{D(edge)}$) is greater than or equal to 0.07 eV and less than or equal to 0.27 eV, preferably greater than or equal to 0.07 eV and less than or equal to 0.17 eV, and the energy difference between the $S'_{H(edge)}$ of the host material and the $T_{H(edge)}$ of the host material ($S'_{H(edge)}-T_{H(edge)}$) is greater than or equal to 0.2 eV and less than or equal to 0.5 eV.

The above conditions can be expressed by Formula 1 and Formula 2 below. Note that in the case where the upper limit of the value ($T_{H(edge)}-T_{D(edge)}$) is emphasized, the condition of Formula (3) is more favorable than the condition of Formula (1).

[Formulae 5]

$$0.07 \text{ eV} \leq T_{H(edge)}-T_{D(edge)} \leq 0.27 \text{ eV} \tag{1}$$

$$0.02 \text{ eV} \leq S'_{H(edge)}-T_{H(edge)} \leq 0.5 \text{ eV} \tag{2}$$

$$0.07 \text{ eV} \leq T_{H(edge)}-T_{D(edge)} \leq 0.17 \text{ eV} \tag{3}$$

Thus, the light-emitting device of one embodiment of the present invention includes an EL layer between a pair of electrodes, and the EL layer includes a light-emitting layer that includes a first organic compound, a second organic compound, and a light-emitting substance. The lower ($T_{H(edge)}$) of the T1 level of the first organic compound and the T1 level of the second organic compound and the T1 level ($T_{D(edge)}$) of the light-emitting substance satisfy Formula (1), and a difference between the S1 level ($S'_{H(edge)}$) of a mixed material of the first organic compound and the second organic compound and $T_{H(edge)}$ satisfies Formula (2). Note that the first organic compound and the second organic compound may form an exciplex in combination.

Note that $T_{H(edge)}$ in Formula (1) and Formula (2) represents the lower of the T1 levels derived from the emission edges on the short wavelength side of the phosphorescent spectra of the first organic compound and the second organic compound as host materials of the light-emitting layer; $T_{D(edge)}$ represents the T1 level derived from the absorption edge of the absorption spectrum of the light-emitting substance; and $S'_{H(edge)}$ represents the S1 level derived from the emission edge on the short wavelength side of the fluorescent spectrum of the mixed material of the first organic compound and the second organic compound. Specific examples will be described in detail in Example 1.

Embodiment 2

In this embodiment, a light-emitting device of one embodiment of the present invention will be described with reference to FIGS. 8A and 8B.

<<Structure of Light-Emitting Device>>

Figure 8A:
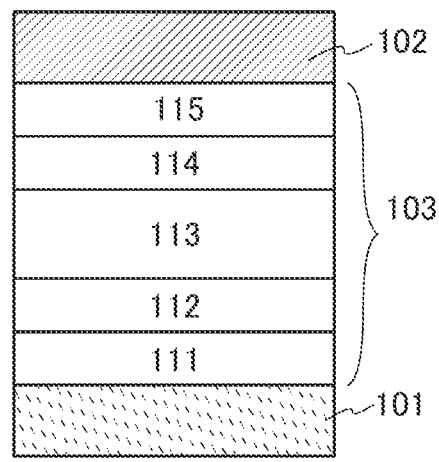
FIGS. 8A and 8B each illustrate the structure of a light-emitting device.
Figure 8B:
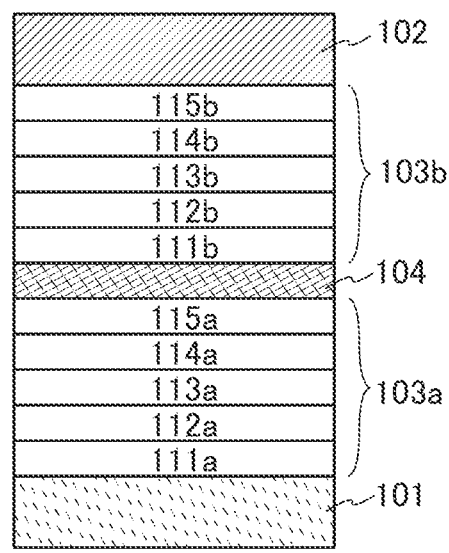

FIGS. 8A and 8B each illustrate an example of a light-emitting device including an EL layer that includes a light-emitting layer between a pair of electrodes. Specifically, an EL layer 103 is provided between a first electrode 101 and a second electrode 102. For example, in the case where the first electrode 101 is an anode, the EL layer 103 has a structure in which a hole-injection layer 111, a hole-transport layer 112, a light-emitting layer 113, an electron-transport layer 114, and an electron-injection layer 115 are stacked as functional layers in this order from the anode side. Embodiments of the present invention also include light-emitting devices having other structures, such as a light-emitting device that can be driven at low voltage by having a structure (tandem structure) where a plurality of EL layers are provided between a pair of electrodes and a charge-generation layer is provided between the EL layers, and a light-emitting device having a micro-optical resonator (microcavity) structure between a pair of electrodes and thus having improved optical characteristics. The charge-generation layer has a function of injecting electrons into one of the adjacent EL layers and injecting holes into the other of the EL layers when voltage is applied between the first electrode 101 and the second electrode 102.

At least one of the first electrode 101 and the second electrode 102 of the light-emitting device is a light-transmitting electrode (e.g., a transparent electrode or a transflective electrode). In the case where the light-transmitting electrode is a transparent electrode, the transparent electrode has a visible light transmittance of higher than or equal to 40%. In the case where the light-transmitting electrode is a transflective electrode, the transflective electrode has a visible light reflectance of higher than or equal to 20% and lower than or equal to 80%, preferably higher than or equal to 40% and lower than or equal to 70%. These electrodes preferably have a resistivity of $1\times10^{-2}$ Ωcm or less.

Furthermore, when one of the first electrode 101 and the second electrode 102 is a reflective electrode in the light-emitting device of one embodiment of the present invention, the visible light reflectance of the reflective electrode is higher than or equal to 40% and lower than or equal to 100%, preferably higher than or equal to 70% and lower than or equal to 100%. This electrode preferably has a resistivity of $1\times10^{-2}$ Ωcm or less.

<First Electrode and Second Electrode>

As materials for the first electrode 101 and the second electrode 102, any of the following materials can be used in an appropriate combination as long as the above functions of the electrodes can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, an In—W—Zn oxide, or the like can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table that is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

For fabrication of these electrodes, a sputtering method or a vacuum evaporation method can be used.

<Hole-Injection Layer>

The hole-injection layer 111 injects holes from the first electrode 101 serving as an anode to the EL layer 103 and contains an organic acceptor material and a material with a high hole-injection property.

The organic acceptor material allows holes to be generated in another organic compound whose HOMO level is close to the LUMO level of the organic acceptor material when charge separation is caused between the organic acceptor material and the organic compound. Thus, as the organic acceptor material, a compound having an electron-withdrawing group (a halogen group or a cyano group), such as a quinodimethane derivative, a chloranil derivative, and a hexaazatriphenylene derivative, can be used. Examples of the organic acceptor material include 7,7,8,8-tetracyano-2,3,5,6-tetrafluoroquinodimethane (abbreviation: $F_4$-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), and 1,3,4,5,7,8-hexafluorotetracyano-naphthoquinodimethane (abbreviation: F6-TCNNQ). Among organic acceptor materials, HAT-CN, which has a high acceptor property and stable film quality against heat, is particularly favorable. Besides, a [3]radialene derivative, which has a very high electron-accepting property, is preferred; specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and cyclopropanetriylidenetris[2,3,4,5,6-pentafluorobenzeneacetonitrile].

As examples of the material with a high hole-injection property, transition metal oxides such as a molybdenum oxide, a vanadium oxide, a ruthenium oxide, a tungsten oxide, and a manganese oxide can be given. It is also possible to use any of phthalocyanine-based compounds such as phthalocyanine (abbreviation: $H_2Pc$) and copper phthalocyanine (abbreviation: CuPc).

Other examples include aromatic amine compounds, which are low molecular compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples include high-molecular compounds (e.g., oligomers, dendrimers, and polymers) such as poly(N-vinylcarbazole) (abbreviation: PVK), poly(-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). Alternatively, a high-molecular compound to which acid is added, such as poly(3,4-ethylenedioxythiophene)/poly(styrenesulfonic acid) (abbreviation: PEDOT/PSS) or polyaniline/poly(styrenesulfonic acid) (abbreviation: PAni/PSS), can be used.

Alternatively, as the material with a high hole-injection property, a composite material containing a hole-transport material and an acceptor material (electron-accepting material) can be used. In that case, the acceptor material extracts electrons from the hole-transport material, so that holes are generated in the hole-injection layer 111 and the holes are injected into the light-emitting layer 113 through the hole-transport layer 112. Note that the hole-injection layer 111 may be formed to have a single-layer structure using a composite material containing a hole-transport material and an acceptor material (electron-accepting material), or a layered structure of a layer containing a hole-transport material and a layer containing an acceptor material (electron-accepting material).

The hole-transport material preferably has a hole mobility of greater than or equal to $1 \times 10^{-6}$ cm$^2$/Vs. Note that other substances may be used as long as the substances have a hole-transport property higher than an electron-transport property.

As the hole-transport material, materials having a high hole-transport property, such as a π-electron rich heteroaromatic compound (e.g., a carbazole derivative and a furan derivative) and an aromatic amine (a compound having an aromatic amine skeleton), are preferable.

Examples of the above carbazole derivative (a compound having a carbazole skeleton) include a bicarbazole derivative (e.g., a 3,3'-bicarbazole derivative) and an aromatic amine having a carbazolyl group.

Specific examples of the above bicarbazole derivative (e.g., a 3,3'-bicarbazole derivative) include 3,3'-bis(9-phenyl-9H-carbazole) (abbreviation: PCCP), 9,9'-bis(1,1'-biphenyl-4-yl)-3,3'-bi-9H-carbazole, 9,9'-bis(1,1'-biphenyl-3-yl)-3,3'-bi-9H-carbazole, 9-(1,1'-biphenyl-3-yl)-9'-(1,1'-biphenyl-4-yl)-9H, 9'H-3,3'-bicarbazole (abbreviation: mBPCCBP), 9-(2-naphthyl)-9'-phenyl-9H, 9'H-3,3'-bicarbazole (abbreviation: βNCCP).

Specific examples of the above aromatic amine having a carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N"-triphenyl-N,N',N"-tris(9-phenylcarbazol-3-yl)benzene-1,3,5-triamine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-

N-(9-phenylcarbazol-3-yl)amino]-9-phenylcarbazole (abbreviation: PCzPCN1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2-[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N'-bis[4-(carbazol-9-yl)phenyl]-N,N'-diphenyl-9,9-dimethylfluorene-2,7-diamine (abbreviation: YGA2F), and 4,4',4"-tris(carbazol-9-yl)triphenylamine (abbreviation: TCTA).

Other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Specific examples of the above furan derivative (a compound having a furan skeleton) include compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV), 4,4',4"-(benzene-1,3,5-triyl)tri(dibenzofuran) (abbreviation: DBF3P-II), and 4-{3-[3-(9-phenyl-9H-fluoren-9-yl)phenyl]phenyl}dibenzofuran (abbreviation: mmDBFFLBi-II).

Specific examples of the above aromatic amine include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]-spiro-9,9'-bifluorene (abbreviation: DPA2SF), 4,4',4"-tris[N-(1-naphthyl)-N-phenylamino]triphenylamine (abbreviation: 1'-TNATA), 4,4',4"-tris(N,N-diphenylamino)triphenylamine (abbreviation: TDATA), 4,4',4"-tris[N-(3-methylphenyl)-N-phenylamino]triphenylamine (abbreviation: m-MTDATA), N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

As the hole-transport material, a high-molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) may be used.

Note that the hole-transport material is not limited to the above examples, and any of a variety of known materials may be used alone or in combination as the hole-transport material.

As the acceptor material for the hole-injection layer 111, an oxide of a metal belonging to any of Group 4 to Group 8 of the periodic table can be used. Specific examples include molybdenum oxide, vanadium oxide, niobium oxide, tantalum oxide, chromium oxide, tungsten oxide, manganese oxide, and rhenium oxide. Among these oxides, molybdenum oxide is especially preferable since it is stable in the air, has a low hygroscopic property, and is easy to handle. It is also possible to use any of the above organic acceptor materials.

The hole-injection layer 111 can be formed by any of known film formation methods such as a vacuum evaporation method.

<Hole-Transport Layer>

The hole-transport layer 112 transports holes injected from the first electrode 101 through the hole-injection layer 111, to the light-emitting layer 113. The hole-transport layer 112 contains a hole-transport material. Thus, the hole-transport layer 112 can be formed using a hole-transport material that can be used for the hole-injection layer 111.

Note that in the light-emitting device of one embodiment of the present invention, the same organic compound as that for the hole-transport layer 112 is preferably used for the light-emitting layer 113. This is because the use of the same organic compounds for the hole-transport layer 112 and the light-emitting layer 113 allows efficient hole transport from the hole-transport layer 112 to the light-emitting layer 113.

<Light-Emitting Layer>

The light-emitting layer 113 contains a light-emitting substance. There is no particular limitation on the light-emitting substance that can be used for the light-emitting layer 113, and a light-emitting substance that converts singlet excitation energy into light emission in the visible light range or a light-emitting substance that converts triplet excitation energy into light emission in the visible light range can be used. Alternatively, a substance whose emission color is blue, violet, bluish violet, green, yellowish green, yellow, orange, red, or the like can be used as appropriate.

In the light-emitting device of one embodiment of the present invention, the light-emitting layer 113 includes a light-emitting substance (guest material) and one or more organic compounds (e.g., host material). Note that as the organic compound (e.g., host material), a substance having a larger energy gap than the light-emitting substance (guest material) is preferably used. Examples of one or more organic compounds (e.g., host material) include organic compounds such as a hole-transport material that can be used in the hole-transport layer 112 described above and an electron-transport material that can be used for the electron-transport layer 114 described later.

Specifically, the light-emitting layer 113 includes a first organic compound, a second organic compound, and a light-emitting substance. The first organic compound is preferably an electron-transport material, and the second organic compound is preferably a hole-transport material. The light-emitting substance is preferably a phosphorescent substance.

Alternatively, the light-emitting layer 113 may include a plurality of light-emitting layers containing different light-emitting substances, to exhibit different emission colors (for example, complementary emission colors may be combined to achieve white light emission). Alternatively, one light-emitting layer may include a plurality of different light-emitting substances.

Examples of the above light-emitting substance are as follows.

As an example of the light-emitting substance that converts singlet excitation energy into light emission, a substance that emits fluorescence (fluorescent material) can be given. Examples of the substance that emits fluorescence include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-diphenyl-N,N'-bis[4-(9-phenyl-9H-fluoren-9-yl)phenyl]pyrene-1,6-diamine (abbreviation: 1,6FLPAPrn), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine] (abbreviation: 1,6BnfAPrn), N,N'-(pyrene-1,6-diyl)bis[(N-phenylbenzo[b]naphtho[1,2-d]furan)-8-amine] (abbreviation: 1,6BnfAPrn-02), and N,N'-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'-(2-tert-butylanthracene-9,10-diyldi-4,1-phenylene)bis[N,N',N''-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

As examples of the light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit the respective emission colors (emission peaks) and thus, any of them is selected appropriately according to need.

As examples of a phosphorescent material which emits blue or green light and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis {2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)) can be given.

As examples of a phosphorescent material which emits green or yellow light and whose emission spectrum has a peak wavelength at greater than or equal to 495 nm and less than or equal to 590 nm, the following substances can be given.

Examples of the phosphorescent material include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis {4,6-dimethyl-2-[6-(2,6-dimethylphenyl)-4-pyrimidinyl-κN$^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$)iridium(III)

acetylacetonate (abbreviation: [Ir(pq)₂(acac)]), bis[2-(2-pyridinyl-κN)phenyl-κC][2-(4-phenyl-2-pyridinyl-κN)phenyl-κC]iridium(III) (abbreviation: [Ir(ppy)₂(4dppy)]), and bis[2-(2-pyridinyl-κN)phenyl-κC][2-(4-methyl-5-phenyl-2-pyridinyl-κN)phenyl-κC]; organometallic complexes such as bis(2,4-diphenyl-1,3-oxazolato-N,C²')iridium(III) acetylacetonate (abbreviation: [Ir(dpo)₂(acac)]), bis{2-[4'-(perfluorophenyl)phenyl]pyridinato-N,C²'}iridium(III) acetylacetonate (abbreviation: [Ir(p-PF-ph)₂(acac)]), and bis(2-phenylbenzothiazolato-N,C²')iridium(III) acetylacetonate (abbreviation: [Ir(bt)₂(acac)]); and a rare earth metal complex such as tris(acetylacetonato)(monophenanthroline)terbium(III) (abbreviation: [Tb(acac)₃(Phen)]).

As examples of a phosphorescent material which emits yellow or red light and whose emission spectrum has a peak wavelength at greater than or equal to 570 nm and less than or equal to 750 nm, the following substances can be given.

Examples include organometallic complexes having a pyrimidine skeleton, such as (diisobutyrylmethanato)bis[4,6-bis(3-methylphenyl)pyrimidinato]iridium(III) (abbreviation: [Ir(5mdppm)₂(dibm)]), bis[4,6-bis(3-methylphenyl)pyrimidinato](dipivaloylmethanato)iridium(III) (abbreviation: [Ir(5mdppm)₂(dpm)]), and (dipivaloylmethanato)bis[4,6-di(naphthalen-1-yl)pyrimidinato]iridium(III) (abbreviation: [Ir(d1npm)₂(dpm)]); organometallic complexes having a pyrazine skeleton, such as (acetylacetonato)bis(2,3,5-triphenylpyrazinato)iridium(III) (abbreviation: [Ir(tppr)₂(acac)]), bis(2,3,5-triphenylpyrazinato)(dipivaloylmethanato)iridium(III) (abbreviation: [Ir(tppr)₂(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ²O,O')iridium(III) (abbreviation: [Ir(dmdppr-P)₂(dibm)]), bis {4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ²O,O')iridium(III) (abbreviation: [Ir(dmdppr-dmCP)₂(dpm)]), (acetylacetonato)bis[2-methyl-3-phenylquinoxalinato-N,C²]iridium(III) (abbreviation: [Ir(mpq)₂(acac)]), (acetylacetonato)bis(2,3-diphenylquinoxalinato-N,C²')iridium(III) (abbreviation: [Ir(dpq)₂(acac)]), and (acetylacetonato)bis[2,3-bis(4-fluorophenyl)quinoxalinato]iridium(III) (abbreviation: [Ir(Fdpq)₂(acac)]); organometallic complexes having a pyridine skeleton, such as tris(1-phenylisoquinolinato-N,C²')iridium(III) (abbreviation: [Ir(piq)₃]) bis(1-phenylisoquinolinato-N,C²')iridium(III) acetylacetonate (abbreviation: [Ir(piq)₂(acac)]), and bis[4,6-dimethyl-2-(2-quinolinyl-κN)phenyl-κC](2,4-pentanedionato-κ²O,O')iridium(III) (abbreviation: [Ir(dmpqn)₂(acac)]); a platinum complex such as 2,3,7,8,12,13,17,18-octaethyl-21H,23H-porphyrin platinum(II) (abbreviation: [PtOEP]); and rare earth metal complexes such as tris(1,3-diphenyl-1,3-propanedionato)(monophenanthroline)europium(III) (abbreviation: [Eu(DBM)₃(Phen)]) and tris[1-(2-thenoyl)-3,3,3-trifluoroacetonato](monophenanthroline)europium(III) (abbreviation: [Eu(TTA)₃(Phen)]).

The above first organic compound that can be used for the light-emitting layer 113 is preferably an electron-transport material. Thus, a π-electron deficient heteroaromatic compound is preferably used. Specifically, having a pyridine ring structure, a diazine ring structure, or a triazine ring structure reduces the LUMO level, facilitating transport of electrons. Examples of the π-electron deficient heteroaromatic compound include pyrimidine derivatives such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm); triazine derivatives such as 2-{4-[3-(N-phenyl-9H-carbazol-3-yl)-9H-carbazol-9-yl]phenyl}-4,6-diphenyl-1,3,5-triazine (abbreviation: PCCzPTzn), and 9-[3-(4,6-diphenyl-1,3,5-triazin-2-yl)phenyl]-9'-phenyl-2,3'-bi-9H-carbazole (abbreviation: mPCCzPTzn-02); pyridine derivatives such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among π-electron deficient heteroaromatic compounds, an organic compound having a structure where an aromatic ring is fused to a furan ring of a furodiazine skeleton is particularly preferred; specific examples are shown below. Note that any of these electron-transport materials can also be used for the electron-transport layer 114 described below.

[Chemical Formula 1]

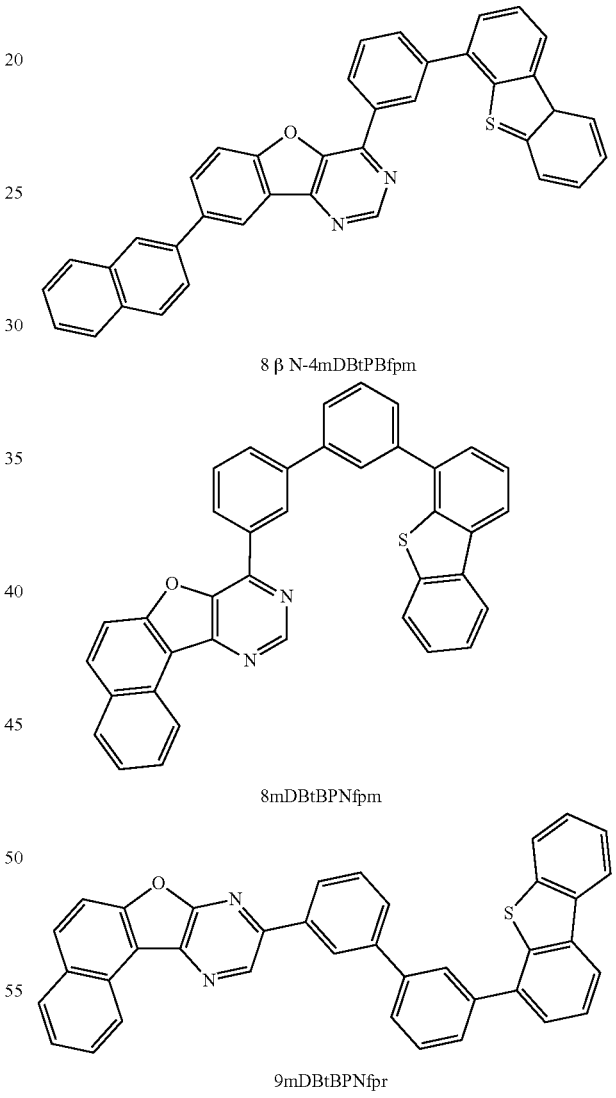

8β N-4mDBtPBfpm

8mDBtBPNfpm

9mDBtBPNfpr

The above second organic compound that can be used for the light-emitting layer 113 is preferably a hole-transport material. Thus, a material having a high hole-transport property, such as a π-electron rich heteroaromatic compound (e.g., a carbazole derivative or a furan derivative) or an aromatic amine (a compound having an aromatic amine skeleton) is preferably used.

Note that when the HOMO level of the second organic compound is too shallow, it forms an exciplex together with the first organic compound and $S_{H(edge)}$ becomes small; accordingly, reverse intersystem crossing is likely to occur. Therefore, among the above, a carbazole derivative, which has a relatively deep HOMO level, is preferred. As a carbazole derivative (a compound having a carbazole skeleton), a bicarbazole derivative (e.g., in particular, a 3,3'-bicarbazole derivative), which has high stability, is preferred. In order not to make the HOMO level too shallow, the carbazole derivative preferably does not have an aromatic amine skeleton (specifically, a triarylamine skeleton).

Specific examples of the bicarbazole derivative (e.g., a 3,3'-bicarbazole derivative) include 3,3'-bis (9-phenyl-9H-carbazole) (abbreviation: PCCP), 9,9'-bis(1,1'-biphenyl-4-yl)-3,3'-bi-9H-carbazole, 9,9'-bis(1,1'-biphenyl-3-yl)-3,3'-bi-9H-carbazole, 9-(1,1'-biphenyl-3-yl)-9'-(1,1'-biphenyl-4-yl)-9H,9'H-3,3'-bicarbazole (abbreviation: mBPCCBP), and 9-(2-naphthyl)-9'-phenyl-9H,9'H-3,3'-bicarbazole (abbreviation: βNCCP).

Besides the above organic compounds, other examples of the organic compound that can be used for the light-emitting layer 113 are given below (some of the following organic compounds overlap with the above) in terms of favorable compatibility with a light-emitting substance (a fluorescent substance or a phosphorescent substance).

In the case where the light-emitting substance is a fluorescent substance, examples of an organic compound that is preferably used in combination with the fluorescent substance include condensed polycyclic aromatic compounds such as an anthracene derivative, a tetracene derivative, a phenanthrene derivative, a pyrene derivative, a chrysene derivative, and a dibenzo[g,p]chrysene derivative.

Specific examples of the organic compound that is preferably used in combination with the fluorescent substance include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 3-[4-(1-naphthyl)-phenyl]-9-phenyl-9H-carbazole (abbreviation: PCPN), 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenyl chrysene, N,N,N',N',N'',N''',N''''-octaphenyldibenzo[g,p]chrysene-2,7,10,15-tetraamine (abbreviation: DBC1), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)-biphenyl-4'-yl}-anthracene (abbreviation: FLPPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl) diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

In the case where the light-emitting substance is a phosphorescent substance, an organic compound having triplet excitation energy (an energy difference between a ground state and a triplet excited state) which is higher than that of the light-emitting substance is preferably selected as an organic compound that is used in combination with the phosphorescent substance. Note that when a plurality of organic compounds (e.g., a first host material and a second host material (or a host material and an assist material)) are used in combination with a light-emitting substance so that an exciplex is formed, the plurality of organic compounds are preferably mixed with a phosphorescent substance.

With such a structure, light emission can be efficiently obtained by exciplex-triplet energy transfer (ExTET), which is energy transfer from an exciplex to a light-emitting substance. Note that a combination of the plurality of organic compounds that easily forms an exciplex is preferably employed, and it is particularly preferable to combine a compound that easily accepts holes (hole-transport material) and a compound that easily accepts electrons (electron-transport material).

In the case where the light-emitting substance is a phosphorescent substance, examples of an organic compound (a host material or an assist material) that is preferably used in combination with the phosphorescent substance include an aromatic amine, a carbazole derivative, a dibenzothiophene derivative, a dibenzofuran derivative, a zinc- or aluminum-based metal complex, an oxadiazole derivative, a triazole derivative, a benzimidazole derivative, a quinoxaline derivative, a dibenzoquinoxaline derivative, a pyrimidine derivative, a pyrazine derivative, a triazine derivative, a pyridine derivative, a bipyridine derivative, and a phenanthroline derivative.

Specific examples thereof include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), triazole derivatives such as 3-(4-biphenylyl)-4-phenyl-5-(4-tert-butylphenyl)-1,2,4-triazole (abbreviation: TAZ) and 3-(4-tert-butylphenyl)-4-(4-ethylphenyl)-5-(4-biphenylyl)-1,2,4-triazole (abbreviation: p-EtTAZ), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), 4,4'-bis(5-methylbenzoxazol-2-yl)stilbene (abbreviation: BzOS), bathophenanthroline (abbreviation: Bphen), bathocuproine (abbreviation: BCP), 2,9-bis(naphthalen-2-yl)-4,7-diphenyl-1,10-phenanthroline (abbreviation: NBphen), and quinoxaline derivatives and dibenzoquinoxaline derivatives, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl) biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Other examples include pyrimidine derivatives such as 4,6-bis[3-(phenanthren-9-yl)phenyl]pyrimidine (abbreviation: 4,6mPnP2Pm), 4,6-bis[3-(4-dibenzothienyl)phenyl] pyrimidine (abbreviation: 4,6mDBTP2Pm-II), and 4,6-bis [3-(9H-carbazol-9-yl)phenyl]pyrimidine (abbreviation: 4,6mCzP2Pm), triazine derivatives such as 2-{4-[3-(N-phenyl-9H-carbazol-3-yl)-9H-carbazol-9-yl]phenyl}-4,6-diphenyl-1,3,5-triazine (abbreviation: PCCzPTzn) and 9-[3-(4,6-diphenyl-1,3,5-triazin-2-yl)phenyl]-9'-phenyl-2,3'-bi- 9H-carbazole (abbreviation: mPCCzPTzn-02), and pyridine derivatives such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB).

Further alternatively, a high-molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used.

In the case where a plurality of organic compounds are used for the light-emitting layer 113, two compounds that form an exciplex (a first compound and a second compound) may be mixed with a light-emitting substance. In that case, any of various organic compounds can be combined appropriately to be used; to form an exciplex efficiently, it is particularly preferable to combine a compound that easily accepts holes (hole-transport material) and a compound that easily accepts electrons (electron-transport material). As the hole-transport material and the electron-transport material, specifically, any of the materials described in this embodiment can be used. With the above structure, high efficiency, low voltage, and a long lifetime can be achieved at the same time.

The TADF material can up-convert a triplet excited state into a singlet excited state (i.e., reverse intersystem crossing is possible) using a little thermal energy and efficiently emit light (fluorescence) from the singlet excited state. Thermally activated delayed fluorescence is efficiently obtained under the condition where the energy difference between the triplet excitation level and the singlet excitation level is greater than or equal to 0 eV and less than or equal to 0.2 eV, preferably greater than or equal to 0 eV and less than or equal to 0.1 eV. Note that "delayed fluorescence" exhibited by the TADF material refers to light emission having the same spectrum as normal fluorescence and an extremely long lifetime. The lifetime is $1 \times 10^{-6}$ seconds or longer, preferably $1 \times 10^{-3}$ seconds or longer.

Examples of the TADF material include fullerene, a derivative thereof, an acridine derivative such as proflavine, and eosin. Other examples include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2$OEP).

Other examples of the TADF material include heterocyclic compounds each having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), and 10-phenyl-10H, 10'H-spiro[acridin-9,9'-anthracen]-10'-one (abbreviation: ACRSA).

Note that a substance in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are improved and the energy difference between the singlet excited state and the triplet excited state becomes small.

Note that when a TADF material is used, the TADF material can be used in combination with another organic compound. In particular, the TADF material can be combined with the host material, the hole-transport material, and the electron-transport material described above. The organic compound of one embodiment of the present invention described in Embodiment 1 is preferably used as a host material that is combined with the TADF material.

Any of the above materials may be used in combination with a low-molecular material or a high-molecular material. For film formation, a known method (a vacuum evaporation method, a coating method, a printing method, or the like) can be used as appropriate.

<Electron-Transport Layer>

The electron-transport layer 114 transports electrons injected from the second electrode 102 through the electron-injection layer 115, to the light-emitting layer 113. Note that the electron-transport layer 114 contains an electron-transport material. It is preferable that the electron-transport material contained in the electron-transport layer 114 be a substance with an electron mobility of higher than or equal to $1 \times 10^{-6}$ cm$^2$/Vs. Note that any other substance can also be used as long as the substance transports electrons more easily than it transports holes. The electron-transport layer 114 functions even with a single-layer structure; however, when the electron-transport layer 114 has a layered structure including two or more layers as needed, the device characteristics can be improved.

Examples of an organic compound that can be used for the electron-transport layer 114 include materials having a high electron-transport property (electron-transport materials), such as an organic compound having a structure where an aromatic ring is fused to a furan ring of a furodiazine skeleton, a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative having a quinoline ligand, a benzoquinoline derivative, a quinoxaline derivative, a dibenzoquinoxaline derivative, a pyridine derivative, a bipyridine derivative, a pyrimidine derivative, and a π-electron deficient heteroaromatic compound (e.g., a nitrogen-containing heteroaromatic compound).

Specific examples of the electron-transport material include metal complexes having a quinoline skeleton or a benzoquinoline skeleton, such as 2-[3'-(dibenzothiophen-4-yl)biphenyl-3-yl]dibenzo[f,h]quinoxaline (abbreviation: 2mDBTBPDBq-II), 2-[3'-(dibenzothiophen-4-yl)biphenyl-3-yl]dibenzo[f,h]quinoxaline (abbreviation: 2mDBTBPDBq-II), 5-[3-(4,6-diphenyl-1,3,5-triazin-2-yl)phenyl]-7,7-dimethyl-5H,7H-indeno[2,1-b]carbazole (abbreviation: mINc(II)PTzn), 4-[3-(dibenzothiophen-4-yl)phenyl]-8-(naphthalen-2-yl)-[1]benzofuro[3,2-d]pyrimidine (abbreviation: 8(3N-4mDBtPBfpm), 3,8-bis[3-(dibenzothiophen-4-yl)phenyl]benzofuro[2,3-b]pyrazine (abbreviation: 3,8mDBtP2Bfpr), 4,8-bis[3-(dibenzothiophen-4-yl)phenyl]-[1]benzofuro[3,2-d]pyrimidine (abbreviation: 4,8mDBtP2Bfpm), 9-[(3'-dibenzothiophen-4-yl)biphenyl-3-yl]naphtho[1',2': 4,5]furo[2,3-b]pyrazine (abbreviation: 9mDBtBPNfpr), 8-[3'-(dibenzothiophen-4-yl)(1,1'-biphenyl-3-yl)]naphtho[1',2': 4,5]furo[3,2-d]pyrimidine (abbreviation: 8mDBtBPNfpm), 8-[(2,2'-binaphthalen)-6-yl]-4-[3-(dibenzothiophen-4-yl)phenyl]-[1]benzofuro[3,2-d]pyrimidine (abbreviation: 8(βN2)-4mDBtPBfpm), tris(8-quinolinolato)aluminum(III) (abbreviation: Alq$_3$), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq), and metal complexes having an oxazole skeleton or a thiazole skeleton, such as bis[2-(2-benzoxazolyl)phenolato]zinc(II) (abbreviation: ZnPBO), bis[2-(2-benzothiazolyl)phenolato]zinc(II) (abbreviation: ZnBTZ), and bis[2-(2-hydroxyphenyl)benzothiazolato]zinc(II) (abbreviation: Zn(BTZ)$_2$).

Other than the metal complexes, it is possible to use oxadiazole derivatives such as PBD, OXD-7, and CO11, triazole derivatives such as TAZ and p-EtTAZ, imidazole derivatives (including benzimidazole derivatives) such as TPBI and mDBTBIm-II, an oxazole derivative such as BzOs, phenanthroline derivatives such as Bphen, BCP, and NBphen, quinoxaline derivatives and dibenzoquinoxaline derivatives, such as 2mDBTPDBq-II, 2mDBTBPDBq-II, 2mCzBPDBq, 2CzPDBq-III, 7mDBTPDBq-II, and 6mDBTPDBq-II, pyridine derivatives such as 35DCzPPy and TmPyPB, pyrimidine derivatives such as 4,6mPnP2Pm, 4,6mDBTP2Pm-II, and 4,6mCzP2Pm, and triazine derivatives such as PCCzPTzn and mPCCzPTzn-02.

It is also possible to use high-molecular compounds such as PPy, PF-Py, and PF-BPy.

<Electron-Injection Layer>

The electron-injection layer 115 is a layer for increasing the efficiency of electron injection from the cathode and is preferably formed using a material whose value of the LUMO level has a small difference (0.5 eV or less) from the work function of a cathode material. Thus, the electron-injection layer 115 can be formed using an alkali metal, an alkaline earth metal, or a compound thereof, such as lithium, cesium, lithium fluoride (LiF), cesium fluoride (CsF), calcium fluoride (CaF$_2$), 8-(quinolinolato)lithium (abbreviation: Liq), 2-(2-pyridyl)phenolatolithium (abbreviation: LiPP), 2-(2-pyridyl)-3-pyridinolato lithium (abbreviation: LiPPy), 4-phenyl-2-(2-pyridyl)phenolato lithium (abbreviation: LiPPP), lithium oxide (LiO$_x$), or cesium carbonate. A rare earth metal compound like erbium fluoride (ErF$_3$) can also be used.

When the charge-generation layer 104 is provided between two EL layers 103a and 103b as in the light-emitting device in FIG. 8B, a structure in which a plurality of EL layers are stacked between the pair of electrodes (the structure is also referred to as a tandem structure) can be obtained. Note that functions and materials of the hole-injection layer 111, the hole-transport layer 112, the light-emitting layer 113, the electron-transport layer 114, and the electron-injection layer 115 that are illustrated in FIG. 8A are the same as those of hole-injection layers 111a and 111b, hole-transport layers 112a and 112b, light-emitting layers 113a and 113b, electron-transport layers 114a and 114b, electron-injection layers 115a and 115b that are illustrated in FIG. 8B.

<Charge-Generation Layer>

In the light-emitting device in FIG. 8B, the charge-generation layer 104 has a function of injecting electrons into the EL layer 103a and injecting holes into the EL layer 103b when a voltage is applied between the first electrode (anode) 101 and the second electrode (cathode) 102. The charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 with the use of any of the above materials can inhibit an increase in drive voltage caused by the stack of the EL layers.

In the case where the charge-generation layer 104 has a structure in which an electron acceptor is added to a hole-transport material, any of the materials described in this embodiment can be used as the hole-transport material. As the electron acceptor, it is possible to use 7,7,8,8-tetracyano-2,3,5,6-tetrafluoroquinodimethane (abbreviation: F$_4$-TCNQ), chloranil, and the like. In addition, oxides of metals that belong to Group 4 to Group 8 of the periodic table can be given. Specific examples are vanadium oxide, niobium oxide, tantalum oxide, chromium oxide, molybdenum oxide, tungsten oxide, manganese oxide, and rhenium oxide.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

Although FIG. 8B illustrates the structure in which two EL layers 103 are stacked, three or more EL layers may be stacked with charge-generation layers each provided between two adjacent EL layers.

<Substrate>

The light-emitting device described in this embodiment can be formed over any of a variety of substrates. Note that the type of substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES); a synthetic resin such as an acrylic resin; polypropylene; polyester; polyvinyl fluoride; polyvinyl chloride; polyamide; polyimide; an aramid resin; an epoxy resin; an inorganic vapor deposition film; and paper.

For fabrication of the light-emitting device in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layers (111, 111a, and 111b), the hole-transport layers (112, 112a, and 112b), the light-emitting layers (113, 113a, and 113b), the electron-transport layers (114, 114a, and 114b), the electron-injection layers (115, 115a, and 115b)) included in the EL layers and the charge-generation layer 104 of the light-emitting device can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, micro-contact printing, or nanoimprint lithography), or the like.

Note that materials that can be used for the functional layers (the hole-injection layers (111, 111a, and 111b), the hole-transport layers (112, 112a, and 112b), the light-emitting layers (113, 113a, and 113b), the electron-transport layers (114, 114a, and 114b), and the electron-injection layers (115, 115a, and 115b)) that are included in the EL layers (103, 103a, and 103b) and the charge-generation layer 104 of the light-emitting device described in this embodiment are not limited to the above materials, and other materials can be used in combination as long as the functions of the layers are fulfilled. For example, a high-molecular compound (e.g., an oligomer, a dendrimer, and a polymer), a middle molecular compound (a compound between a low molecular compound and a high-molecular compound with a molecular weight of 400 to 4000), or an inorganic compound (e.g., a quantum dot material) can be used. The quantum dot material may be a colloidal quantum dot material, an alloyed quantum dot material, a core-shell quantum dot material, a core quantum dot material, or the like.

The structures described in this embodiment can be used in combination with any of the structures described in the other embodiments, as appropriate.

Embodiment 3

Figure 9A:
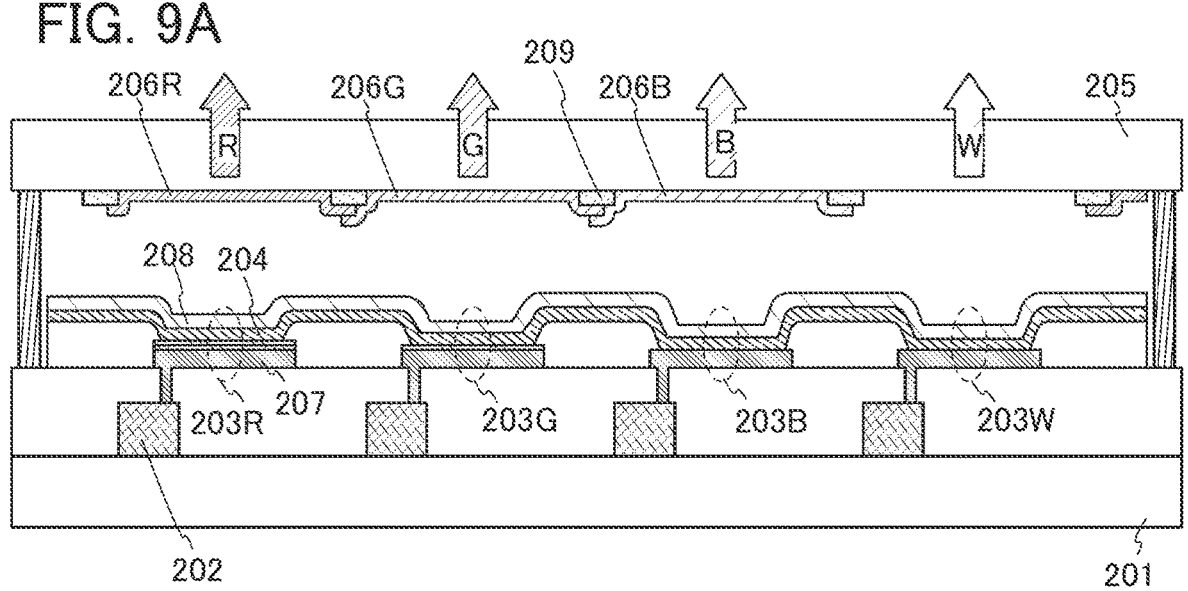
FIGS. 9A to 9C each illustrate a light-emitting apparatus.

In this embodiment, a light-emitting apparatus of one embodiment of the present invention will be described. Note that a light-emitting apparatus illustrated in FIG. 9A is an active-matrix light-emitting apparatus in which transistors (FETs) 202 over a first substrate 201 are electrically connected to light-emitting devices (203R, 203G, 203B, and 203W). The light-emitting devices (203R, 203G, 203B, and 203W) include a common EL layer 204 and each have a microcavity structure in which the optical path length between electrodes is adjusted according to the emission color of the light-emitting device. The light-emitting apparatus is a top-emission light-emitting apparatus in which light is emitted from the EL layer 204 through color filters (206R, 206G, and 206B) formed on a second substrate 205.

The light-emitting apparatus illustrated in FIG. 9A is fabricated such that a first electrode 207 functions as a reflective electrode and a second electrode 208 functions as a transflective electrode. Note that description in any of the other embodiments can be referred to as appropriate for electrode materials for the first electrode 207 and the second electrode 208.

Figure 9B:
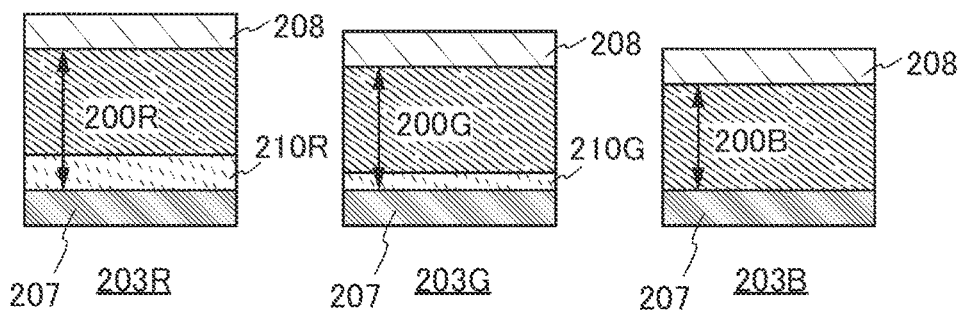

In the case where the light-emitting device 203R functions as a red light-emitting device, the light-emitting device 203G functions as a green light-emitting device, the light-emitting device 203B functions as a blue light-emitting device, and the light-emitting device 203W functions as a white light-emitting device in FIG. 9A, for example, a gap between the first electrode 207 and the second electrode 208 in the light-emitting device 203R is adjusted to have an optical path length 200R, a gap between the first electrode 207 and the second electrode 208 in the light-emitting device 203G is adjusted to have an optical path length 200G, and a gap between the first electrode 207 and the second electrode 208 in the light-emitting device 203B is adjusted to have an optical path length 200B as illustrated in FIG. 9B. Note that optical adjustment can be performed in such a manner that a conductive layer 210R is stacked over the first electrode 207 in the light-emitting device 203R and a conductive layer 210G is stacked over the first electrode 207 in the light-emitting device 203G as illustrated in FIG. 9B.

The second substrate 205 is provided with the color filters (206R, 206G, and 206B). Note that the color filters each transmit visible light in a specific wavelength range and blocks visible light in a specific wavelength range. Thus, as illustrated in FIG. 9A, the color filter 206R that transmits only light in the red wavelength range is provided in a position overlapping with the light-emitting device 203R, whereby red light emission can be obtained from the light-emitting device 203R. Furthermore, the color filter 206G that transmits only light in the green wavelength range is provided in a position overlapping with the light-emitting device 203G, whereby green light emission can be obtained from the light-emitting device 203G. Moreover, the color filter 206B that transmits only light in the blue wavelength range is provided in a position overlapping with the light-emitting device 203B, whereby blue light emission can be obtained from the light-emitting device 203B. Note that the light-emitting device 203W can emit white light without a color filter. Note that a black layer (black matrix) 209 may be provided at an end portion of each color filter. The color filters (206R, 206G, and 206B) and the black layer 209 may be covered with an overcoat layer formed using a transparent material.

Figure 9C:
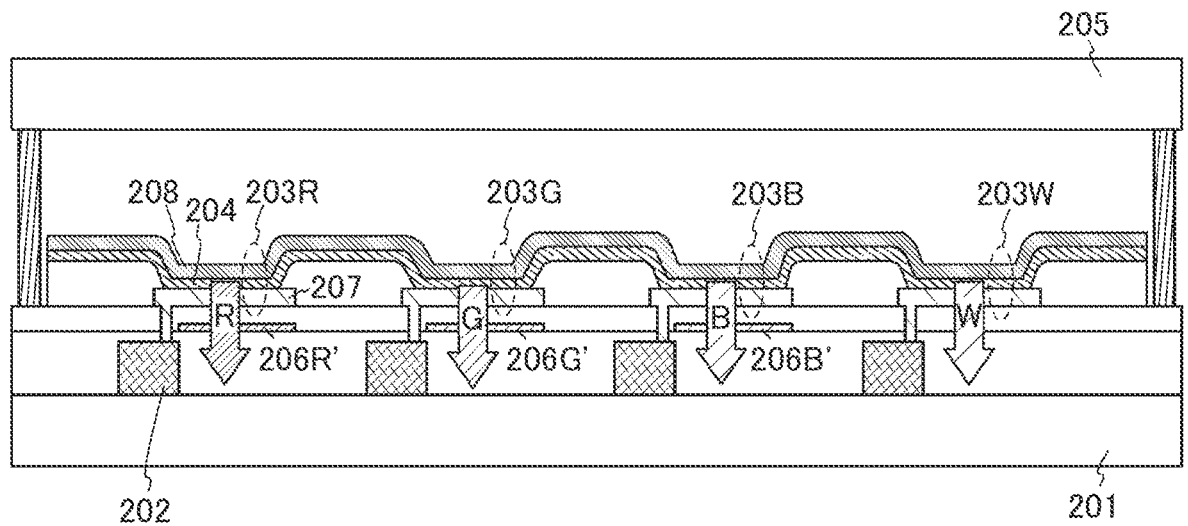

Although the light-emitting apparatus in FIG. 9A has a structure in which light is extracted from the second substrate 205 side (top emission structure), a structure in which light is extracted from the first substrate 201 side where the FETs 202 are formed (bottom emission structure) may be employed as illustrated in FIG. 9C. In the case of a bottom-emission light-emitting apparatus, the first electrode 207 is formed as a transflective electrode and the second electrode 208 is formed as a reflective electrode. As the first substrate 201, a substrate having at least a light-transmitting property is used. As illustrated in FIG. 9C, color filters (206R', 206G', and 206B') are provided closer to the first substrate 201 than the light-emitting devices (203R, 203G, and 203B) are.

In FIG. 9A, the light-emitting devices are the red light-emitting device, the green light-emitting device, the blue light-emitting device, and the white light-emitting device; however, the light-emitting devices of one embodiment of the present invention are not limited to the above, and a yellow light-emitting device or an orange light-emitting device may be used. Note that description in any of the other embodiments can be referred to as appropriate for materials that are used for the EL layers (a light-emitting layer, a hole-injection layer, a hole-transport layer, an electron-transport layer, an electron-injection layer, a charge-generation layer, and the like) to fabricate each of the light-emitting devices. In that case, a color filter needs to be appropriately selected according to the emission color of the light-emitting device.

With the above structure, a light-emitting apparatus including light-emitting devices that exhibit a plurality of emission colors can be fabricated.

The structures described in this embodiment can be used in combination with any of the structures described in the other embodiments, as appropriate.

Embodiment 4

In this embodiment, a light-emitting apparatus of one embodiment of the present invention will be described.

The use of the device structure of the light-emitting device of one embodiment of the present invention allows fabrication of an active-matrix light-emitting apparatus or a passive-matrix light-emitting apparatus. Note that an active-matrix light-emitting apparatus has a structure including a combination of a light-emitting device and a transistor (FET). Thus, each of a passive-matrix light-emitting apparatus and an active-matrix light-emitting apparatus is one embodiment of the present invention. Note that any of the light-emitting devices described in other embodiments can be used in the light-emitting apparatus described in this embodiment.

In this embodiment, an active-matrix light-emitting apparatus will be described with reference to FIGS. 10A and 10B.

Figure 10A:
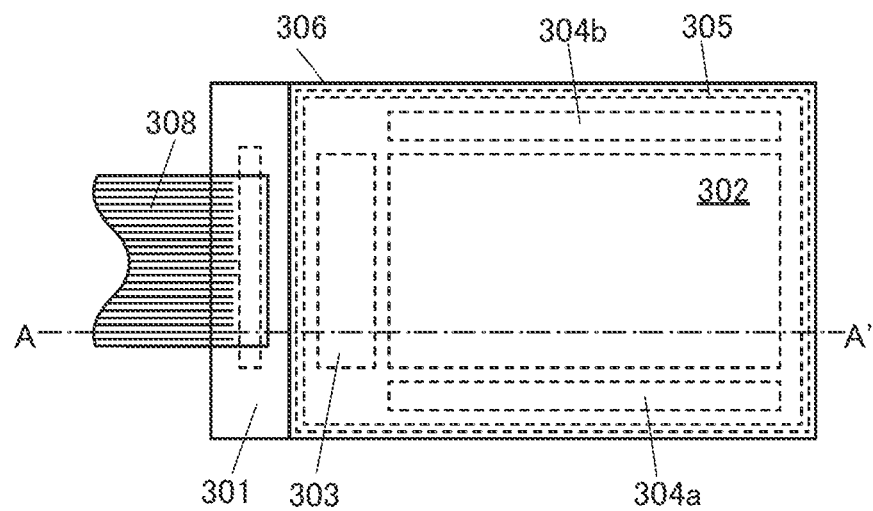
FIG. 10A illustrates the top view of a light-emitting apparatus.
Figure 10B:
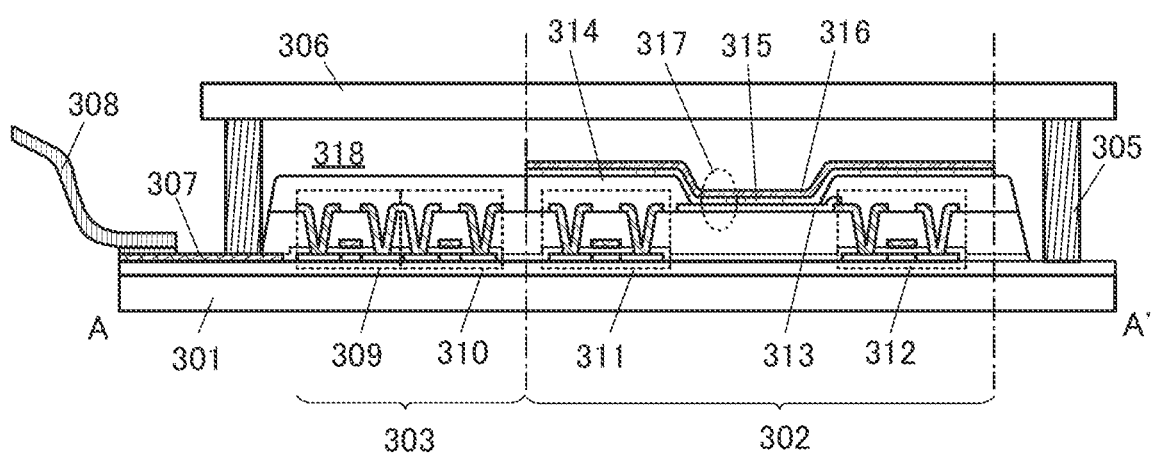
FIG. 10B illustrates a cross section of the light-emitting apparatus.

FIG. 10A is a top view illustrating the light-emitting apparatus, and FIG. 10B is a cross-sectional view taken along chain line A-A' in FIG. 10A. The active-matrix light-emitting apparatus includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is electrically connected to an FPC 308 that is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting apparatus provided with an FPC or a PWB is included in the category of a light-emitting apparatus.

FIG. 10B illustrates a cross-sectional structure of the light-emitting apparatus.

The pixel portion 302 includes a plurality of pixels each of which includes an FET (switching FET) 311, an FET (current control FET) 312, and a first electrode 313 electrically connected to the FET 312. Note that the number of FETs included in each pixel is not particularly limited and can be set appropriately.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be inhibited.

For the semiconductor, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 303 includes the FET 309 and the FET 310. The FET 309 and the FET 310 may be formed with a circuit including transistors having the same conductivity type (either n-channel transistors or p-channel transistors) or a CMOS circuit including an n-channel transistor and a p-channel transistor. Furthermore, a driver circuit may be provided outside.

An end portion of the first electrode 313 is covered with an insulator 314. The insulator 314 can be formed using an organic compound such as a negative photosensitive resin or a positive photosensitive resin (acrylic resin), or an inorganic compound such as silicon oxide, silicon oxynitride, or silicon nitride. The insulator 314 preferably has a curved surface with curvature at an upper end portion or a lower end portion thereof. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the components of a light-emitting device 317 described in this embodiment. Although not illustrated, the second electrode 316 is electrically connected to the FPC 308 that is an external input terminal.

Although the cross-sectional view in FIG. 10B illustrates only one light-emitting device 317, a plurality of light-emitting devices are arranged in a matrix in the pixel portion 302. Light-emitting devices that emit light of three kinds of colors (R, G, and B) are selectively formed in the pixel portion 302, whereby a light-emitting apparatus capable of displaying a full-color image can be obtained. In addition to the light-emitting devices that emit light of three kinds of colors (R, G, and B), for example, light-emitting devices that emit light of white (W), yellow (Y), magenta (M), cyan (C), and the like may be formed. For example, the light-emitting devices that emit light of some of the above colors are used in combination with the light-emitting devices that emit light of three kinds of colors (R, G, and B), whereby effects such as an improvement in color purity and a reduction in power consumption can be achieved. Alternatively, a light-emitting apparatus which is capable of displaying a full-color image may be fabricated by a combination with color filters. As color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting device 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy resin, glass frit, or the like can be used for the sealant 305. It is preferable to use a material that is permeable to as little moisture and oxygen as possible for the sealant 305. As the second substrate 306, a substrate that can be used as the first substrate 301 can be similarly used. Thus, any of the various substrates described in the other embodiments can be appropriately used. As the substrate, a glass substrate, a quartz substrate, or a plastic substrate made of fiber-reinforced plastic (FRP), polyvinyl fluoride (PVF), polyester, acrylic resin, or the like can be used. In the case where glass frit is used for the sealant, the first substrate 301 and the second substrate 306 are preferably glass substrates in terms of adhesion.

Accordingly, the active-matrix light-emitting apparatus can be obtained.

In the case where the active-matrix light-emitting apparatus is provided over a flexible substrate, the FETs and the light-emitting device may be directly formed over the flexible substrate; alternatively, the FETs and the light-emitting device may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (silk, cotton, or hemp), a synthetic fiber (nylon, polyurethane, or polyester), a regenerated fiber (acetate, cupra, rayon, or regenerated polyester), or the like), a leather substrate, and a rubber substrate. With the use of any of these substrates, an increase in durability, an increase in heat resistance, a reduction in weight, and a reduction in thickness can be achieved.

The light-emitting device included in the active matrix light-emitting apparatus may emit pulsed light (with a frequency of kHz or MHz, for example) so that the light is used for display. The light-emitting device formed using any of the above organic compounds has excellent frequency characteristics; therefore, time for driving the light-emitting device can be shortened, resulting in a reduction in power consumption. Furthermore, a reduction in driving time leads to inhibition of heat generation, so that the degree of deterioration of the light-emitting device can be reduced.

The structures described in this embodiment can be used in combination with any of the structures described in the other embodiments, as appropriate.

Embodiment 5

In this embodiment, examples of a variety of electronic devices and an automobile manufactured using the light-emitting device of one embodiment of the present invention or a light-emitting apparatus including the light-emitting device of one embodiment of the present invention will be described. Note that the light-emitting apparatus can be used mainly in a display portion of the electronic device described in this embodiment.

Electronic devices illustrated in FIGS. 11A to 11E can include a housing 7000, a display portion 7001, a speaker 7003, an LED lamp 7004, operation keys 7005 (including a power switch or an operation switch), a connection terminal 7006, a sensor 7007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

Figure 11A:
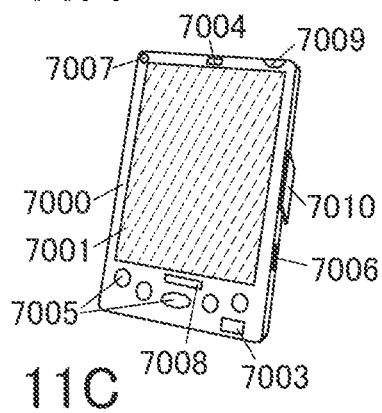
FIG. 11A illustrates a mobile computer.

FIG. 11A illustrates a mobile computer that can include a switch 7009, an infrared port 7010, and the like in addition to the above components.

Figure 11B:
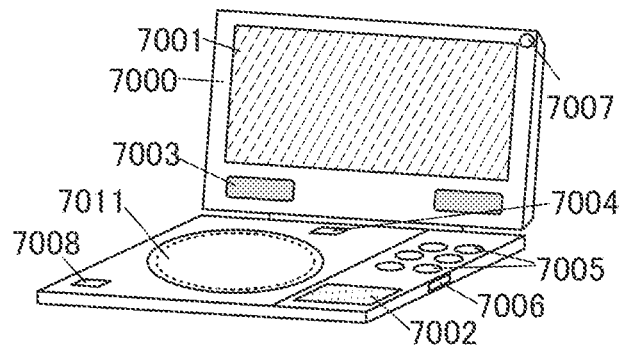
FIG. 11B illustrates a portable image reproducing device.

FIG. 11B illustrates a portable image reproducing device (e.g., a DVD player) that is provided with a recording medium and can include a second display portion 7002, a recording medium reading portion 7011, and the like in addition to the above components.

Figure 11C:
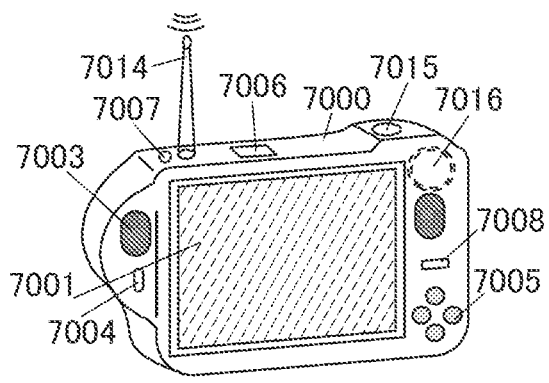
FIG. 11C illustrates a digital camera.

FIG. 11C illustrates a digital camera that has a television reception function and can include an antenna 7014, a shutter button 7015, an image receiving portion 7016, and the like in addition to the above components.

Figure 11D:
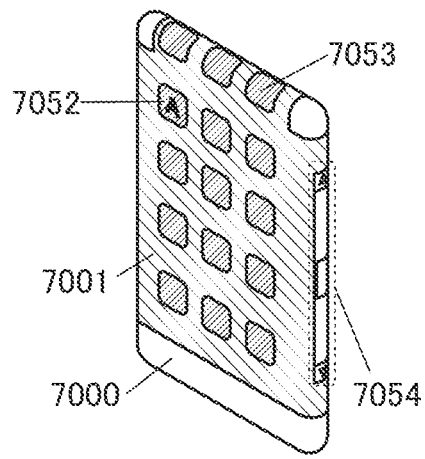
FIG. 11D illustrates a portable information terminal.

FIG. 11D illustrates a portable information terminal. The portable information terminal has a function of displaying information on three or more surfaces of the display portion 7001. Here, information 7052, information 7053, and information 7054 are displayed on different surfaces. For example, a user of the portable information terminal can check the information 7053 displayed such that it can be seen from above the portable information terminal, with the portable information terminal put in a breast pocket of his/her clothes. Thus, the user can see the display without taking out the portable information terminal from the pocket and decide whether to answer the call, for example.

Figure 11E:
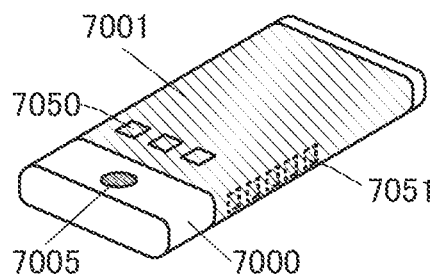
FIG. 11E illustrates a portable information terminal.

FIG. 11E illustrates a portable information terminal (e.g., a smartphone) and can include the display portion 7001, the operation key 7005, and the like in the housing 7000. Note that the portable information terminal may include a speaker, a connection terminal, a sensor, or the like. The portable information terminal can display text and image data on its plurality of surfaces.

Here, three icons 7050 are displayed. Furthermore, information 7051 indicated by dashed rectangles can be displayed on another surface of the display portion 7001. Examples of the information 7051 include notification of reception of an e-mail, an SNS message, or an incoming call, the title and sender of an e-mail, an SNS message, or the like, the date, the time, remaining battery, and the reception strength of an antenna. The icon 7050 or the like may be displayed at the position where the information 7051 is displayed.

Figure 11F:
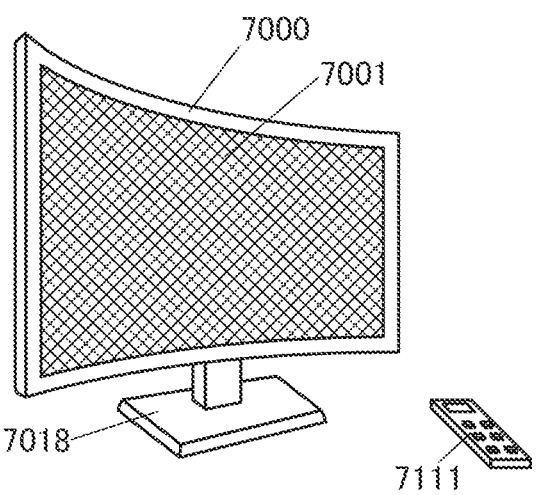
FIG. 11F illustrates a television set.

FIG. 11F illustrates a large-size television set (also referred to as TV or a television receiver) and can include the housing 7000, the display portion 7001, and the like. In addition, here, the housing 7000 is supported by a stand 7018. The television set can be operated with a separate remote controller 7111 or the like. The display portion 7001 may include a touch sensor. The television set can be operated by touching the display portion 7001 with a finger or the like. The remote controller 7111 may be provided with a display portion for displaying information output from the remote controller 7111. With operation keys or a touch panel of the remote controller 7111, channels and volume can be controlled and images displayed on the display portion 7001 can be controlled.

The electronic devices illustrated in FIGS. 11A to 11F can have a variety of functions, such as a function of displaying a variety of information (a still image, a moving image, a text image, and the like) on the display portion, a touch panel function, a function of displaying a calendar, date, time, and the like, a function of controlling processing with a variety of types of software (programs), a wireless communication function, a function of connecting to a variety of computer networks with a wireless communication function, a function of transmitting and receiving a variety of data with a wireless communication function, a function of reading a program or data stored in a recording medium and displaying the program or data on the display portion, and the like. Furthermore, the electronic device including a plurality of display portions can have a function of displaying image data mainly on one display portion while displaying text data mainly on another display portion, a function of displaying a three-dimensional image by displaying images on a plurality of display portions with a parallax taken into account, or the like. Furthermore, the electronic device including an image receiving portion can have a function of shooting a still image, a function of shooting a moving image, a function of automatically or manually correcting a shot image, a function of storing a shot image in a recording medium (an external recording medium or a recording medium incorporated in the camera), a function of displaying a shot image on the display portion, or the like. Note that functions that can be provided for the electronic devices illustrated in FIGS. 11A to 11F are not limited to those described above, and the electronic devices can have a variety of functions.

Figure 11G:
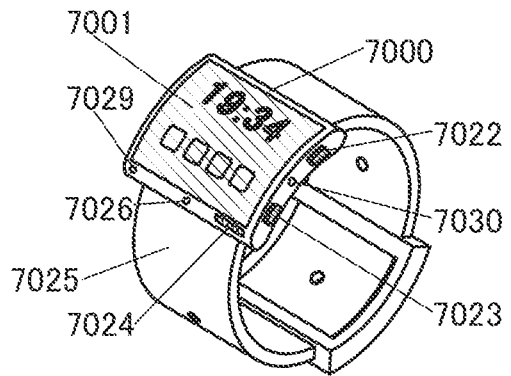
FIG. 11G illustrates a portable information terminal.

FIG. 11G illustrates a watch-type portable information terminal, which can be used as a smart watch, for example. The watch-type portable information terminal includes the housing 7000, the display portion 7001, operation buttons 7022 and 7023, a connection terminal 7024, a band 7025, a microphone 7026, a sensor 7029, a speaker 7030, and the like. The display surface of the display portion 7001 is curved, and images can be displayed on the curved display surface. Furthermore, mutual communication between the portable information terminal and, for example, a headset capable of wireless communication can be performed, and thus hands-free calling is possible with the portable information terminal. Note that the connection terminal 7024 allows mutual data transmission with another information terminal and charging. Wireless power feeding can also be employed for the charging operation.

The display portion 7001 mounted in the housing 7000 serving as a bezel includes a non-rectangular display region. The display portion 7001 can display an icon indicating time, another icon, and the like. The display portion 7001 may be a touch panel (input/output device) including a touch sensor (input device).

The smart watch illustrated in FIG. 11G can have a variety of functions, such as a function of displaying a variety of information (e.g., a still image, a moving image, and a text image) on the display portion, a touch panel function, a function of displaying a calendar, date, time, and the like, a function of controlling processing with a variety of types of software (programs), a wireless communication function, a function of connecting to a variety of computer networks with a wireless communication function, a function of transmitting and receiving a variety of data with a wireless communication function, and a function of reading a program or data stored in a recording medium and displaying the program or data on the display portion.

The housing 7000 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like.

Note that the light-emitting apparatus of one embodiment of the present invention can be used in the display portion of each electronic device described in this embodiment, so that a long lifetime electronic device can be obtained.

Figure 12A:
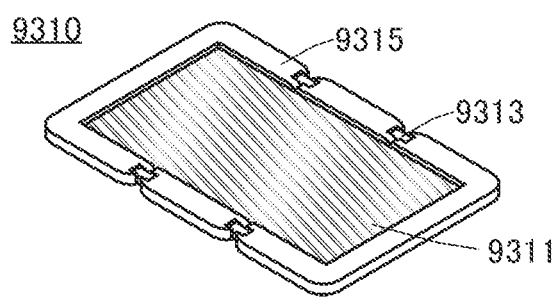
FIGS. 12A to 12C illustrate an electronic device.
Figure 12B:
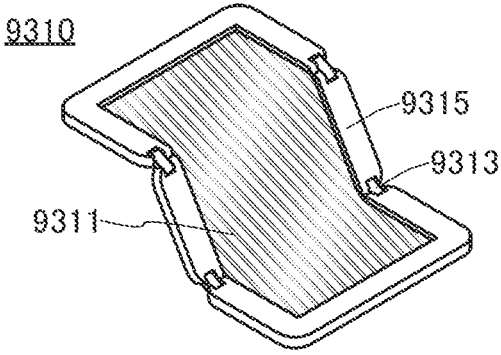
Figure 12C:
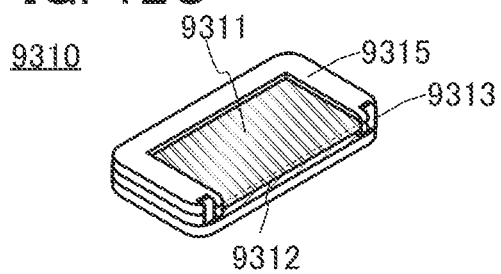

Another electronic device including the light-emitting apparatus is a foldable portable information terminal illustrated in FIGS. 12A to 12C. FIG. 12A illustrates a portable information terminal 9310 which is opened. FIG. 12B illustrates the portable information terminal 9310 which is being opened or being folded. FIG. 12C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (input/output device) including a touch sensor (input device). By bending the display portion 9311 at a connection portion between two housings 9315 with the use of the hinges 9313, the portable information terminal 9310 can be reversibly changed in shape from an opened state to a folded state. The light-emitting apparatus of one embodiment of the present invention can be used for the display portion 9311. In addition, a long lifetime electronic device can be obtained. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application and the like can be smoothly performed.

Figure 13A:
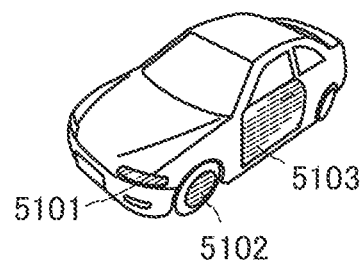
FIGS. 13A and 13B illustrate an automobile.
Figure 13B:
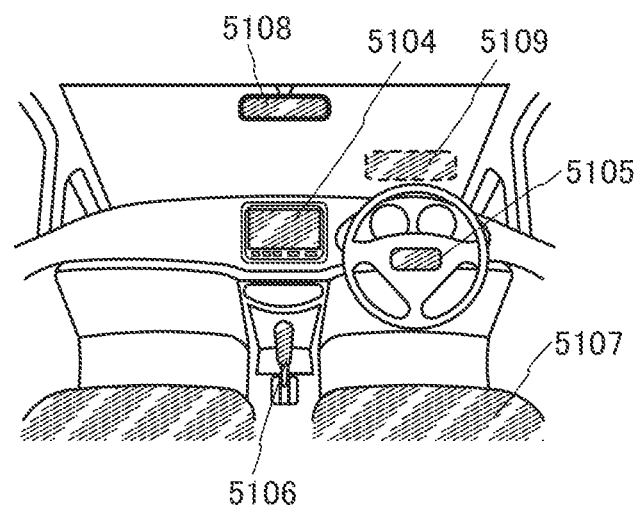

FIGS. 13A and 13B illustrate an automobile including the light-emitting apparatus. The light-emitting apparatus can be incorporated in the automobile, and specifically, can be included in lights 5101 (including lights of the rear part of the car), a wheel cover 5102, a part or whole of a door 5103, or the like on the outer side of the automobile which is illustrated in FIG. 13A. The light-emitting apparatus can also be included in a display portion 5104, a steering wheel 5105, a gear lever 5106, a seat 5107, an inner rearview mirror 5108, an windshield 5109, or the like on the inner side of the automobile which is illustrated in FIG. 13B, or in a part of a glass window.

In the above manner, the electronic devices and automobiles can be obtained using the light-emitting apparatus of one embodiment of the present invention. In that case, a long lifetime electronic device can be obtained. Note that the light-emitting apparatus can be used for electronic devices and automobiles in a variety of fields without being limited to those described in this embodiment.

The structures described in this embodiment can be used in combination with any of the structures described in the other embodiments, as appropriate.

Embodiment 6

In this embodiment, the structure of a lighting device fabricated using the light-emitting apparatus of one embodiment of the present invention or the light-emitting device which is part of the light-emitting apparatus will be described with reference to FIGS. 14A and 14B.

Figure 14A:
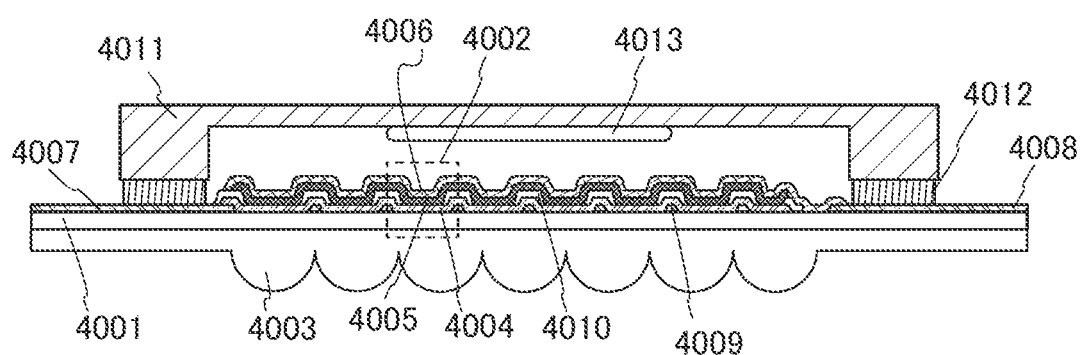
FIGS. 14A and 14B each illustrate a lighting device.
Figure 14B:
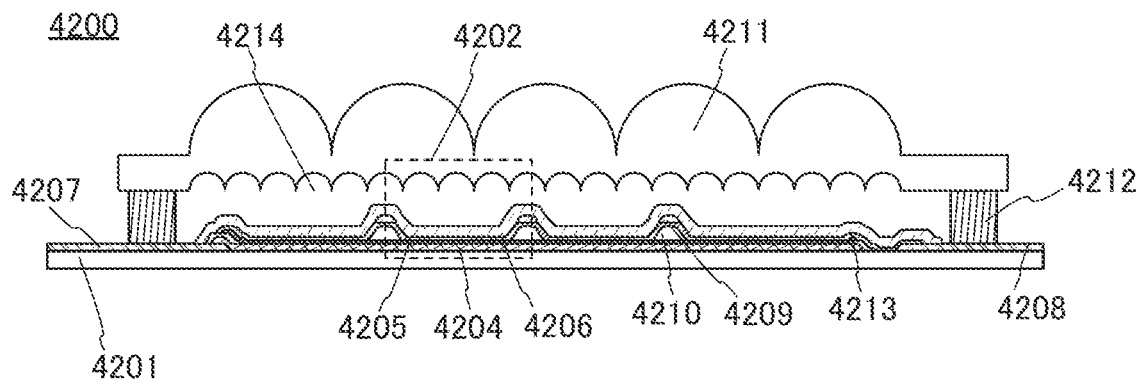

FIGS. 14A and 14B are examples of cross-sectional views of lighting devices. FIG. 14A illustrates a bottom-emission lighting device in which light is extracted from the substrate side, and FIG. 14B illustrates a top-emission lighting device in which light is extracted from the sealing substrate side.

A lighting device 4000 illustrated in FIG. 14A includes a light-emitting device 4002 over a substrate 4001. In addition, the lighting device 4000 includes a substrate 4003 with unevenness on the outside of the substrate 4001. The light-emitting device 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting device 4002. The substrate 4003 has the unevenness illustrated in FIG. 14A, whereby the extraction efficiency of light emitted from the light-emitting device 4002 can be increased.

A lighting device 4200 illustrated in FIG. 14B includes a light-emitting device 4202 over a substrate 4201. The light-emitting device 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting device 4202. The sealing substrate 4211 has the unevenness illustrated in FIG. 14B, whereby the extraction efficiency of light emitted from the light-emitting device 4202 can be increased.

Examples of such lighting devices include a ceiling light as an indoor lighting. Examples of the ceiling light include a direct-mount light and an embedded light. Such lighting devices are fabricated using the light-emitting apparatus and a housing or a cover in combination.

For another example, such lighting devices can be used for a foot light that lights a floor so that safety on the floor can be improved. A foot light can be effectively used in a bedroom, on a staircase, or on a passage, for example. In that case, the size or shape of the foot light can be changed in accordance with the area or structure of a room. The foot light can be a stationary lighting device fabricated using the light-emitting apparatus and a support in combination.

Such lighting devices can also be used for a sheet-like lighting device (sheet-like lighting). The sheet-like lighting, which is attached to a wall when used, is space-saving and thus can be used for a wide variety of uses. Furthermore, the area of the sheet-like lighting can be easily increased. The sheet-like lighting can also be used on a wall or housing having a curved surface.

Besides the above examples, when the light-emitting apparatus of one embodiment of the present invention or the light-emitting device which is part of the light-emitting apparatus is used as part of furniture in a room, a lighting device that functions as the furniture can be obtained.

As described above, a variety of lighting devices that include the light-emitting apparatus can be obtained. Note that these lighting devices are also embodiments of the present invention.

Note that the structures described in this embodiment can be used in combination with any of the structures described in the other embodiments, as appropriate.

Example 1

In this example, a plurality of light-emitting devices using host materials having different T1 levels were fabricated, and influence on the reliability of each of the light-emitting devices by the relation between the T1 level of a host material for a light-emitting layer of the light-emitting device and the excitation energy of a light-emitting substance (phosphorescent substance) was examined. The results will be described below.

In this example, Table 1 lists the structures of the fabricated light-emitting devices.

TABLE 1

| | First electrode | Hole-injection layer | Hole-transport layer | Light-emitting layer* (only one of host materials) | Electron-transport layer | | Electron-injection layer | Second electrode |
|---|---|---|---|---|---|---|---|---|
| Reference device | ITSO (70 nm) | DBT3P-II: MoOx (2:1 50 nm) | PCBBiIBP (20 nm) | mPCCzPTzn-02 (40 nm) | mPCCzPTzn-02 (20 nm) | | | |
| Light-emitting device 1 (Comparative example) | | | | 2mDBTBPDBq-II (40 nm) | 2mDBTBPDBq-II (20 nm) | Bphen (15 nm) | LiF (1 nm) | Al (200 nm) |
| Light-emitting device 2 (Comparative example) | | | | 2mPCCzPDBq-02 (40 nm) | 2mPCCzPDBq-02 (20 nm) | | | |
| Light-emitting device 3 (Comparative example) | | | | mINc(II)PTzn (40 nm) | mINc(II)PTzn (20nm) | | | |
| Light-emitting device 4 | | | | 8βN-4mDBtPBfpm (40 nm) | 8βN-4mDBtPBfpm (20 nm) | | | |

TABLE 1-continued

| | First electrode | Hole-injection layer | Hole-transport layer | Light-emitting layer* (only one of host materials) | Electron-transport layer | Electron-injection layer | Second electrode |
|---|---|---|---|---|---|---|---|
| Light-emitting device 5 | | | | 8mDBtBPNfpm (40 nm) | mPCCzPTzn-02 (20 nm) | | |
| Light-emitting device 6 (Comparative example) | | | | 3,8mDBtP2Bfpr (40 nm) | 3,8mDBtP2Bfpr (20 nm) | | |
| Light-emitting device 7 (Comparative example) | | | | 4,8mDBtP2Bfpm (40 nm) | 4,8mDBtP2Bfpm (20 nm) | | |

*Other materials in the light-emitting layer PCCP, [Ir(ppy)$_2$(4dppy)]

The molecular structures of the host materials and the guest materials (phosphorescent substances) used in the light-emitting devices listed in Table 1 are shown below.

[Chemical Formulae 2]

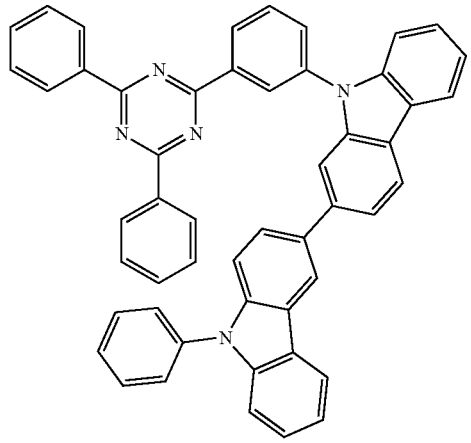

mPCCzPTzn-02
(ref.)

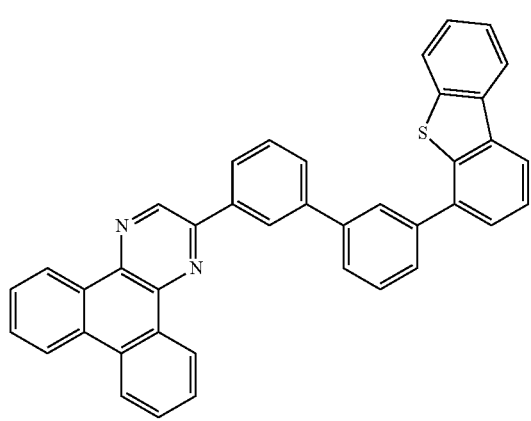

2mPCCzPDBq-02

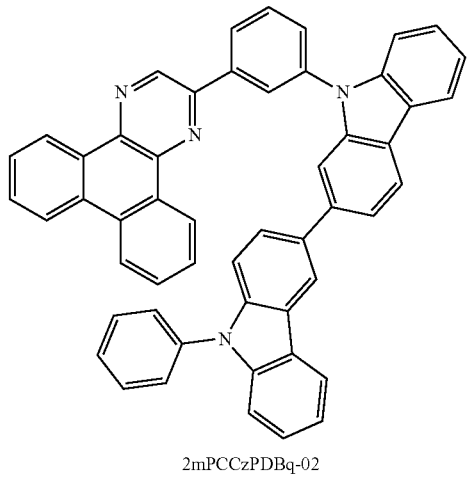

mINc(II)PTzn

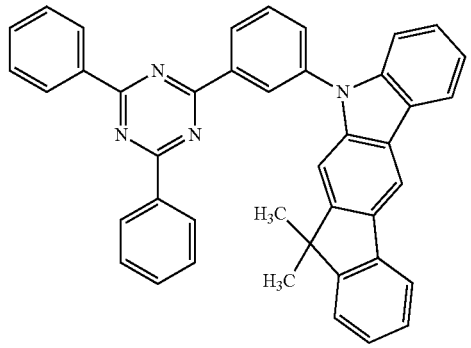

2mDBtBPDBq-II

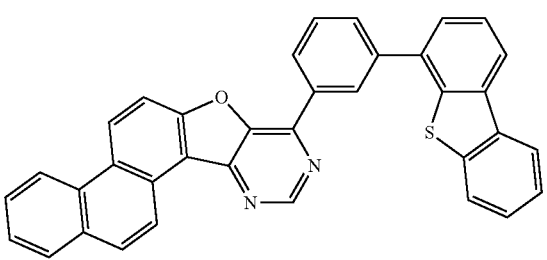

8 β N–4mDBtBPBfpm

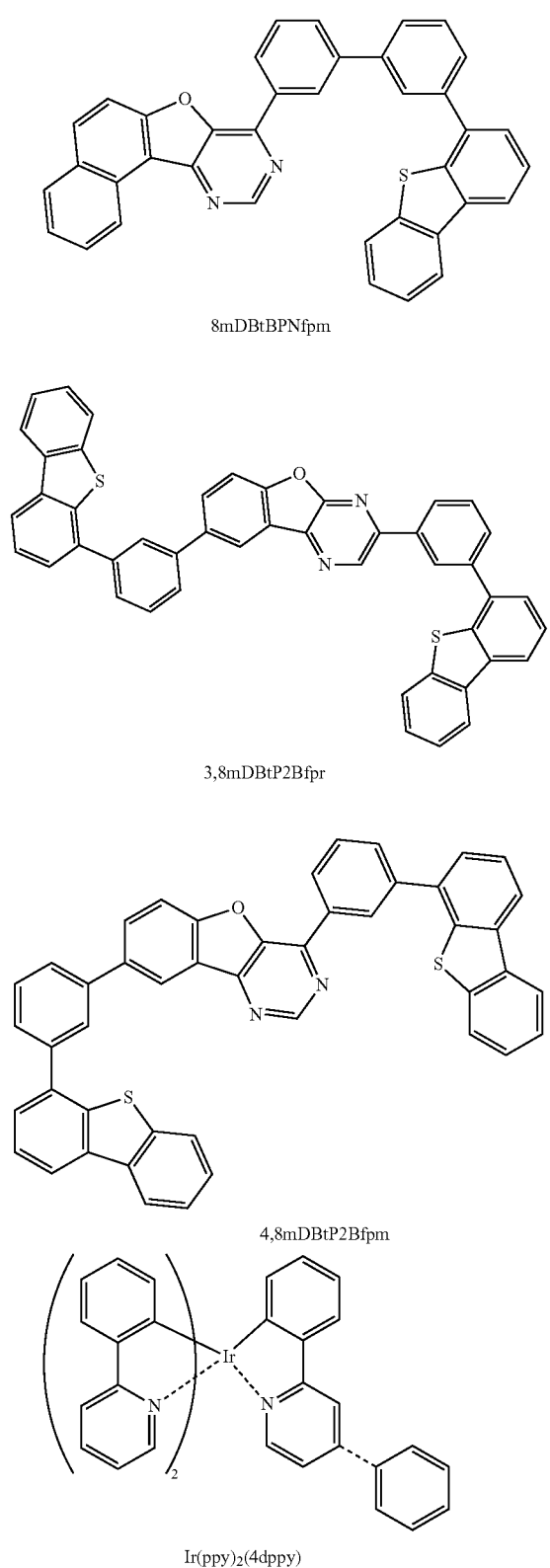

In this example, for comparison of the T1 levels of the host materials, $T_{H(edge)}$ was calculated from an emission edge on the short wavelength side of each of the phosphorescent spectra (the onset of each of the spectra).

Figure 3:
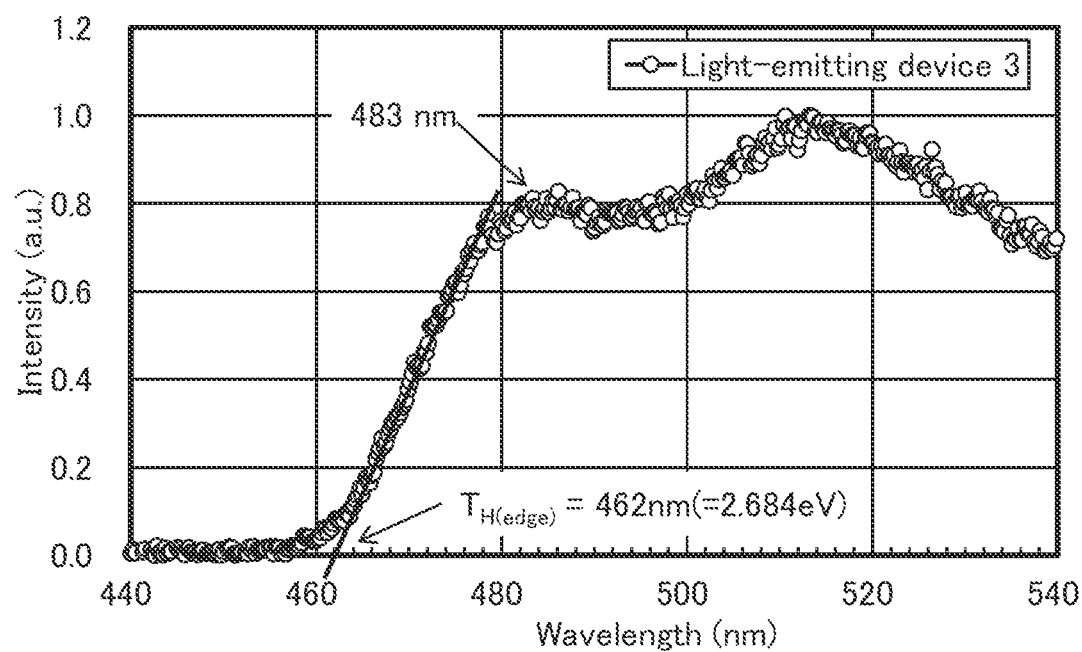
FIG. 3 shows a method for calculating $T_{H(edge)}$ from the phosphorescent spectrum.

The emission edge of a phosphorescent spectrum is the wavelength at the intersection of the horizontal axis and a tangent drawn to the curve on the short wavelength side at around the half of a peak on the shortest wavelength side, and $T_{H(edge)}$ can be derived from this value. For example, the emission edge of the phosphorescent spectrum in FIG. 3 is the intersection (at 462 nm) of the horizontal axis and a tangent drawn to the curve at around the half of a peak (at 483 nm) on the shortest wavelength side. The $T_{H(edge)}$ of the substance having the phosphorescent spectrum in FIG. 3 is calculated from the value to be 2.684 eV.

Note that the phosphorescent spectrum in FIG. 3 is the spectrum of a material used for a light-emitting layer of the light-emitting device 3 shown in Table 1. The light-emitting layer of the light-emitting device 3 contains 5-[3-(4,6-diphenyl-1,3,5-triazin-2-yl)phenyl]-7,7-dimethyl-5H,7H-indeno[2,1-b]carbazole (abbreviation: mINc(II)PTzn) and 3,3'-bis(9-phenyl-9H-carbazole) (abbreviation: PCCP) as host materials and [2-(4-phenyl-2-pyridinyl-κN)phenyl-KC]bis[2-(2-pyridinyl-κN)phenyl-κC]iridium(III) (abbreviation: [Ir(ppy)₂(4dppy)]) as a guest material (phosphorescent substance).

Figure 4:
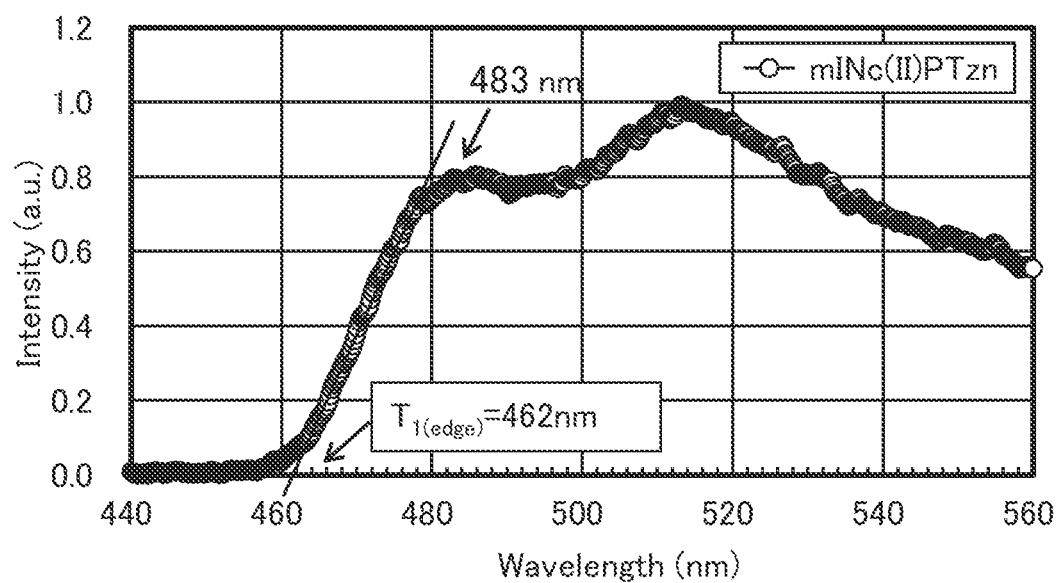
FIG. 4 shows a method for calculating $T_{H(edge)}$ from the phosphorescent spectrum.
Figure 5:
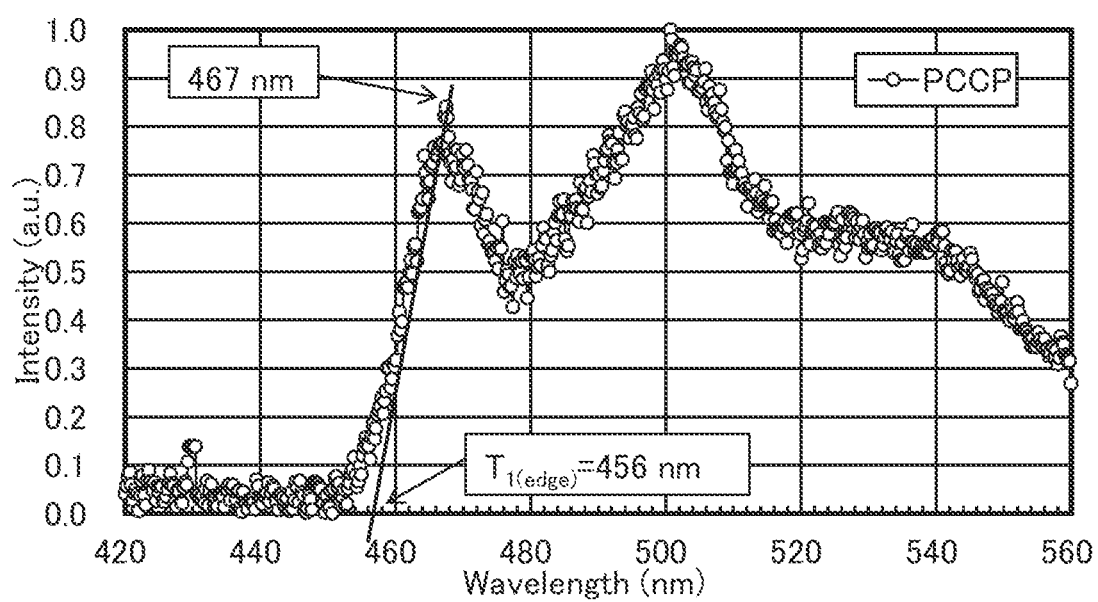
FIG. 5 shows a method for calculating $T_{H(edge)}$ from the phosphorescent spectrum.

The phosphorescent spectra of mINc(II)PTzn and PCCP were measured; the phosphorescent spectrum of mINc(II)PTzn and the phosphorescent spectrum of PCCP are shown in FIG. 4 and FIG. 5, respectively.

According to the phosphorescent spectrum of FIG. 4, the emission edge of mINc(II)PTzn on the short wavelength side (the onset of the spectrum) is 462 nm, which can be converted into an energy of 2.684 eV. According to the results in FIG. 5, the emission edge of PCCP on the short wavelength side (the onset of the spectrum) is 456 nm, which can be converted into an energy of 2.719 eV.

Accordingly, in the light-emitting layer of the light-emitting device 3, the T1 level of mINc(II)PTzn (first organic compound), which is the lower of the T1 levels of mINc(II)PTzn and PCCP (second organic compound), is 2.684 eV; thus, the $T_{H(edge)}$ in the light-emitting device 3 can be determined to be 2.684 eV. In addition, it can be said that triplet excitation energy transfer in the light-emitting layer occurs from mINc(II)PTzn, whose T1 level is lower than that of the host materials PCCP, to the guest material (light-emitting substance), when reverse intersystem crossing does not occur.

Note that the $T_{H(edge)}$ of the host material used in each of the light-emitting devices in Table 1, which was measured from the phosphorescent spectra of the first organic compound and the second organic compound in the same manner as that of the light-emitting device 3, was coincident with the $T_{H(edge)}$ of a material as the host material of the light-emitting layer in Table 1 (that is, the T1 level of the host material of each of the light-emitting devices is lower than that of PCCP). This suggests that triplet excitation energy is transferred from the host material with $T_{H(edge)}$ shown in Table 2 to the guest material (light-emitting substance) in the light-emitting layer of each of the light-emitting devices.

TABLE 2

| | | Host material | $T_{H(edge)}$ of host material [eV] |
|---|---|---|---|
| Reference device | ref | mPCCzPTzn-02 | 2.578 |
| Light-emitting device 1 (Comparative example) | 1 | 2mDBTBPDBq-II | 2.455 |

TABLE 2-continued

|  | | Host material | $T_{H(edge)}$ of host material [eV] |
|---|---|---|---|
| Light-emitting device 2 (Comparative example) | 2 | 2mPCCzPDBq-02 | 2.465 |
| Light-emitting device 3 (Comparative example) | 3 | mINc(II)PTzn | 2.684 |
| Light-emitting device 4 | 4 | 8βN-4mDBtPBfpm | 2.485 |
| Light-emitting device 5 | 5 | 8mDBtBPNfpm | 2.475 |
| Light-emitting device 6 (Comparative example) | 6 | 3,8mDBtP2Bfpr | 2.362 |
| Light-emitting device 7 (Comparative example) | 7 | 4,8mDBtP2Bfpm | 2.701 |

Next, the $T_{D(edge)}$ of the guest material ([Ir(ppy)$_2$(4dppy)]) used in the light-emitting layer of each of the light-emitting devices shown in Table 1 was obtained. The $T_{D(edge)}$ can be derived from the absorption edge of the absorption spectrum of [Ir(ppy)$_2$(4dppy)].

Figure 6:
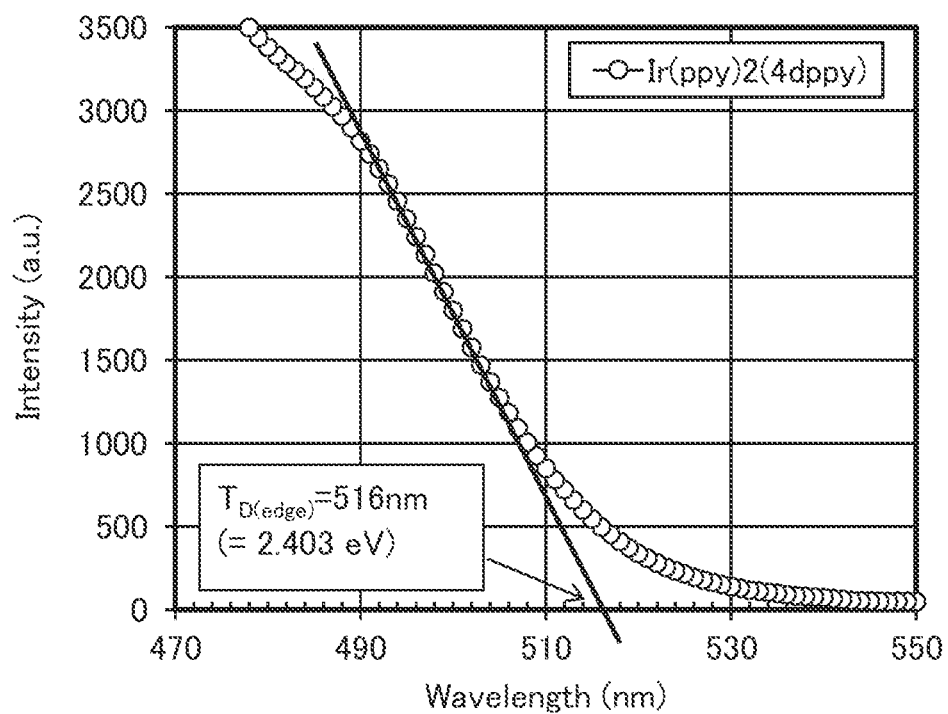
FIG. 6 shows a method for calculating $T_{D(edge)}$ from the phosphorescent spectrum.

The absorption edge of an absorption spectrum is the wavelength at the intersection of the horizontal axis and a tangent drawn to the curve on the longest wavelength side of the absorption spectrum at around the half of a peak or a shoulder peak on the longest wavelength side, and $T_{D(edge)}$ can be derived from this value. For example, the absorption edge of the absorption spectrum in FIG. 6 is the intersection (at 516 nm) of the horizontal axis and a tangent drawn to the curve at around the half of a shoulder peak (at around 490 nm) on the longest wavelength side. The $T_{D(edge)}$ of the guest material [Ir(ppy)$_2$(4dppy)] was calculated from the value to be 2.403 eV.

Then, the energy difference between the $T_{H(edge)}$ of the host material and the $T_{D(edge)}$ of the guest material ($T_{H(edge)}$-$T_{D(edge)}$) in each of the light-emitting devices was calculated. Table 3 lists the results.

TABLE 3

|  | | Host material | $T_{H(edge)}$-$T_{D(edge)}$ [eV]* |
|---|---|---|---|
| Reference device | ref | mPCCzPTzn-02 | 0.175 |
| Light-emitting device 1 (Comparative example) | 1 | 2mDBTBPDBq-II | 0.052 |
| Light-emitting device 2 (Comparative example) | 2 | 2mPCCzPDBq-02 | 0.062 |
| Light-emitting device 3 (Comparative example) | 3 | mINc(II)PTzn | 0.281 |
| Light-emitting device 4 | 4 | 8βN-4mDBtPBfpm | 0.082 |
| Light-emitting device 5 | 5 | 8mDBtBPNfpm | 0.072 |
| Light-emitting device 6 (Comparative example) | 6 | 3,8mDBtP2Bfpr | −0.041 |
| Light-emitting device 7 (Comparative example) | 7 | 4,8mDBtP2Bfpm | 0.298 |

*$T_{D(edge)}$ = 2.403 [eV] (absorption edge: 516 nm)

In addition, the external quantum efficiencies of the light-emitting devices were measured, and the normalized external quantum efficiencies were calculated from the measurement results with reference to the value of the reference device (see Table 4). As can be seen from FIG. 2, the normalized external quantum efficiencies were approximately the same regardless of the value of the energy difference between the $T_{H(edge)}$ of the host material and the $T_{D(edge)}$ of the guest material ($T_{H(edge)}$-$T_{D(edge)}$). In the light-emitting device 6, the value ($T_{H(edge)}$-$T_{D(edge)}$) is negative, which suggests endothermic triplet excitation energy transfer; however, this degree of difference does not influence the emission efficiency. That is, the level of the $T_{H(edge)}$ hardly influence emission efficiency. However, the present inventor has found that the level of the $T_{H(edge)}$ significantly affects the reliability.

Regarding the lifetimes of the light-emitting devices, time (LT70) until the luminance decays to 70% of the initial luminance was measured, and the normalized lifetimes were calculated from the measurement results with reference to the value of the reference device (see Table 4). The results are shown in FIG. 1.

TABLE 4

|  | | Host material | Normalized external quantum efficiency | Normalized lifetime (LT70) |
|---|---|---|---|---|
| Reference device | ref | mPCCzPTzn-02 | 1.000 | 1.000 |
| Light-emitting device 1 (Comparative example) | 1 | 2mDBTBPDBq-II | 1.012 | 0.555 |
| Light-emitting device 2 (Comparative example) | 2 | 2mPCCzPDBq-02 | 1.000 | 0.628 |
| Light-emitting device 3 (Comparative example) | 3 | mINc(II)PTzn | 1.029 | 1.026 |
| Light-emitting device 4 | 4 | 8βN-4mDBtPBfpm | 1.046 | 1.200 |
| Light-emitting device 5 | 5 | 8mDBtBPNfpm | 1.056 | 1.054 |
| Light-emitting device 6 (Comparative example) | 6 | 3,8mDBtP2Bfpr | 0.967 | 0.292 |
| Light-emitting device 7 (Comparative example) | 7 | 4,8mDBtP2Bfpm | 0.946 | 1.013 |

First, the light-emitting device 6 has high efficiency but has a noticeably short lifetime. This means that endothermic triplet excitation energy transfer leads to a certain degree of efficiency but significantly reduces a lifetime. What matter more are the behaviors of the light-emitting device 1 and the light-emitting device 2. In these devices, exothermic triplet excitation energy transfer should occur (i.e., the values ($T_{H(edge)}-T_{D(edge)}$) of the light-emitting devices 1 and 2 are positive); however, the lifetime is short. That is, this region is an exothermic energy transfer region, and the energy of a host material in the region is generally supposed to be sufficiently high (in terms of efficiency); however, the energy of the host material may be insufficient in terms of the lifetime. In contrast, the light-emitting device 4 and the light-emitting device 5 have a significantly improved lifetime longer than that of the reference device. Thus, a requirement of the present invention is that the value ($T_{H(edge)}-T_{D(edge)}$) needs not only to be 0 or more but also to exceed a certain positive value, to ensure a long lifetime. According to FIG. 1, it is necessary that the value ($T_{H(edge)}-T_{D(edge)}$) be 0.07 eV or more.

However, even when the value ($T_{H(edge)}-T_{D(edge)}$) was 0.07 eV or more, the lifetimes of the reference device, the light-emitting device 3, and the light-emitting device 7 were shorter than those of the light-emitting device 4 and the light-emitting device 5. Regarding these results, the upper limit of the value ($T_{H(edge)}-T_{D(edge)}$) and/or an influence of reverse intersystem crossing have to be taken into consideration. As described below, the reference device, the light-emitting device 3, and the light-emitting device 7 are influenced by reverse intersystem crossing; however, in the case where a decrease in lifetime is more influenced by the upper limit of the value ($T_{H(edge)}-T_{D(edge)}$) than by reverse intersystem crossing, the upper limit of the value ($T_{H(edge)}-T_{D(edge)}$) is preferably 0.17 eV (because the values ($T_{H(edge)}-T_{D(edge)}$) of the reference device, the light-emitting device 3, and the light-emitting device 7 were 0.175 eV, 0.281 eV, and 0.298 eV, respectively).

Next, an influence of reverse intersystem crossing will be described. In all the light-emitting devices fabricated in this example, the plurality of host materials (the first organic compound and the second organic compound) form an exciplex and energy is transferred to the guest material (phosphorescent substance), so that phosphorescence is emitted. In such light-emitting devices, as long as reverse intersystem crossing is unlikely to occur in a light-emitting layer, in principle, energy is transferred from 25% singlet excitons and 75% triplet excitons, which are generated by carrier recombination, to a guest (phosphorescent substance), and the same applies to the case where the first organic compound and the second organic compound do not form an exciplex; this is the point of the present invention.

However, in the case where the energy difference between the S1 level (the S1 level of an exciplex when the exciplex is formed) and $T_{H(edge)}$ of a host material is 0.2 eV or less, reverse intersystem crossing in the host material is dominant; thus, a path from the singlet excited state is dominant in energy transfer from the host material to the guest material. Such a state where energy is transferred dominantly from the singlet excited state is undesirable since in one embodiment of the present invention, an effect of the present invention can be obtained only after energy transfer from the triplet excited state becomes dominant.

That is, with not only the condition of the energy difference between the $T_{H(edge)}$ of a host material and the $T_{D(edge)}$ of a guest material ($T_{H(edge)}-T_{D(edge)}$) but also the above condition where reverse intersystem crossing does not occur, in other words, in the case where energy is transferred from generated 75% triplet excitons to the guest material, an effect of the present invention is obtained. The normalized lifetimes of the reference device, the light-emitting device 3, and the light-emitting device 7 among the light-emitting devices fabricated in this example are shorter than those of the light-emitting device 4 and the light-emitting device 5, according to the results shown in FIG. 1. The conditions under which reverse intersystem crossing occurs in the host materials of the reference device, the light-emitting device 3, and the light-emitting device 7 will be described below.

First, the S1 level of a mixed material of mINc(II)PTzn and PCCP (an exciplex when the exciplex is formed) in the light-emitting layer of the light-emitting device 3 was derived from an emission edge on the short wavelength side of the fluorescent spectrum of the mixed material, as the $S'_{H(edge)}$ of the mixed material.

Figure 7:
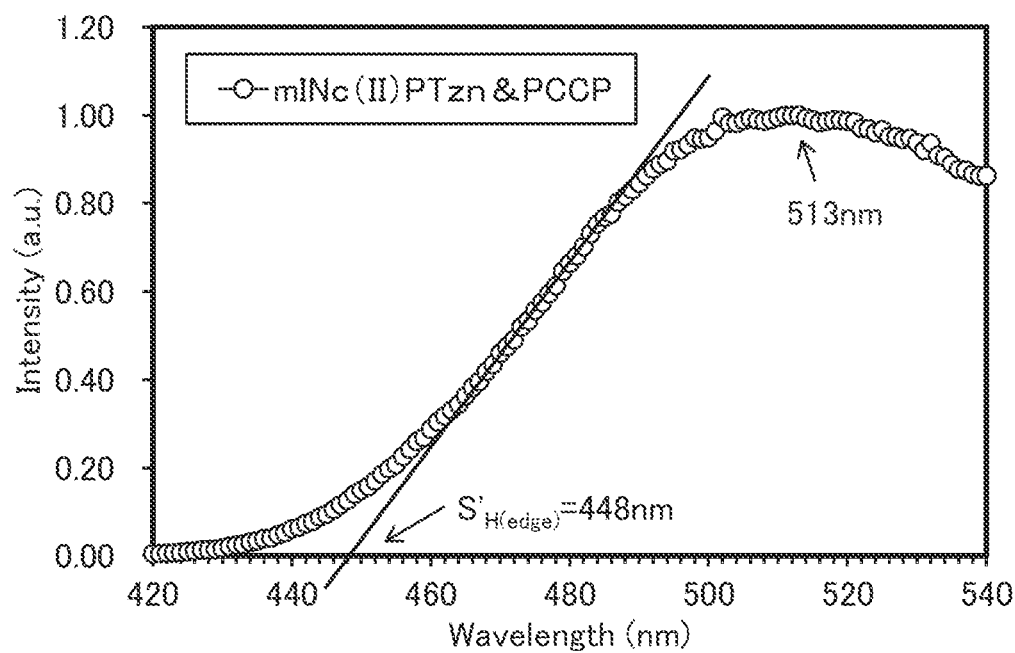
FIG. 7 shows a method for calculating $S'_{H(edge)} - T_{H(edge)}$ from the absorption spectrum.

The emission edge of a fluorescent spectrum is the wavelength at the intersection of the horizontal axis and a tangent drawn to the curve on the short wavelength side at around the half of a peak on the shortest wavelength side, and $S'_{H(edge)}$ can be derived from this value. For example, the emission edge of the fluorescent spectrum in FIG. 7 is the intersection (at 448 nm) of the horizontal axis and a tangent drawn to the curve at around the half of a peak (at 513 nm) on the shortest wavelength side. The $S'_{H(edge)}$ of the substance having the fluorescent spectrum in FIG. 7 was calculated from the value to be 2.768 eV. Thus, $\Delta E_{S't}=S'_{H(edge)}-T_{H(edge)}$ was calculated to be 0.084 eV. Similarly, $\Delta E_{S't}$ of the reference device was calculated to be 0.171 eV.

Table 5 lists the values ($T_{H(edge)}-T_{D(edge)}$) and $\Delta E_{S't}(=S'_{H(edge)}-T_{H(edge)})$ of the reference device, the light-emitting devices 3 to 5, and the light-emitting device 7 whose value ($T_{H(edge)}-T_{D(edge)}$) is 0.07 eV or more.

TABLE 5

| | Host material | $T_{H(edge)}$ [eV] | $T_{H(edge)}-T_{D(edge)}$ [eV]* | $S'_{H(edge)}$ [eV] | $S'_{H(edge)}-T_{H(edge)}$ [eV] |
|---|---|---|---|---|---|
| Reference device | mPCCzPTzn-02 | 2.578 | 0.175 | 2.749 | 0.171 |
| Light-emitting device 3 (Comparative example) | mINc(II)PTzn | 2.684 | 0.281 | 2.768 | 0.084 |
| Light-emitting device 4 | 8βN-4mDBtPBfpm | 2.485 | 0.082 | 2.786 | 0.301 |
| Light-emitting device 5 | 8mDBtBPNfpm | 2.475 | 0.072 | 2.792 | 0.317 |
| Light-emitting device 7 (Comparative example) | 4,8mDBtP2Bfpm | 2.701 | 0.298 | 2.831 | 0.130 |

*$T_{D(edge)}$ = 2.403 [eV] (Absorption edge: 516 nm)

The reference device satisfies the condition where the value ($T_{H(edge)}-T_{D(edge)}$) is greater than or equal to 0.07 eV and less than or equal to 0.27 eV but has $\Delta E_{s't}$ of less than 0.2 eV, which is a condition under which reverse intersystem crossing occurs. The value ($T_{H(edge)}-T_{D(edge)}$) of the reference device is out of the range from 0.07 eV to 0.17 eV. The light-emitting device 3 and the light-emitting device 7 do not satisfy the condition where the value ($T_{H(edge)}-T_{D(edge)}$) is greater than or equal to 0.07 eV and less than or equal to 0.27 eV and have $\Delta E_{s't}$ of less than 0.2 eV. Thus, these devices have a shorter lifetime than the light-emitting devices 4 and 5.

In contrast, the light-emitting devices 4 and 5 satisfy the condition where the value ($T_{H(edge)}-T_{D(edge)}$) is greater than or equal to 0.07 eV and less than or equal to 0.27 eV and have $\Delta E_{s't}$ of 0.3-plus eV, which means that reverse intersystem crossing is not dominant. Consequently, the light-emitting devices 4 and 5 have the longest lifetime in this example. These devices also satisfy the condition where the value ($T_{H(edge)}-T_{D(edge)}$) is greater than or equal to 0.07 eV and less than or equal to 0.17 eV.

Note that when $\Delta E_{s't}$ is too large, excitation energy is excessively higher than that of a guest material, which results in easy deterioration due to a singlet excited state. Therefore, $\Delta E_{s't}$ is preferably 0.5 eV or less.

The above results of this example reveal that the light-emitting device of one embodiment of the present invention can have a long lifetime when the energy difference between the $T_{H(edge)}$ of a host material and the $T_{D(edge)}$ of a guest material ($T_{H(edge)}-T_{D(edge)}$) is greater than or equal to 0.07 eV and less than or equal to 0.27 eV, preferably greater than or equal to 0.07 eV and less than or equal to 0.17 eV and the energy difference between the $S'_{H(edge)}$ and the $T_{H(edge)}$ of the host material ($S'_{H(edge)}-T_{H(edge)}$) is greater than or equal to 0.2 eV and less than or equal to 0.5 eV.

Note that the above conditions can be expressed by Formula 1 and Formula 2 below. Note that in the case where the upper limit of the value ($T_{H(edge)}-T_{D(edge)}$) is emphasized, the condition of Formula (3) is more favorable than the condition of Formula (1).

[Formulae 6]

$$0.07 \text{ eV} \leq T_{H(edge)}-T_{D(edge)} \leq 0.27 \text{ eV} \tag{1}$$

$$0.02 \text{ eV} \leq S'_{H(edge)}-T_{H(edge)} \leq 0.5 \text{ eV} \tag{2}$$

$$0.07 \text{ eV} \leq T_{H(edge)}-T_{D(edge)} \leq 0.17 \text{ eV} \tag{3}$$

Note that the fabrication methods and device characteristics of the reference device and the light-emitting devices 1 to 7 used in this example will be described in Example 2.

Example 2

In this example, a plurality of light-emitting devices (the light-emitting devices 1 to 7) including EL layers 902 with different layered structures were fabricated, and the device characteristics thereof will be described. In addition, a plurality of comparative light-emitting devices (comparative light-emitting devices a1 to a5) including a light-emitting layer 913 containing at least 9-[3-(4,6-diphenyl-1,3,5-triazin-2-yl)phenyl]-9'-phenyl-2,3'-bi-9H-carbazole (abbreviation: mPCCzPTzn-02) were fabricated and compared with the light-emitting devices 1 to 7. Note that all the light-emitting devices (the light-emitting devices 1 to 7 and the comparative light-emitting devices a1 to a5) used the same light-emitting substance (bis[2-(2-pyridinyl-κN)phenyl-κC] [2-(4-phenyl-2-pyridinyl-κN)phenyl-κC]iridium(III) (abbreviation: [Ir(ppy)$_2$(4dppy)])) in the light-emitting layer 913.

Figure 15:
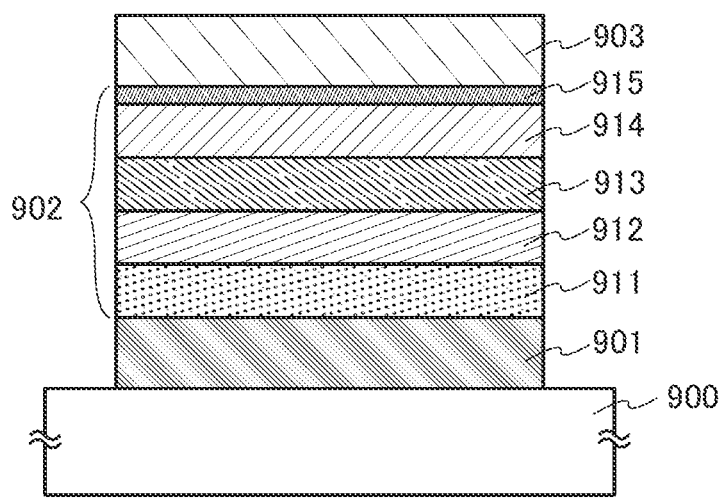
FIG. 15 illustrates a light-emitting device.

Specific device structures and fabrication methods of the above light-emitting devices will be described below. The device structure of the light-emitting devices described in this example is illustrated in FIG. 15. The chemical formulae of materials used in this example are shown below. Note that numbers given to the abbreviation of chemical formulae are the same as those in Example 1.

[Chemical Formula 3]

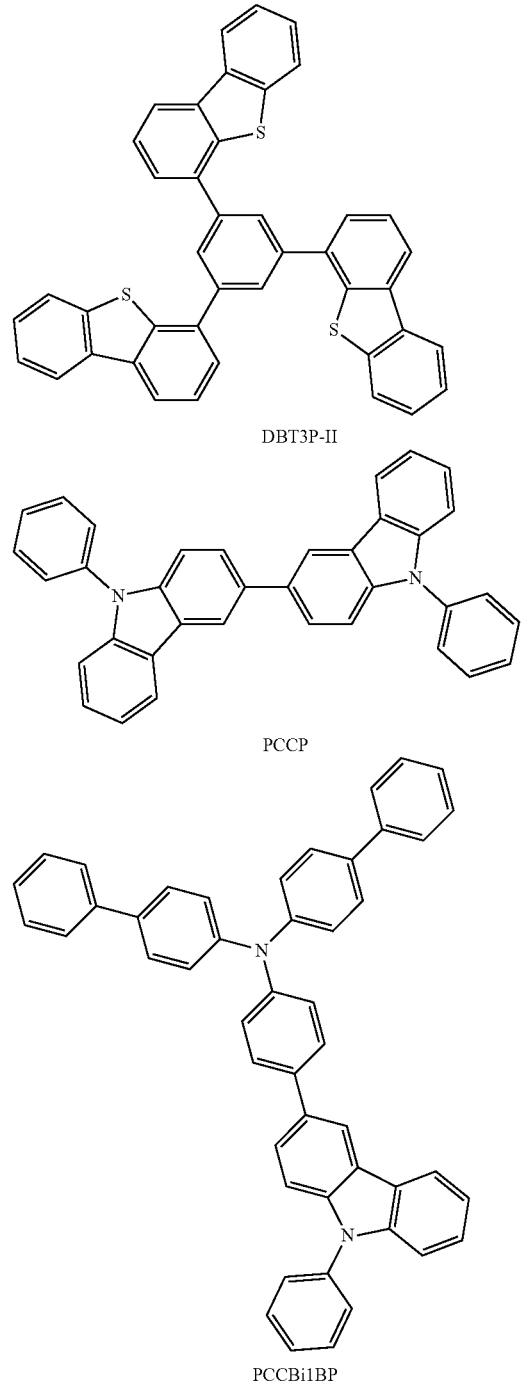

DBT3P-II

PCCP

PCCBi1BP

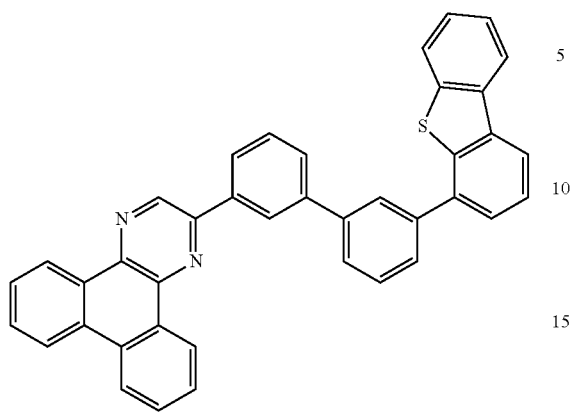
2mDBtBPDBq-II
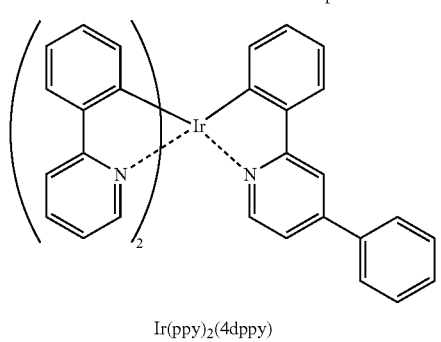
Ir(ppy)₂(4dppy)
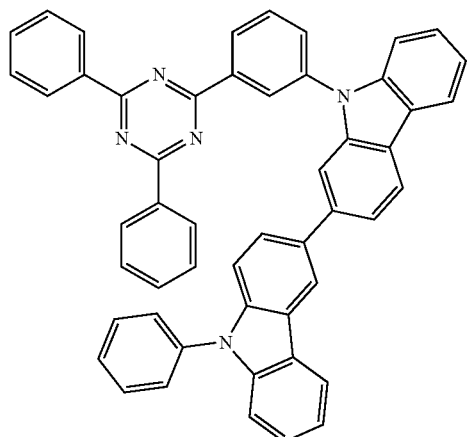
mPCCzPTzn-02
(ref.)
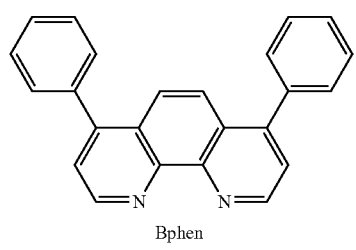
Bphen
[Chemical Formula 4]
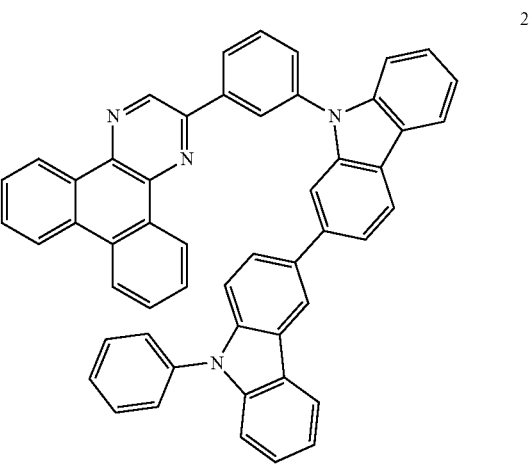
2mPCCzPDBq-02
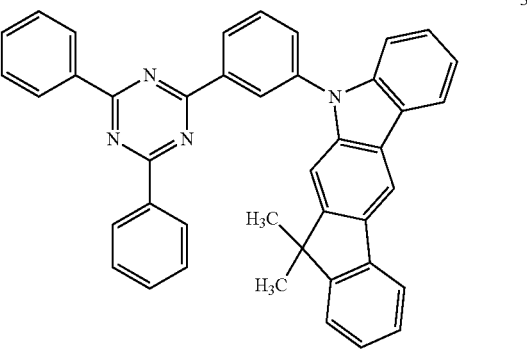
m1Nc(1l)PTzn
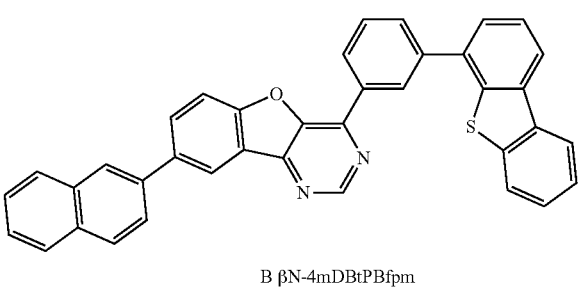
B βN-4mDBtPBfpm
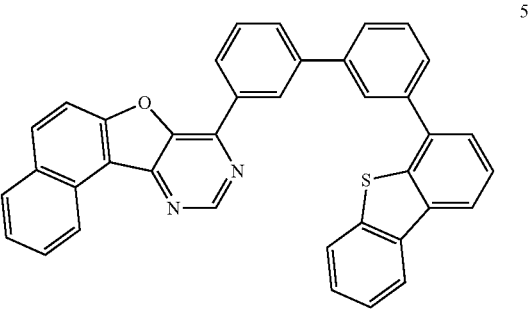
8mDBtBPNfpm

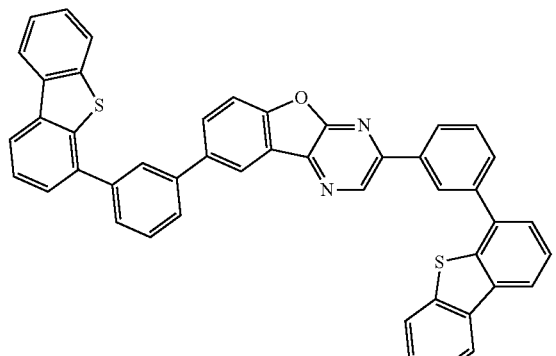

3,8mDPtP2Bfpr

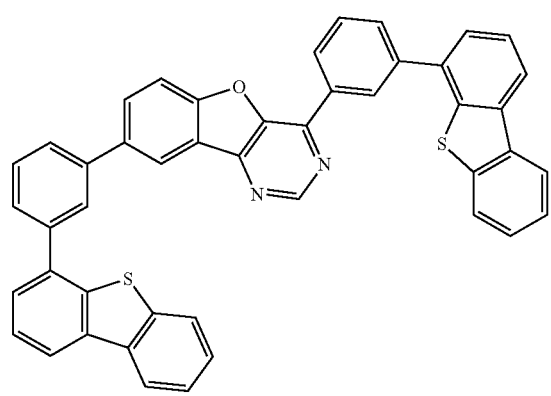

4,8mDBtP2Bfpm

First, fabrication methods of the light-emitting device 1 and the comparative light-emitting device a1 among the light-emitting devices fabricated in this example will be described. The specific structures of the light-emitting devices are shown in Table 6 below.

<<Fabrication of Light-Emitting Devices>>

<Fabrication of Light-Emitting Device 1 and Comparative Light-Emitting Device a1>

In each of the light-emitting devices described in this example, as illustrated in FIG. 15, a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

First, the first electrode 901 was formed over the substrate 900. The electrode area was set to 4 mm$^2$ (2 mm×2 mm). A glass substrate was used as the substrate 900. The first electrode 901 was formed to a thickness of 70 nm using indium tin oxide containing silicon oxide (ITSO) by a sputtering method.

For pretreatment, a surface of the substrate was washed with water, baking was performed at 200° C. for 1 hour, and then UV ozone treatment was performed for 370 seconds. After that, the substrate was transferred into a vacuum evaporation apparatus where the pressure had been reduced to approximately 1×10$^{-4}$ Pa, and was subjected to vacuum baking at 170° C. for 30 minutes in a heating chamber of the vacuum evaporation apparatus, and then the substrate was cooled down for approximately 30 minutes.

Next, the hole-injection layer 911 was formed over the first electrode 901. After the pressure in the vacuum evaporation apparatus was reduced to 1×10$^{-4}$ Pa, the hole-injection layer 911 was formed by co-evaporation to have a mass ratio of DBT3P-II to molybdenum oxide of 2:1 and a thickness of 50 nm.

Then, the hole-transport layer 912 was formed over the hole-injection layer 911. The hole-transport layer 912 was formed to a thickness of 20 nm by evaporation of PCBBi1BP.

Next, the light-emitting layer 913 was formed over the hole-transport layer 912.

The light-emitting layer 913 of the light-emitting device 1 was formed by co-evaporation using 2-[3'-(dibenzothiophen-4-yl)biphenyl-3-yl]dibenzo[f,h]quinoxaline (abbreviation: 2mDBTBPDBq-II) and 3,3'-bis(9-phenyl-9H-carbazole) (abbreviation: PCCP) and using [2-(4-phenyl-2-pyridinyl-κN)phenyl-κC]bis[2-(2-pyridinyl-κN)phenyl-κC]iridium(III) (abbreviation: [Ir(ppy)$_2$(4dppy)]) as a guest material (phosphorescent substance) to have a weight ratio of mlNc(II)PTzn: PCCP: [Ir(ppy)$_2$(4dppy)]=0.6:0.4:0.1. The thickness was set to 40 nm.

The light-emitting layer 913 of the comparative light-emitting device a1 was formed by co-evaporation using

TABLE 6

| | First electrode | Hole-injection layer | Hole-transport layer | Light-emitting layer | Electron-transport layer | | Electron-injection layer | Second electrode |
|---|---|---|---|---|---|---|---|---|
| Light-emitting device 1 | ITSO (70 nm) | DBT3P-II:MoOx (2:1 50 nm) | PCBBi1BP (20 nm) | * | 2mDBTBPDBq-II (20 nm) | Bphen (15 nm) | LiF (1 nm) | Al (200 nm) |
| Comparative light-emitting device a1 | ITSO (70 nm) | DBT3P-II:MoOx (2:1 50 nm) | PCBBi1BP (20 nm) | ** | mPCCzPTzn-02 (20 nm) | Bphen (15 nm) | LiF (1 nm) | Al (200 nm) |

* 2mDBTBPDBq-II:PCCP:[Ir(ppy)$_2$(4dppy)] (0.6:0.4:0.1 40 nm)
** mPCCzPTzn-02:PCCP:[Ir(ppy)$_2$(4dppy)] (0.6:0.4:0.1 40 nm)

9-[3-(4,6-diphenyl-1,3,5-triazin-2-yl)phenyl]-9'-phenyl-2,3'-bi-9H-carbazole (abbreviation: mPCCzPTzn-02) and PCCP and using [Ir(ppy)$_2$(4dppy)]) as a guest material (phosphorescent substance) to have a weight ratio of mPCCzPTzn-02: PCCP: [Ir(ppy)$_2$(4dppy)]=0.6:0.4:0.1. The thickness was set to 40 nm.

Next, the electron-transport layer 914 was formed over the light-emitting layer 913.

The electron-transport layer 914 of the light-emitting device 1 was formed in such a manner that 2mDBTBPDBq-II and Bphen were sequentially deposited by evaporation to thicknesses of 20 nm and 15 nm, respectively. The electron-transport layer 914 of the comparative light emitting device a1 was formed in such a manner that mPCCzPTzn-02 and Bphen were sequentially deposited by evaporation to thicknesses of 20 nm and 15 nm, respectively.

Then, the electron-injection layer 915 was formed over the electron-transport layer 914. The electron-injection layer 915 was formed to a thickness of 1 nm by evaporation of lithium fluoride (LiF).

atmosphere, and the substrates were bonded to each other such that the sealant was attached so as to surround the light-emitting device formed over the substrate 900. In the sealing process, the sealant was irradiated with 365-nm ultraviolet light at 6 J/cm$^2$ to be cured, and the sealant was heated at 80° C. for 1 hour to be stabilized.

<<Operation Characteristics 1 of Light-Emitting Devices>>

Figure 16:
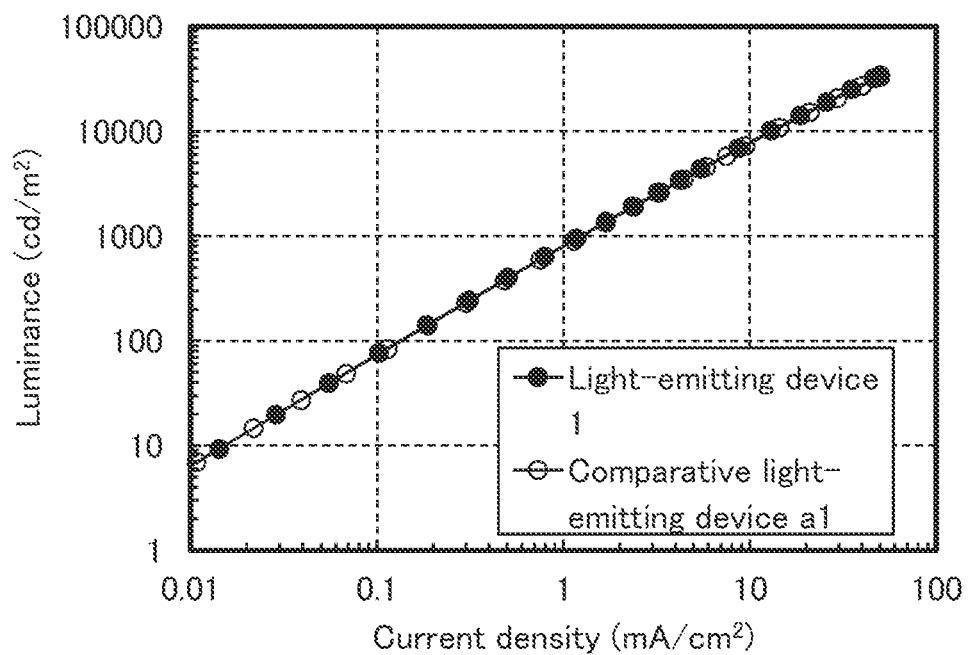
FIG. 16 is a graph showing the luminance-current density characteristics of a light-emitting device 1 and a comparative light-emitting device a1.
Figure 17:
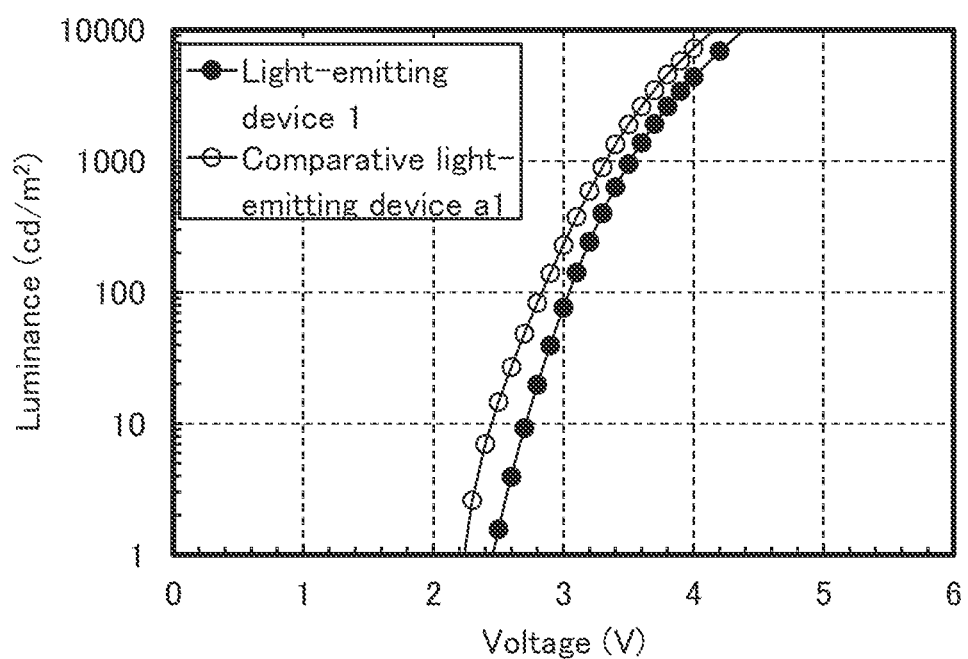
FIG. 17 is a graph showing the luminance-voltage characteristics of the light-emitting device 1 and the comparative light-emitting device a1.
Figure 18:
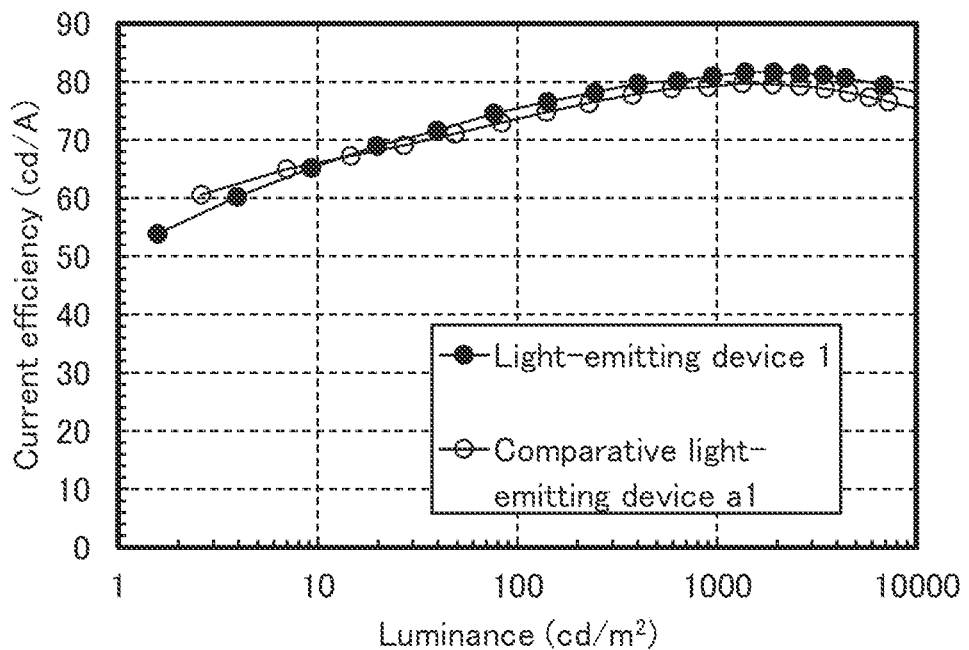
FIG. 18 is a graph showing the current efficiency-luminance characteristics of the light-emitting device 1 and the comparative light-emitting device a1.
Figure 19:
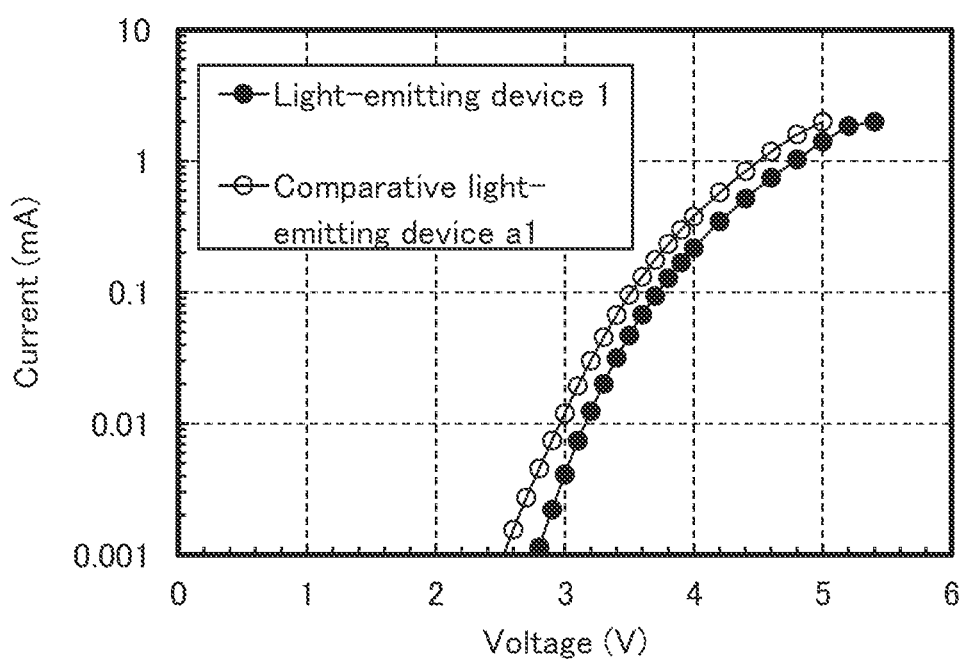
FIG. 19 is a graph showing the current-voltage characteristics of the light-emitting device 1 and the comparative light-emitting device a1.

Operation characteristics of the fabricated light-emitting devices were measured. Note that the measurement was performed at room temperature (in an atmosphere kept at 25° C.). As the results of the operation characteristics of the light-emitting device 1 and the comparative light-emitting device a1, the current density-luminance characteristics are shown in FIG. 16, the voltage-luminance characteristics are shown in FIG. 17, the luminance-current efficiency characteristics are shown in FIG. 18, and the voltage-current characteristics are shown in FIG. 19.

Table 7 shows the initial values of main characteristics of the light-emitting devices at around 1000 cd/m$^2$.

TABLE 7

| | Voltage (V) | Current (mA) | Current density (mA/cm$^2$) | Chromaticity (x, y) | Luminance (cd/m$^2$) | Current efficiency (cd/A) | Power efficiency (lm/W) | External quantunm efficiency (%) |
|---|---|---|---|---|---|---|---|---|
| Light-emitting device 1 | 3.5 | 0.047 | 1.2 | (0.45, 0.54) | 950 | 81 | 73 | 24 |
| Comparative light-emitting device a1 | 3.3 | 0.045 | 1.1 | (0.45, 0.54) | 900 | 79 | 75 | 24 |

After that, the second electrode 903 was formed over the electron-injection layer 915. The second electrode 903 was formed to a thickness of 200 nm by an evaporation method using aluminum. In this example, the second electrode 903 functions as a cathode.

Through the above steps, the light-emitting devices each including the EL layer between the pair of electrodes were formed over the substrate 900. Note that the hole-injection layer 911, the hole-transport layer 912, the light-emitting layer 913, the electron-transport layer 914, and the electron-injection layer 915 described above are functional layers forming the EL layer in one embodiment of the present invention. Furthermore, in all the evaporation steps in the above fabrication method, evaporation was performed by a resistance-heating method.

Figure 20:
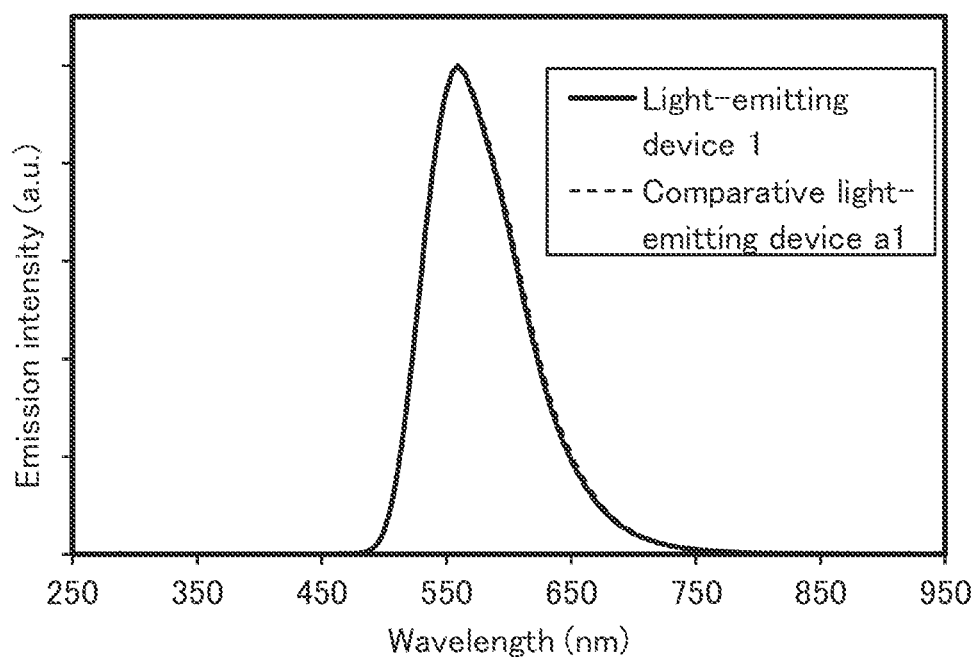
FIG. 20 shows the emission spectra of the light-emitting device 1 and the comparative light-emitting device a1.

Each of the light-emitting devices fabricated as described above was sealed using another substrate (not illustrated) in such a manner that the substrate (not illustrated) to which a sealant to be cured by ultraviolet light was applied was fixed to the substrate 900 in a glove box containing a nitrogen FIG. 20 shows emission spectra when a current at a current density of 2.5 mA/cm$^2$ was supplied to the light-emitting devices. As shown in FIG. 20, the emission spectrum of each light-emitting device has a peak at around 561 nm, which is presumably derived from light emission of [Ir(ppy)$_2$(4dppy)] contained in the light-emitting layer 913.

Figure 21:
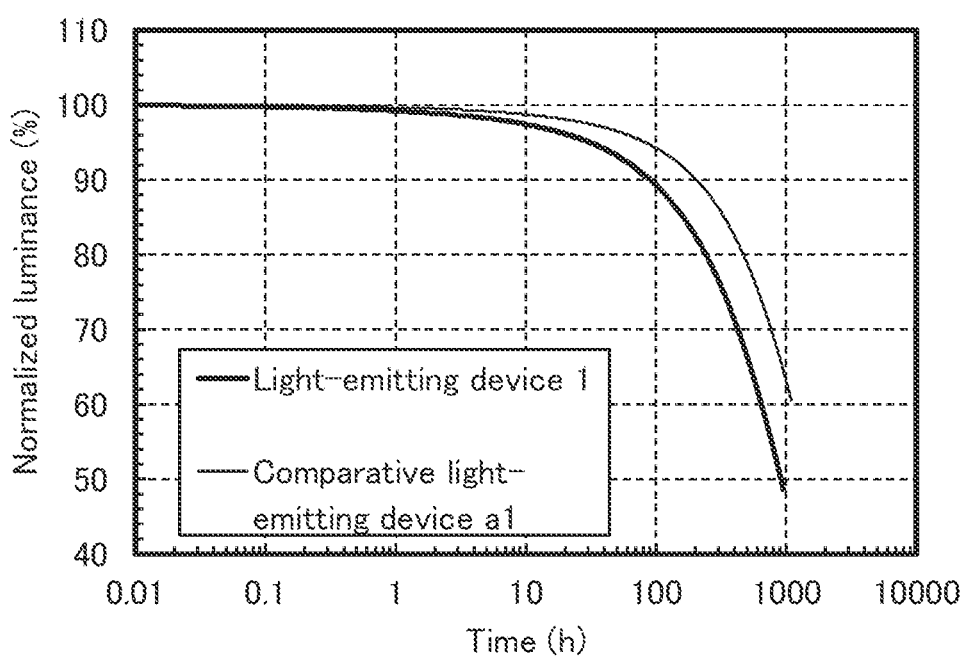
FIG. 21 is a graph showing the reliabilities of the light-emitting device 1 and the comparative light-emitting device a1.
Figure 22:
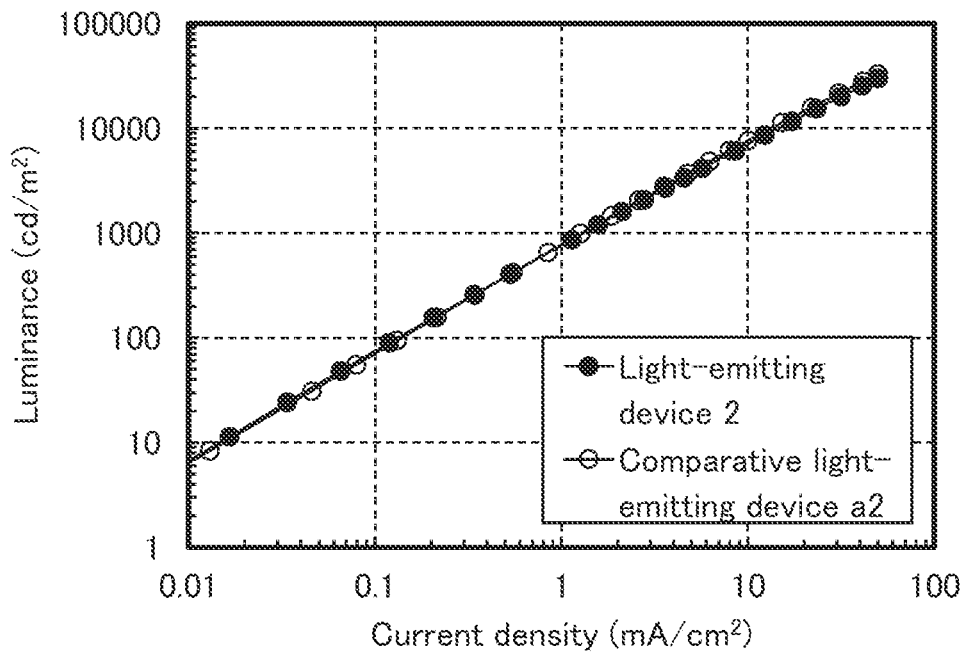
FIG. 22 is a graph showing the luminance-current density characteristics of a light-emitting device 2 and a comparative light-emitting device a2.
Figure 23:
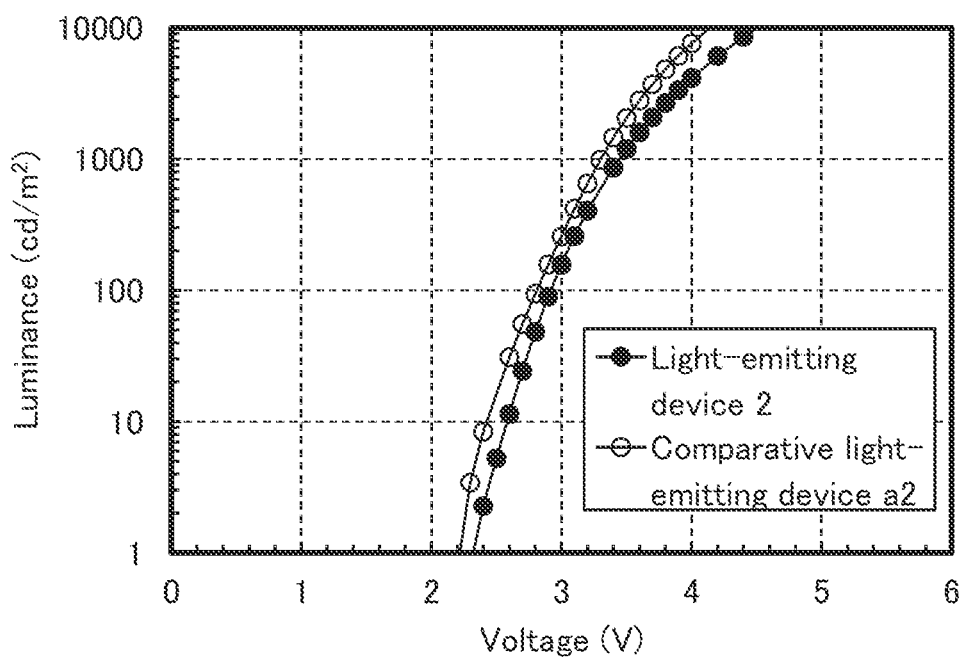
FIG. 23 is a graph showing the luminance-voltage characteristics of the light-emitting device 2 and the comparative light-emitting device a2.
Figure 24:
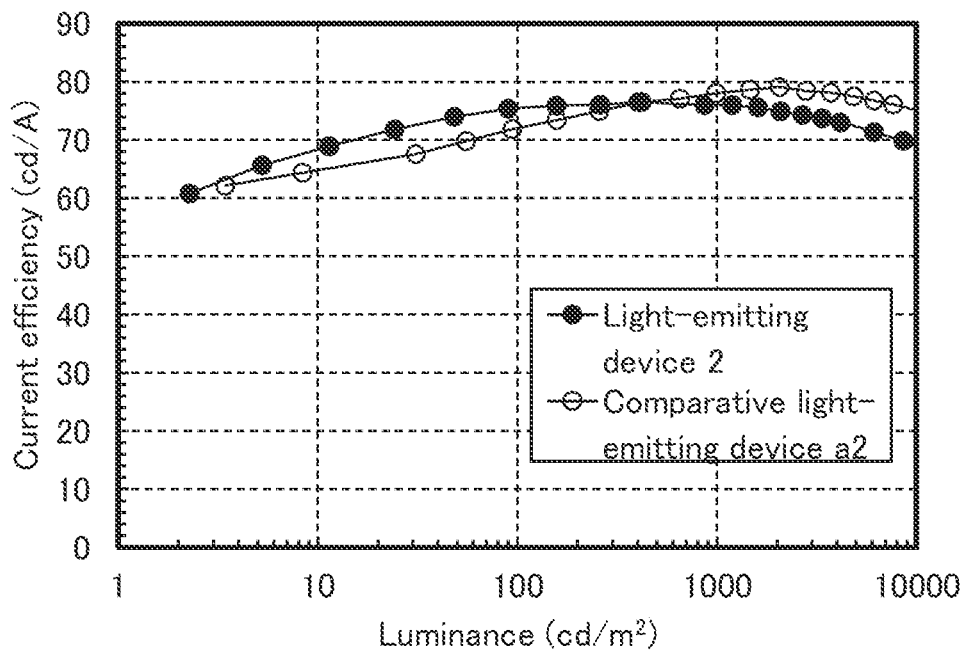
FIG. 24 is a graph showing the current efficiency-luminance characteristics of the light-emitting device 2 and the comparative light-emitting device a2.
Figure 25:
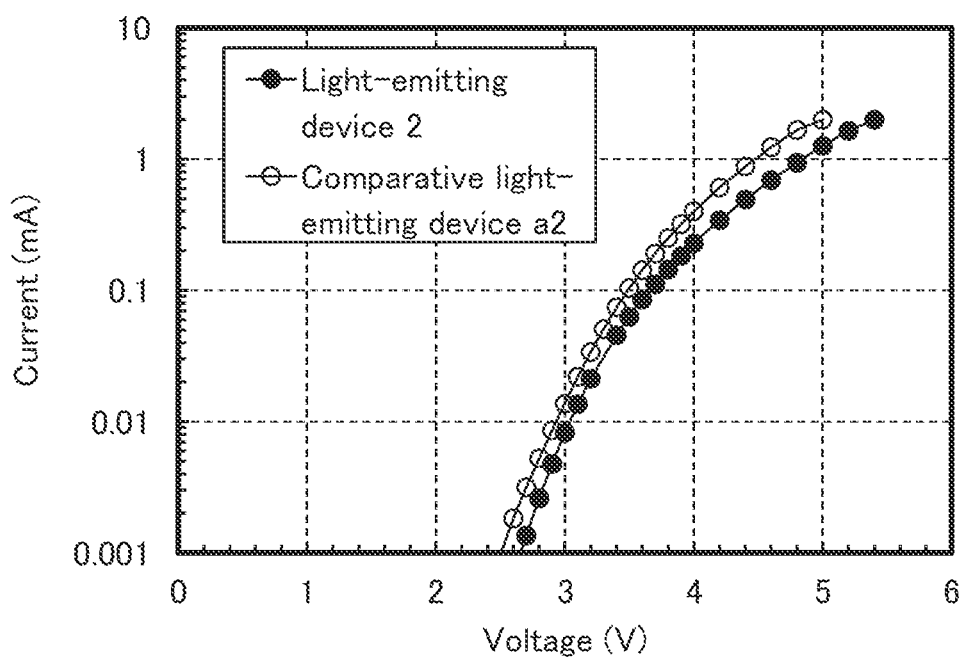
FIG. 25 is a graph showing the current-voltage characteristics of the light-emitting device 2 and the comparative light-emitting device a2.

Next, reliability tests were performed on the light-emitting devices. FIG. 21 shows results of the reliability tests. In FIG. 21, the vertical axis represents normalized luminance (%) with an initial luminance of 100%, and the horizontal axis represents driving time (h) of the devices. Note that in the reliability tests, the light-emitting devices were driven at a constant current of 2 mA.

Next, light-emitting devices (the light-emitting device 2 and the comparative light-emitting device a2) having structures different from those of the above light-emitting devices will be described. These light-emitting devices can be fabricated by a method similar to those of the above light-emitting devices. The specific structures are shown in Table 8 below.

TABLE 8

| | First electrode | Hole-injection layer | Hole-transport layer | Light-emitting layer | Electron-transport layer | | Electron-injection layer | Second electrode |
|---|---|---|---|---|---|---|---|---|
| Light-emitting device 2 | ITSO (70 nm) | DBT3P-II: MoOx (2:1 50 nm) | PCBBiIBP (20 nm) | * | 2mPCCzPDBq-02 (20 nm) | Bphen (15 nm) | LiF (1 nm) | Al (200 nm) |

TABLE 8-continued

|  | First electrode | Hole-injection layer | Hole-transport layer | Light-emitting layer | Electron-transport layer | | Electron-injection layer | Second electrode |
| --- | --- | --- | --- | --- | --- | --- | --- | --- |
| Comparative light-emitting device a2 | ITSO (70 nm) | DBT3P-II: MoOx (2:1 50 nm) | PCBBiIBP (20 nm) | ** | mPCCzPTzn-02 (20 nm) | Bphen (15 nm) | LiF (1 nm) | Al (200 nm) |

\* 2mPCCzPDBq-02:PCCP:[Ir(ppy)$_2$(4dPPY)] (0.8:0.2:0.1 40 nm)
\*\* mPCCzPTzn-02:PCCP:[Ir(PPY)$_2$(4dPPY)] (0.6:0.4:0.1 40 nm)

Note that 2mPCCzPDBq-02 in Table 8 is an abbreviation for 2-{3-[2-(N-phenyl-9H-carbazol-3-yl)-9H-carbazol-9-yl]phenyl}dibenzo[f,h]quinoxaline.

<<Operation Characteristics 2 of Light-Emitting Devices>>

The operation characteristics of the fabricated light-emitting device 2 and comparative light-emitting device a2 were measured at room temperature. The results are shown in FIG. 22 to FIG. 25.

Table 9 shows the initial values of main characteristics of the light-emitting devices at around 1000 cd/m$^2$.

Figure 27:
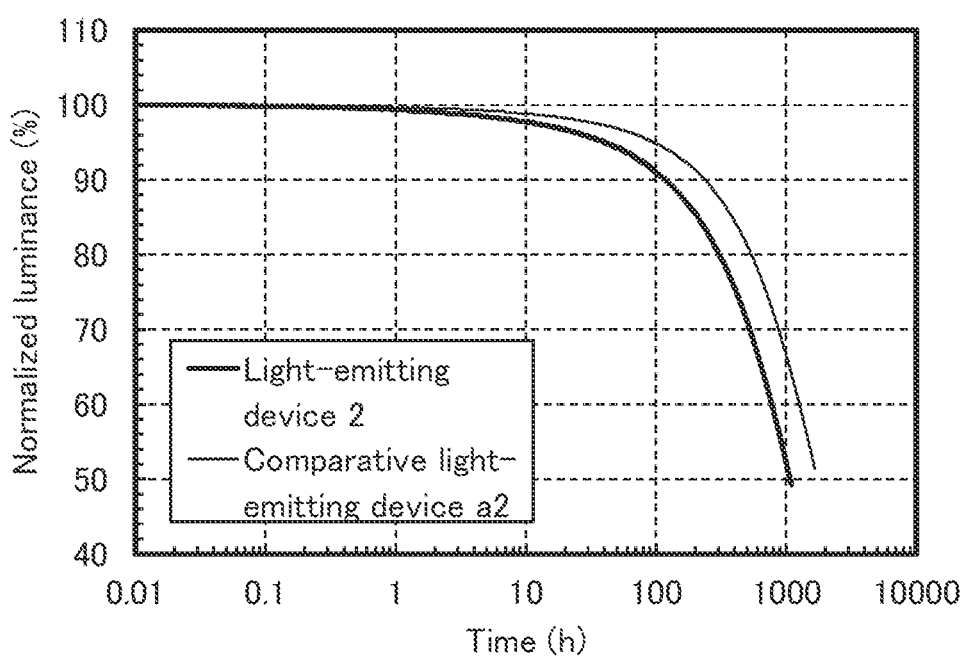
FIG. 27 is a graph showing the reliabilities of the light-emitting device 2 and the comparative light-emitting device a2.
Figure 28:
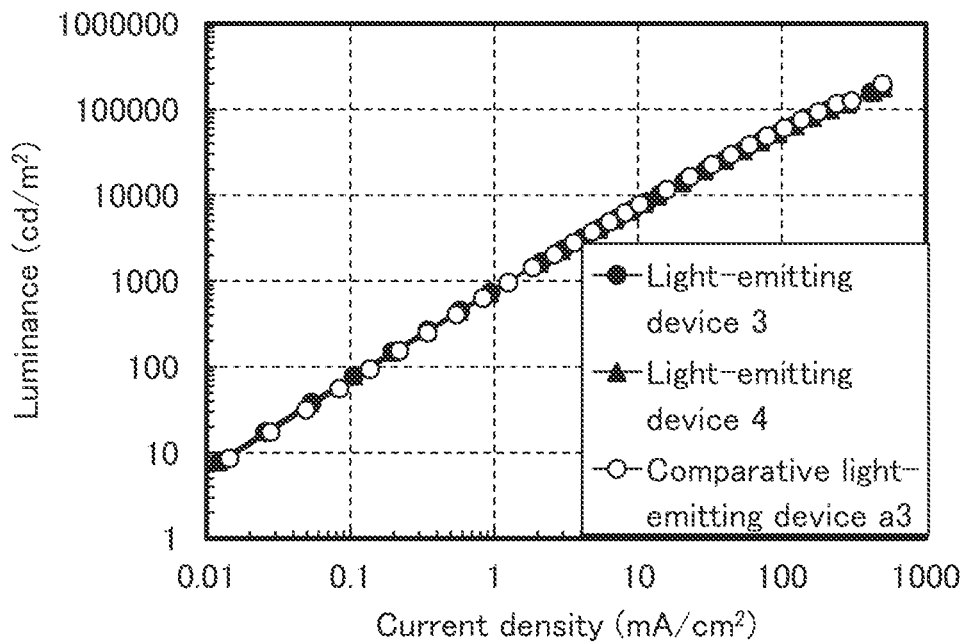
FIG. 28 is a graph showing the luminance-current density characteristics of a light-emitting device 3, a light-emitting device 4, and a comparative light-emitting device a3.
Figure 29:
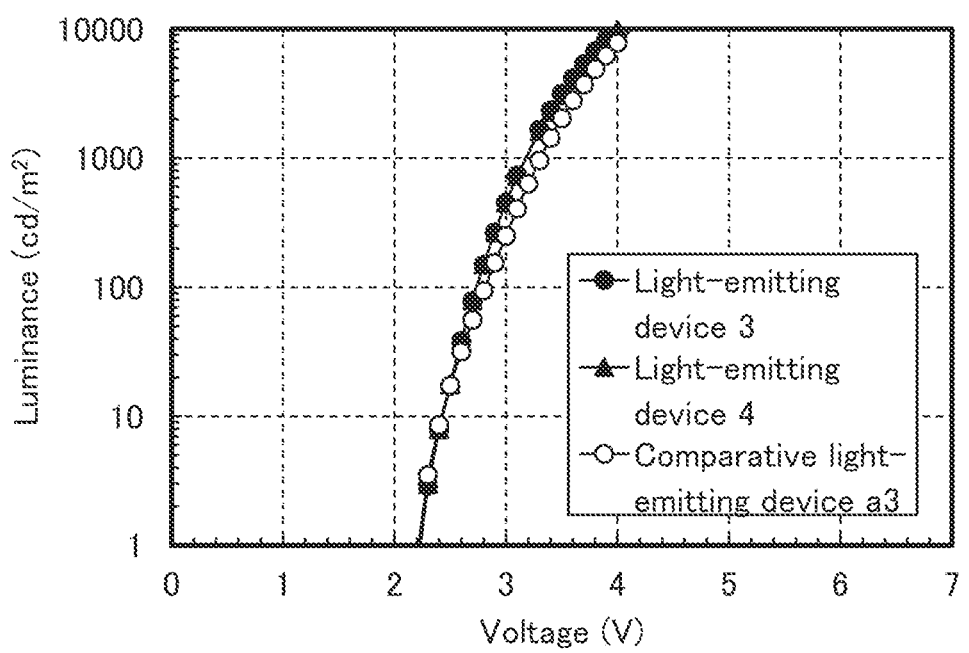
FIG. 29 is a graph showing the luminance-voltage characteristics of the light-emitting device 3, the light-emitting device 4, and the comparative light-emitting device a3.
Figure 30:
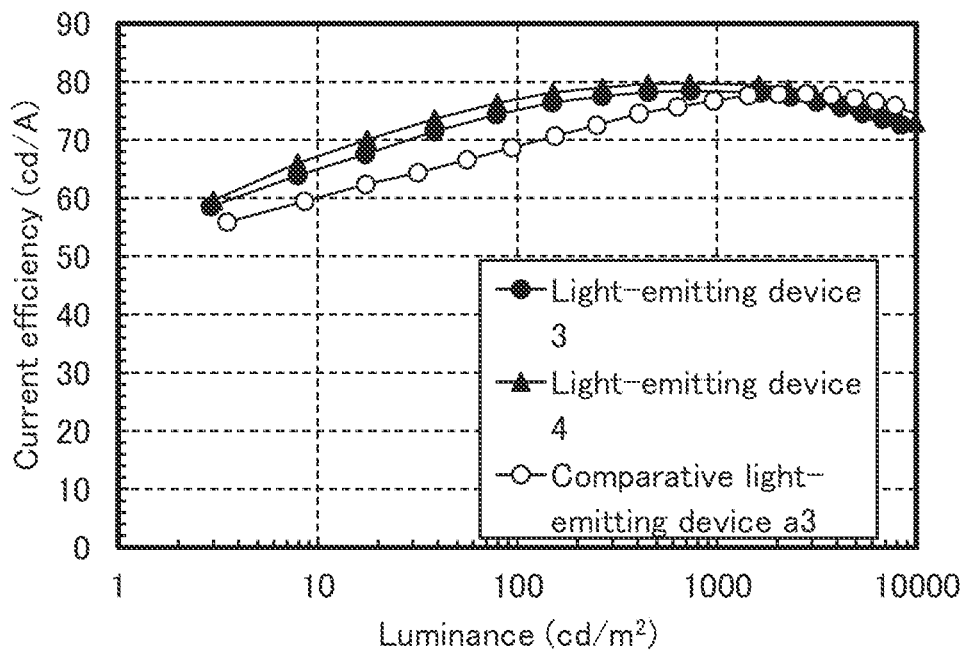
FIG. 30 is a graph showing the current efficiency-luminance characteristics of the light-emitting device 3, the light-emitting device 4, and the comparative light-emitting device a3.
Figure 31:
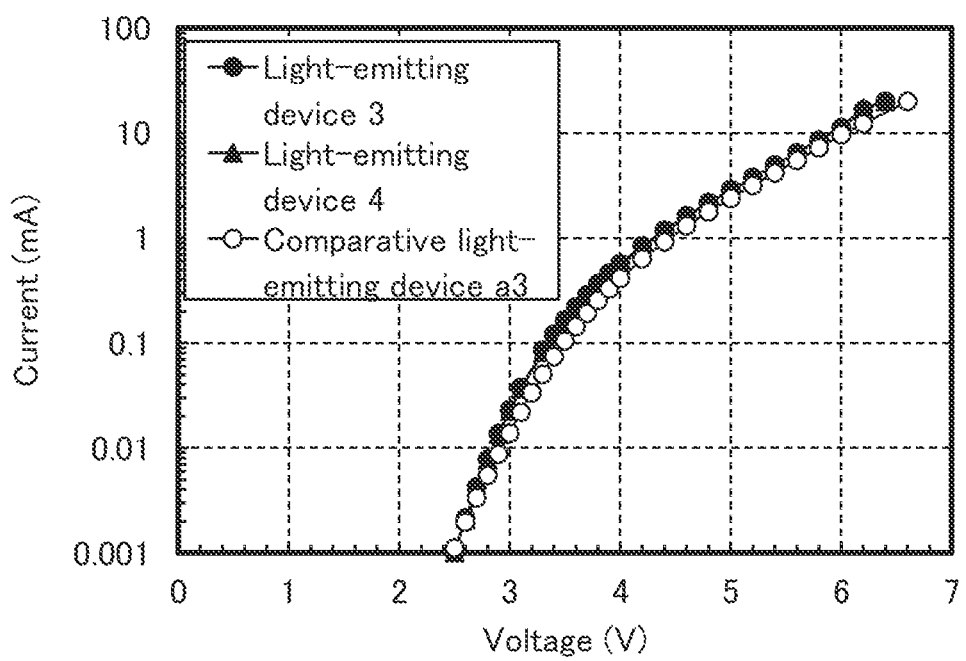
FIG. 31 is a graph showing the current-voltage characteristics of the light-emitting device 3, the light-emitting device 4, and the comparative light-emitting device a3.

Next, reliability tests were performed on the light-emitting devices. FIG. 27 shows results of the reliability tests. In FIG. 27, the vertical axis represents normalized luminance (%) with an initial luminance of 100%, and the horizontal axis represents driving time (h) of the devices. Note that in the reliability tests, the light-emitting devices were driven at a constant current of 2 mA.

TABLE 9

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
| --- | --- | --- | --- | --- | --- | --- | --- | --- |
| Light-emitting device 2 | 3.4 | 0.045 | 1.1 | (0.47, 0.53) | 860 | 76 | 70 | 24 |
| Comparative light-emitting device a2 | 3.3 | 0.051 | 1.3 | (0.46, 0.53) | 990 | 78 | 74 | 24 |

Figure 26:
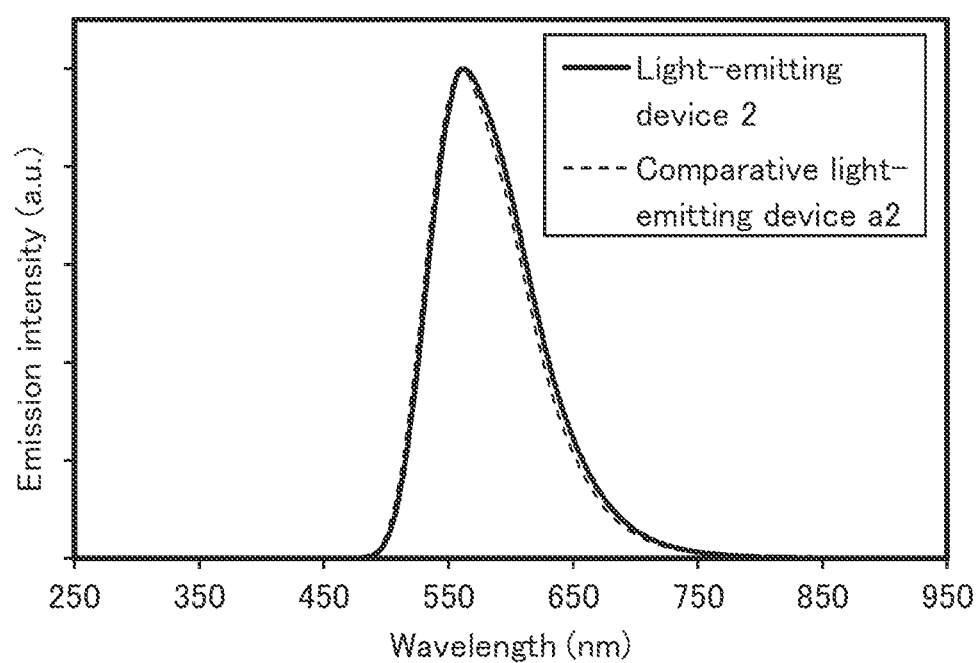
FIG. 26 shows the emission spectra of the light-emitting device 2 and the comparative light-emitting device a2.

FIG. 26 shows emission spectra when current at a current density of 2.5 mA/cm$^2$ was supplied to the light-emitting devices. As shown in FIG. 26, the emission spectrum of each light-emitting device has a peak at around 560 nm, which is presumably derived from light emission of [Ir(ppy)$_2$(4dppy)] contained in the light-emitting layer 913.

Next, light-emitting devices (the light-emitting device 3, the light-emitting device 4, and the comparative light-emitting device a3) having structures different from those of the above light-emitting devices will be described. These light-emitting devices can be fabricated by a method similar to those of the above light-emitting devices. The specific structures are shown in Table 10 below.

TABLE 10

|  | First electrode | Hole-injection layer | Hole-transport layer | Light-emitting layer | Electron-transport layer | | Electron-injection layer | Second electrode |
| --- | --- | --- | --- | --- | --- | --- | --- | --- |
| Light-emitting device 3 | ITSO (70 nm) | DBT3P-II: MoOx (2:1 50 nm) | PCBBiIBP (20 nm) | * | mINc(II)PTzn (20 nm) | Bphen (15 nm) | LiF (1 nm) | Al (200 nm) |
| Light-emitting device 4 | ITSO (70 nm) | DBT3P-II: MoOx (2:1 50 nm) | PCBBiIBP (20 nm) | ** | 8βN-4mDBIPBfpm (20 nm) | Bphen (15 nm) | LiF (1 nm) | Al (200 nm) |

TABLE 10-continued

|  | First electrode | Hole-injection layer | Hole-transport layer | Light-emitting layer | Electron-transport layer | Electron-injection layer | Second electrode |
|---|---|---|---|---|---|---|---|
| Comparative light-emitting device a3 | ITSO (70 nm) | DBT3P-II: MoOx (2:1 50 nm) | PCBBiLBP (20 nm) | *** | mPCCzPTzn-02 (20 nm) | Bphen (15 nm) | LiF (1 nm) | Al (200 nm) |

* mINc(II)PTzn:PCCP:[Ir(ppy)$_2$(4dppy)] (0.6:0.4:0.1 40 nm)
** 8βN-4mDBtPBfpm:PCCP:[Ir(ppy)$_2$(4dppy)] (0.6:0.4:0.1 40 nm)
*** mPCCzPTm-02:PCCP:[Ir(ppy)$_2$(4dppy)] (0.6:0.4:0.1 40 nm)

Note that in Table 10, mINc(II)PTzn is an abbreviation for 5-[3-(4,6-diphenyl-1,3,5-triazin-2-yl)phenyl]-7,7-dimethyl-5H,7H-indeno[2,1-b]carbazole, and 8βN-4mDBtPBfpm is an abbreviation for 4-[3-(dibenzothiophen-4-yl)phenyl]-8-(naphthalen-2-yl)-[1]benzofuro[3,2-d]pyrimidine.

<<Operation Characteristics 3 of Light-Emitting Devices>>

The operation characteristics of the fabricated light-emitting device 3, light-emitting device 4, and comparative light-emitting device a3 were measured at room temperature. The results are shown in FIG. 28 to FIG. 31.

Table 11 shows the initial values of main characteristics of the light-emitting devices at around 1000 cd/m$^2$.

Figure 33:
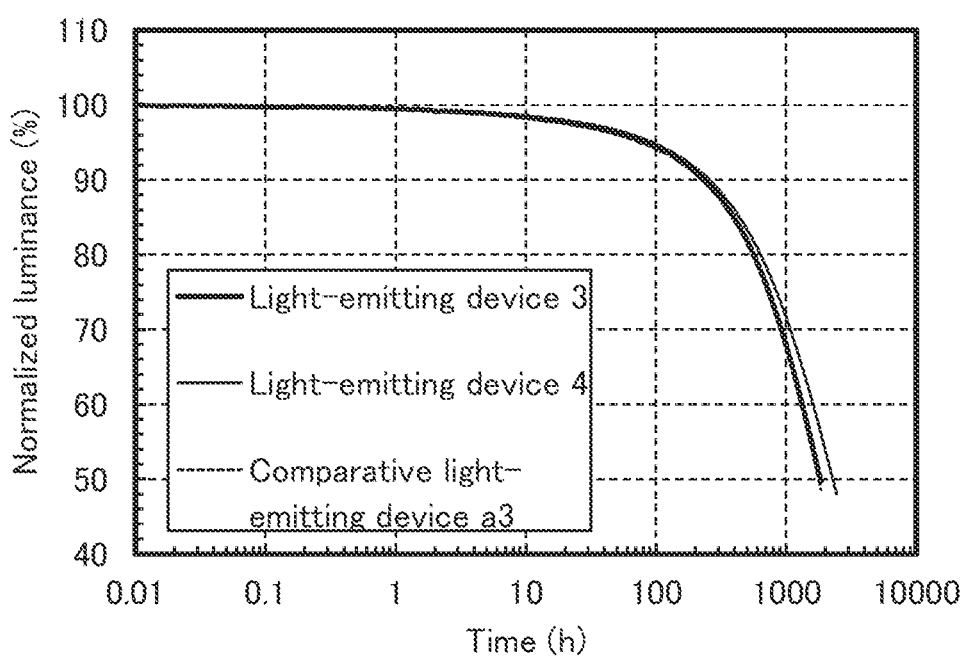
FIG. 33 is a graph showing the reliabilities of the light-emitting device 3, the light-emitting device 4, and the comparative light-emitting device a3.
Figure 34:
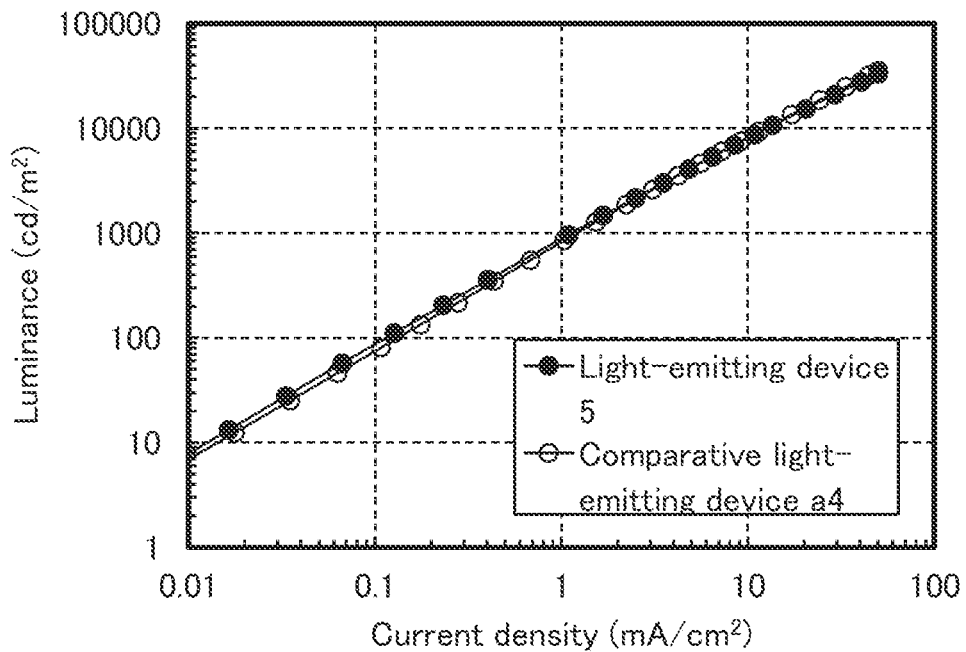
FIG. 34 is a graph showing the luminance-current density characteristics of a light-emitting device 5 and a comparative light-emitting device a4.
Figure 35:
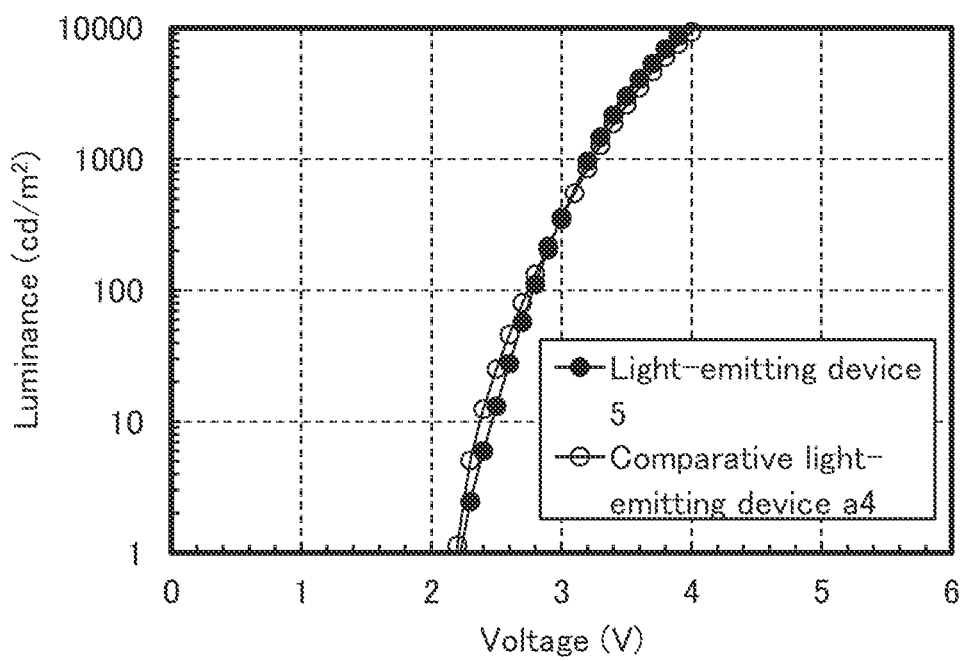
FIG. 35 is a graph showing the luminance-voltage characteristics of the light-emitting device 5 and the comparative light-emitting device a4.
Figure 36:
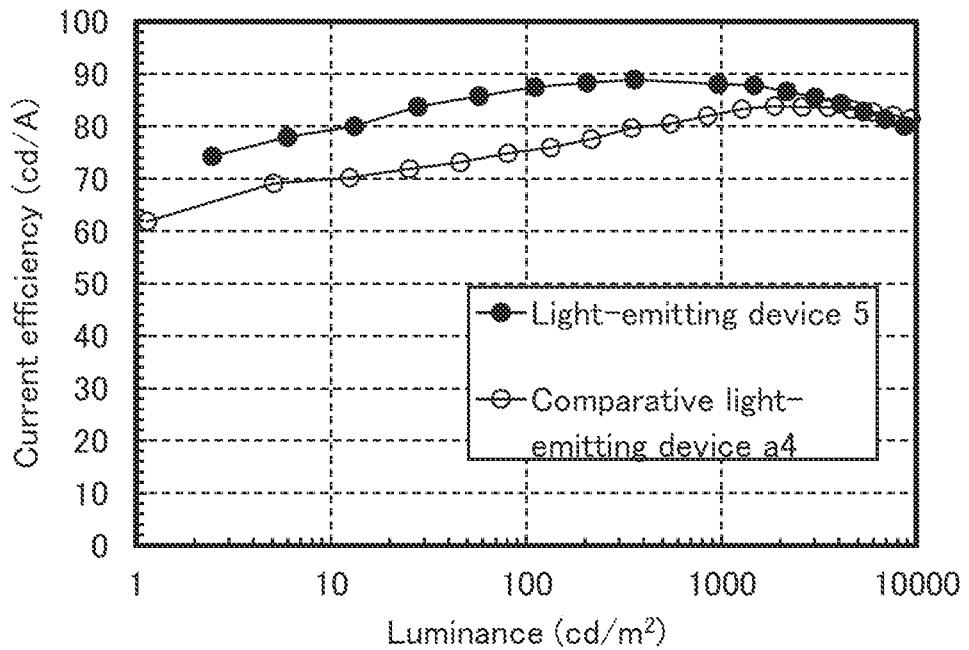
FIG. 36 is a graph showing the current efficiency-luminance characteristics of the light-emitting device 5 and the comparative light-emitting device a4.
Figure 37:
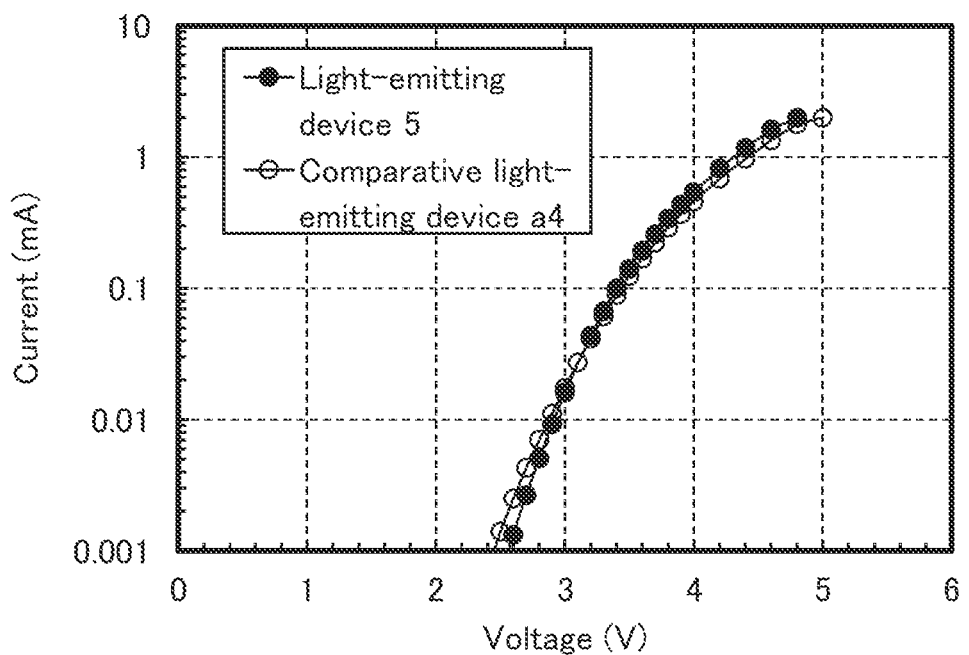
FIG. 37 is a graph showing the current-voltage characteristics of the light-emitting device 5 and the comparative light-emitting device a4.

Next, reliability tests were performed on the light-emitting devices. FIG. 33 shows results of the reliability tests. In FIG. 33, the vertical axis represents normalized luminance (%) with an initial luminance of 100%, and the horizontal axis represents driving time (h) of the devices. Note that in the reliability tests, the light-emitting devices were driven at a constant current of 2 mA.

Next, light-emitting devices (the light-emitting device 5 and the comparative light-emitting device a4) having structures different from those of the above light-emitting devices will be described. These light-emitting devices can be fabricated by a method similar to those of the above light-emitting devices. The specific structures are shown in Table 12 below.

TABLE 11

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting device 3 | 3.1 | 0.038 | 0.94 | (0.46, 0.53) | 740 | 78 | 79 | 25 |
| Light-emitting device 4 | 3.1 | 0.037 | 0.92 | (0.46, 0.53) | 730 | 80 | 81 | 25 |
| Comparative light-emitting device a3 | 3.3 | 0.050 | 1.3 | (0.46, 0.53) | 960 | 77 | 73 | 23 |

Figure 32:
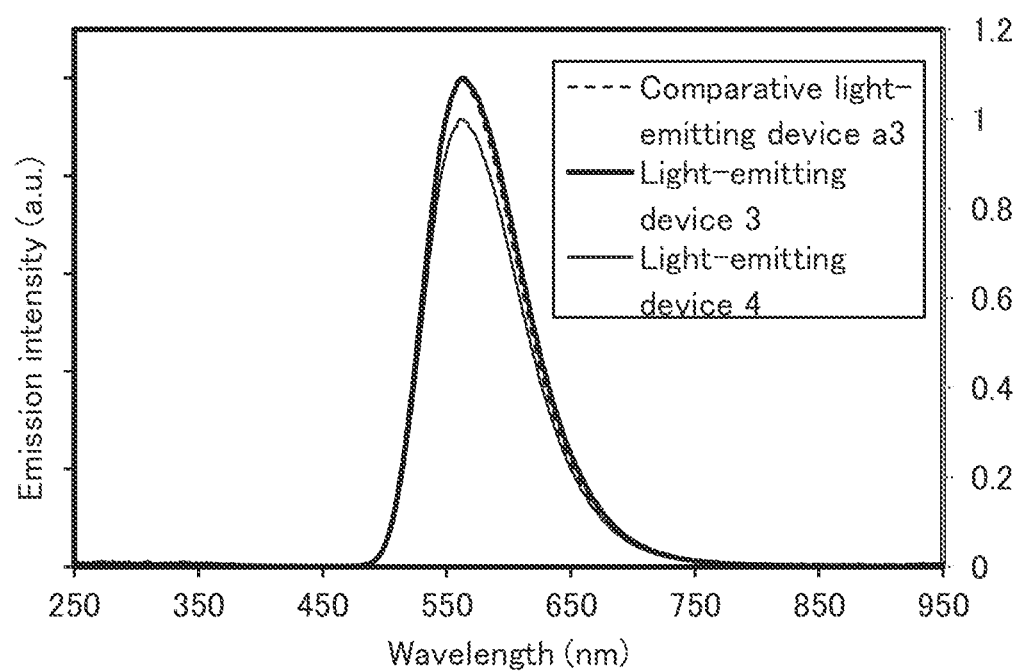
FIG. 32 shows the emission spectra of the light-emitting device 3, the light-emitting device 4, and the comparative light-emitting device a3.

FIG. 32 shows emission spectra when current at a current density of 2.5 mA/cm$^2$ was supplied to the light-emitting devices. As shown in FIG. 32, the emission spectrum of each light-emitting device has a peak at around 564 nm, which is presumably derived from light emission of [Ir(ppy)$_2$(4dppy)] contained in the light-emitting layer 913.

TABLE 12

|  | First electrode | Hole-injection layer | Hole-transport layer | Light-emitting layer | Electron-transport layer | Electron-injection layer | Second electrode |
|---|---|---|---|---|---|---|---|
| Light-emitting device 5 | ITSO (70 nm) | DBT3P-II:MoOx (2:1 50 nm) | PCBBiLBP (20 nm) | * | mPCCzPTzn-02 (20 nm) | Bphen (15 nm) | LiF (1 nm) | Al (200 nm) |

TABLE 12-continued

|  | First electrode | Hole-injection layer | Hole-transport layer | Light-emitting layer | Electron-transport layer | | Electron-injection layer | Second electrode |
|---|---|---|---|---|---|---|---|---|
| Comparative light-emitting device a4 | ITSO (70 nm) | DBT3P-II:MoOx (2:1 50 nm) | PCBBiLBP (20 nm) | ** | mPCCzPTzn-02 (20mn) | Bphen (15 nm) | LiF (1 nm) | Al (200 nm) |

* 8mDBtBPNfpm:PCCP:Ir(ppy)$_2$(4dppy) (0.6:0.4:0.1 40 nm)
** mPCCzPTzn-02:PCCP:Ir(ppy)$_2$(4dppy) (0.6:0.4:0.1 40 nm)

Note that 8mDBtBPNfpm in Table 11 is an abbreviation for 8-[3'-(dibenzothiophen-4-yl)(1,1'-biphenyl-3-yl)]naphtho[1',2':4,5]furo[3,2-d]pyrimidine.

<<Operation Characteristics 4 of Light-Emitting Devices>>

The operation characteristics of the fabricated light-emitting device 5 and comparative light-emitting device a4 were measured at room temperature. The results are shown in FIG. 34 to FIG. 37.

Table 13 shows the initial values of main characteristics of the light-emitting devices at around 1000 cd/m².

Figure 39:
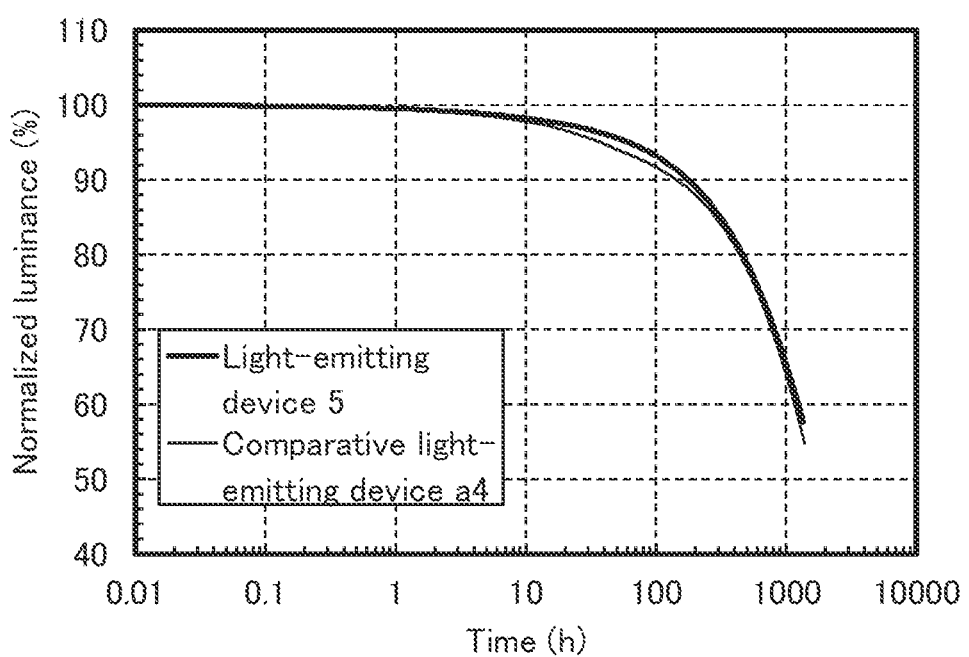
FIG. 39 is a graph showing the reliabilities of the light-emitting device 5 and the comparative light-emitting device a4.
Figure 40:
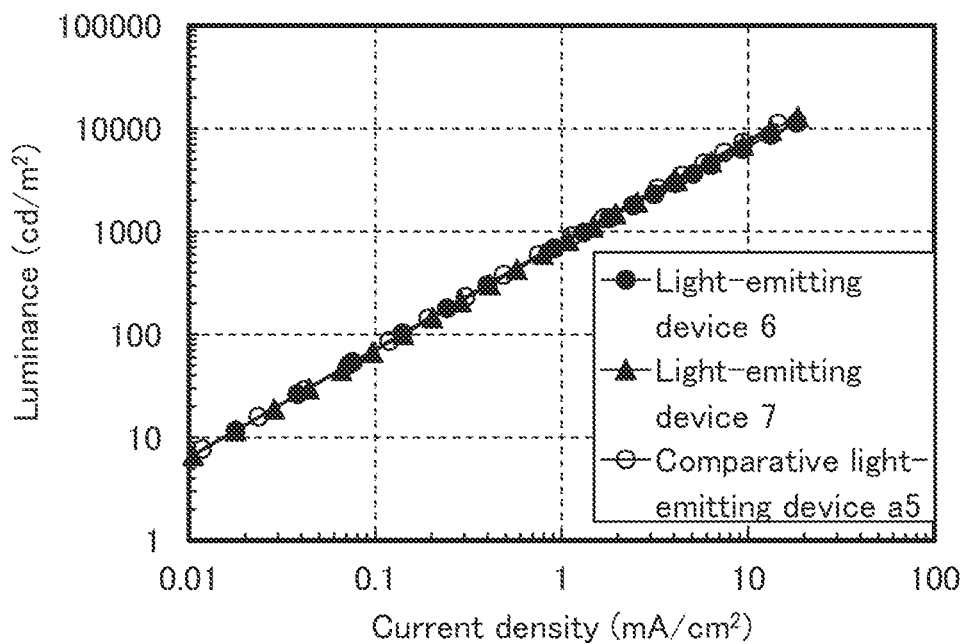
FIG. 40 is a graph showing the luminance-current density characteristics of a light-emitting device 6, a light-emitting device 7, and a comparative light-emitting device a5.
Figure 41:
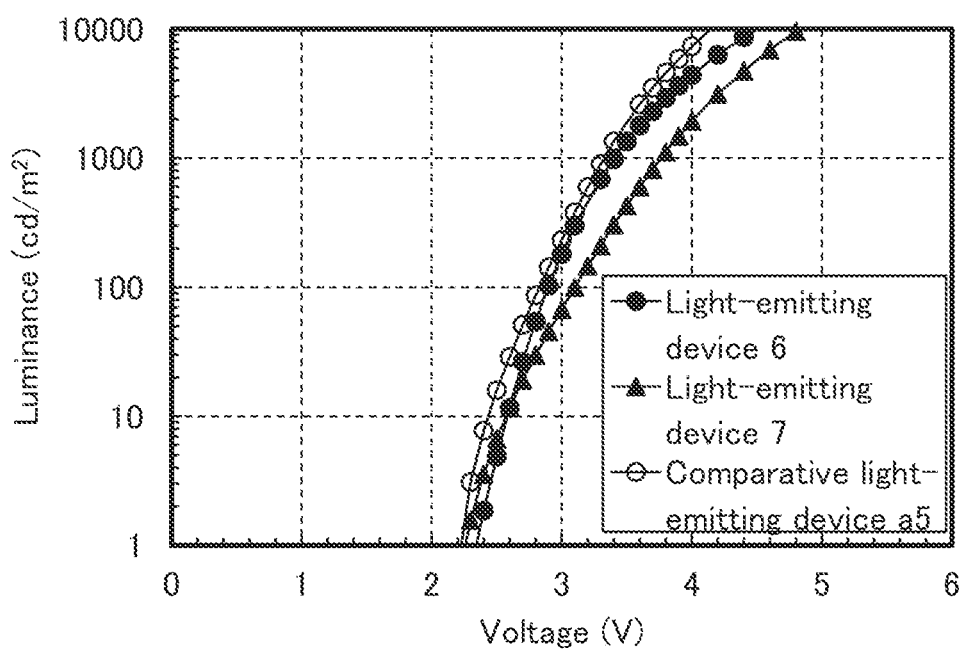
FIG. 41 is a graph showing the luminance-voltage characteristics of the light-emitting device 6, the light-emitting device 7, and the comparative light-emitting device a5.
Figure 42:
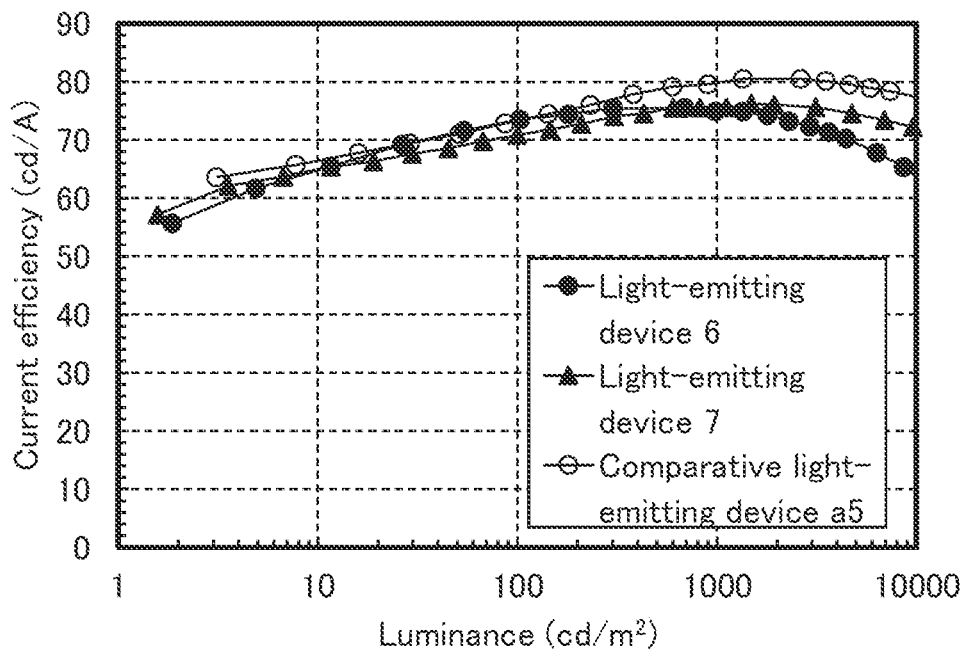
FIG. 42 is a graph showing the current efficiency-luminance characteristics of the light-emitting device 6, the light-emitting device 7, and the comparative light-emitting device a5.
Figure 43:
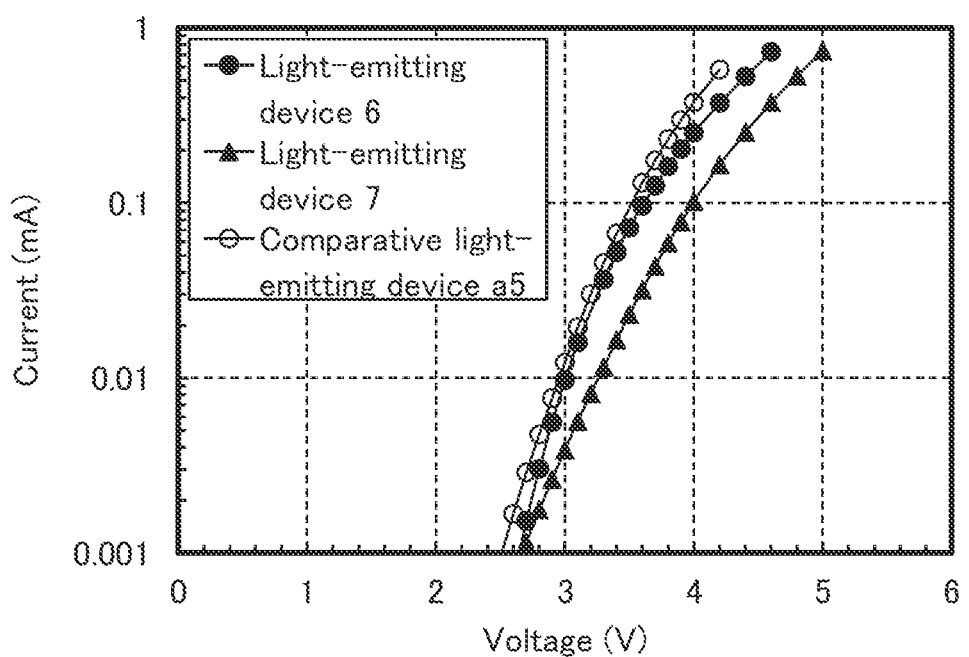
FIG. 43 is a graph showing the current-voltage characteristics of the light-emitting device 6, the light-emitting device 7, and the comparative light-emitting device a5.

Next, reliability tests were performed on the light-emitting devices. FIG. 39 shows results of the reliability tests. In FIG. 39, the vertical axis represents normalized luminance (%) with an initial luminance of 100%, and the horizontal axis represents driving time (h) of the devices. Note that in the reliability tests, the light-emitting devices were driven at a constant current of 2 mA.

TABLE 13

|  | Voltage (V) | Current (mA) | Current density (mA/cm²) | Chromaticity (x, y) | Luminance (cd/m²) | Current efficiency (cd/A) | Power efficiency (lm/W) | External quantumn efficiency (%) |
|---|---|---|---|---|---|---|---|---|
| Light-emitting device 5 | 3.2 | 0.044 | 1.1 | (0.45, 0.54) | 960 | 88 | 86 | 26 |
| Comparative light-emitting device a4 | 3.2 | 0.041 | 1.0 | (0.45, 0.54) | 850 | 82 | 80 | 24 |

Figure 38:
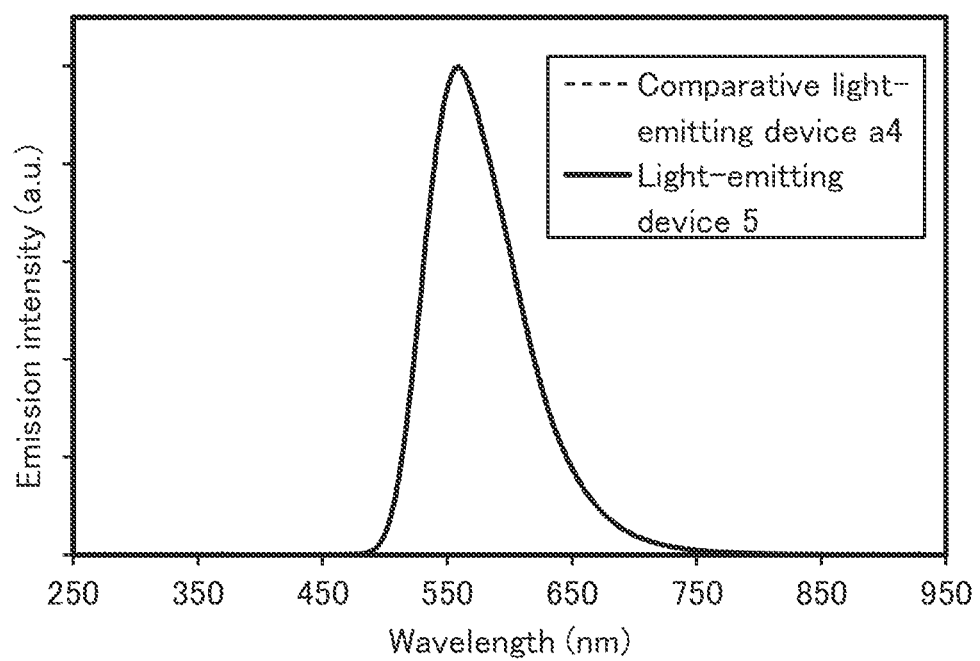
FIG. 38 shows the emission spectra of the light-emitting device 5 and the comparative light-emitting device a4.

FIG. 38 shows emission spectra when current at a current density of 2.5 mA/cm² was supplied to the light-emitting devices. As shown in FIG. 38, the emission spectrum of each light-emitting device has a peak at around 559 nm, which is presumably derived from light emission of [Ir(ppy)$_2$(4dppy)] contained in the light-emitting layer 913.

Next, light-emitting devices (the light-emitting device 6, the light-emitting device 7, and the comparative light-emitting device a5) having structures different from those of the above light-emitting devices will be described. These light-emitting devices can be fabricated by a method similar to those of the above light-emitting devices. The specific structures are shown in Table 14 below.

TABLE 14

|  | First electrode | Hole-injection layer | Hole-transport layer | Light-emitting layer | Electron-transport layer | | Electron-injection layer | Second electrode |
|---|---|---|---|---|---|---|---|---|
| Light-emitting device 6 | ITSO (70 nm) | DBT3P-II: MoOx (2:1 50 nm) | PCBBiLBP (20 nm) | * | 3,8mDBtP2Bfpr (20 nm) | Bphen (15 nm) | LiF (1 nm) | Al (200 nm) |
| Light-emitting device 7 | ITSO (70 nm) | DBT3P-II: MoOx (2:1 50 nm) | PCBBiLBP (20 nm) | ** | 4,8mDBtP2Bfpm (20 nm) | Bphen (15 nm) | LiF (1 nm) | Al (200 nm) |

TABLE 14-continued

| | First electrode | Hole-injection layer | Hole-transport layer | Light-emitting layer | Electron-transport layer | | Electron-injection layer | Second electrode |
|---|---|---|---|---|---|---|---|---|
| Comparative light-emitting device a5 | ITSO (70 nm) | DBT3P-II: MoOx (2:1 50 nm) | PCBBiIBP (20 nm) | *** | mPCCzPTzn-02 (20 nm) | Bphen (15 nm) | LiF (1 nm) | Al (200 nm) |

\* 3,8mDBtP2Bfpr:PCCP:[Ir(ppy)$_2$(4dppy)] (0.6:0.4:0.1 40 nm)
\*\* 4,8mDBtP2Bfpm:PCCP:[Ir(ppy)$_2$(4dppy)] (0.6:0.4:0.1 40 nm)
\*\*\* mPCCzPTzn-02:PCCP:[Ir(ppy)$_2$(4dppy)] (0.6:0.4:0.1 40 nm)

Note that in Table 14, 3,8mDBtP2Bfpr is an abbreviation for 3,8-bis[3-(dibenzothiophen-4-yl)phenyl]benzofuro[2,3-b]pyrazine, and 4,8mDBtP2Bfpm is an abbreviation for 4,8-bis[3-(dibenzothiophen-4-yl)phenyl]-[1]benzofuro[3,2-d]pyrimidine.

<<Operation Characteristics 5 of Light-Emitting Devices>>

The operation characteristics of the fabricated light-emitting device 6, light-emitting device 7, and comparative light-emitting device a5 were measured at room temperature. The results are shown in FIG. 40 to FIG. 43.

Table 15 shows the initial values of main characteristics of the light-emitting devices at around 1000 cd/m$^2$.

TABLE 15

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting device 6 | 3.4 | 0.052 | 1.3 | (0.47, 0.53) | 980 | 75 | 69 | 23 |
| Light-emitting device 7 | 3.8 | 0.059 | 1.5 | (0.45, 0.54) | 1100 | 76 | 63 | 23 |
| Comparative light-emitting device a5 | 3.3 | 0.045 | 1.1 | (0.45, 0.54) | 900 | 80 | 76 | 24 |

Figure 44:
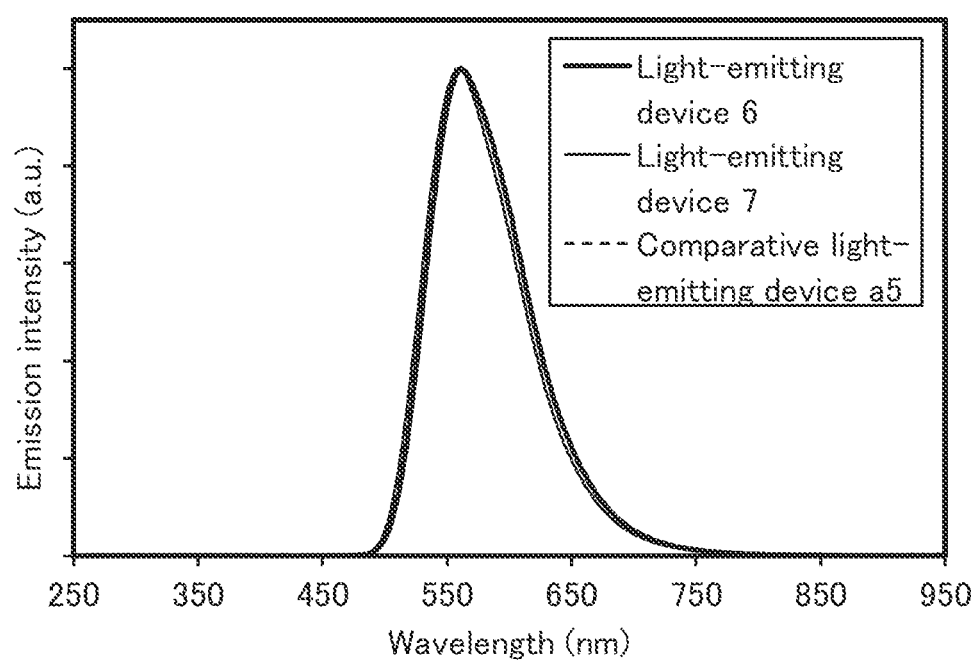
FIG. 44 shows the emission spectra of the light-emitting device 6, the light-emitting device 7, and the comparative light-emitting device a5.

FIG. 44 shows emission spectra when current at a current density of 2.5 mA/cm$^2$ was supplied to the light-emitting devices. As shown in FIG. 44, the emission spectrum of each light-emitting device has a peak at around 560 nm, which is presumably derived from light emission of [Ir(ppy)$_2$(4dppy)] contained in the light-emitting layer 913.

Figure 45:
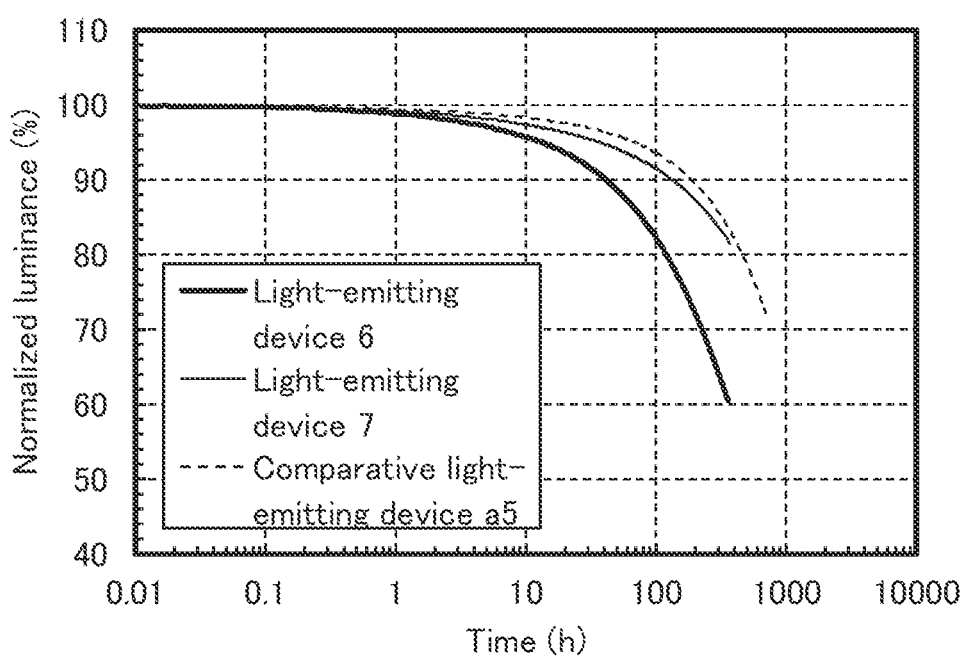
FIG. 45 is a graph showing the reliabilities of the light-emitting device 6, the light-emitting device 7, and the comparative light-emitting device a5.
Figure 46:
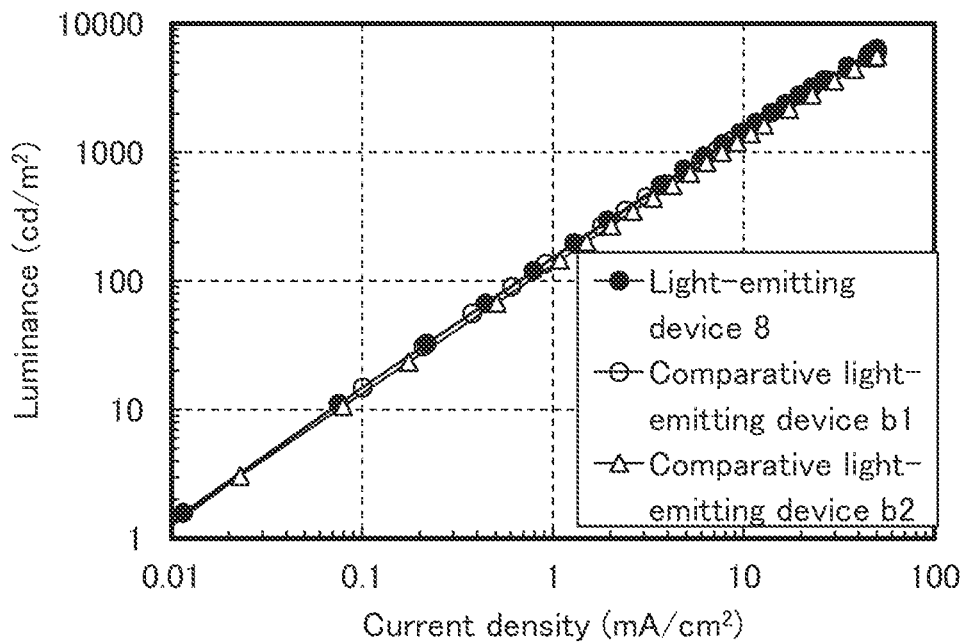
FIG. 46 is a graph showing the luminance-current density characteristics of a light-emitting device 8, a comparative light-emitting device b1, and a comparative light-emitting device b2.
Figure 47:
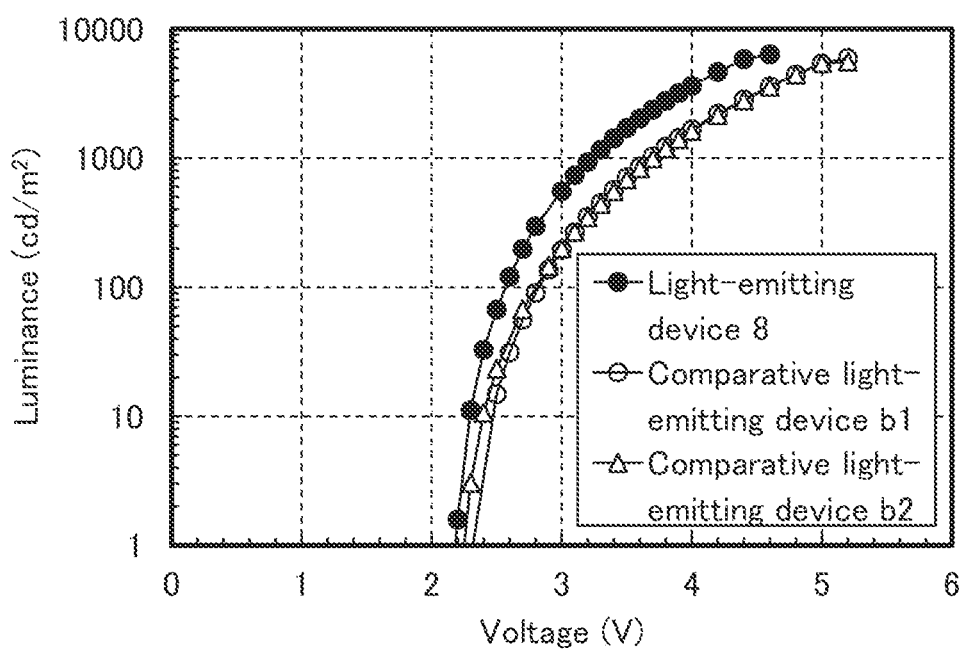
FIG. 47 is a graph showing the luminance-voltage characteristics of the light-emitting device 8, the comparative light-emitting device b1, and the comparative light-emitting device b2.
Figure 48:
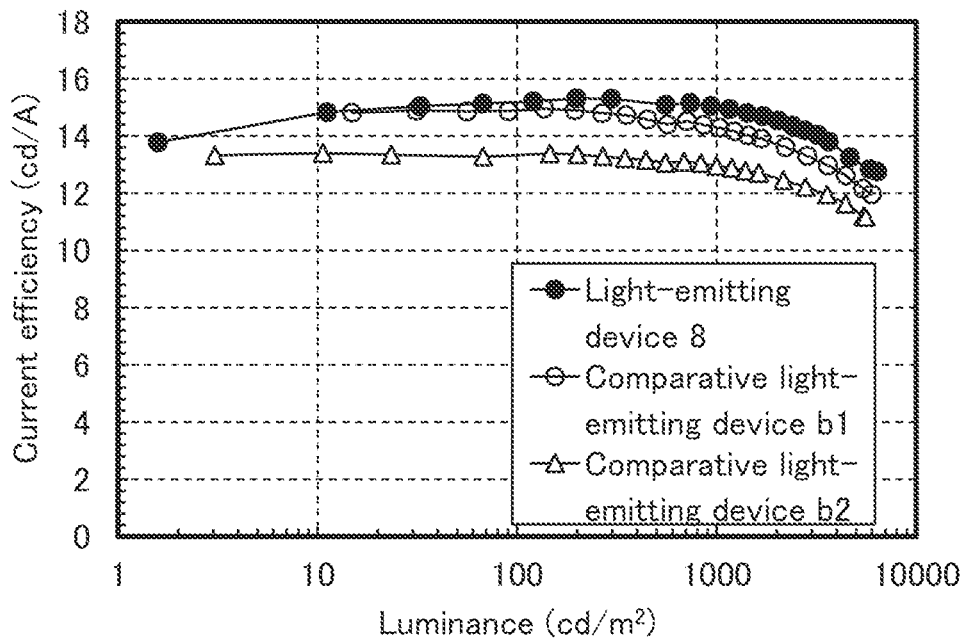
FIG. 48 is a graph showing the current efficiency-luminance characteristics of the light-emitting device 8, the comparative light-emitting device b1, and the comparative light-emitting device b2.
Figure 49:
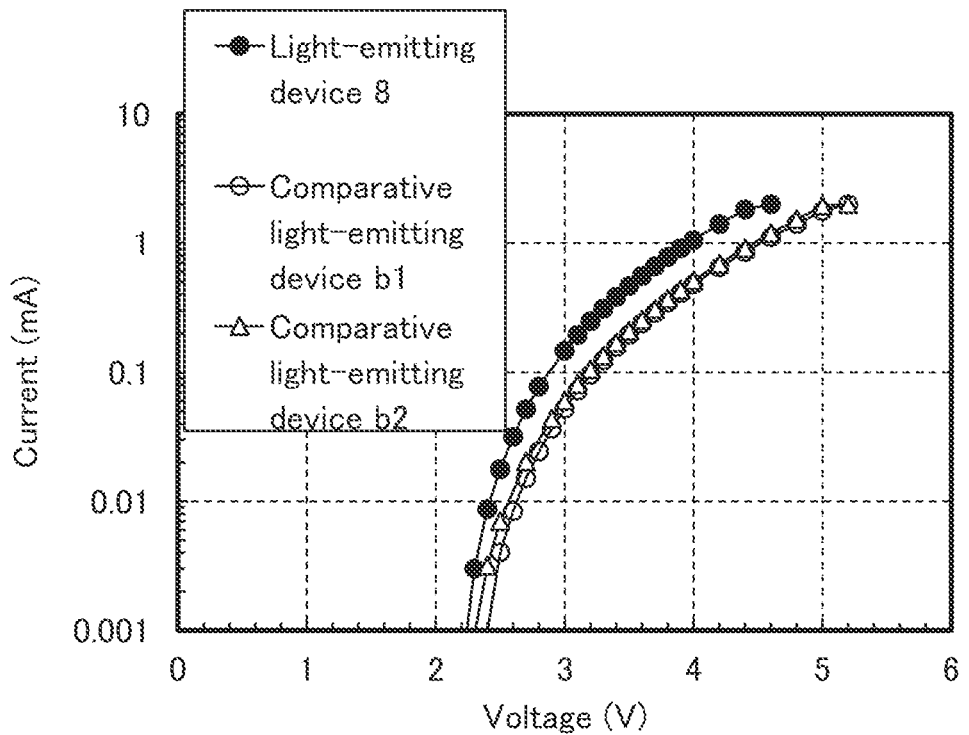
FIG. 49 is a graph showing the current-voltage characteristics of the light-emitting device 8, the comparative light-emitting device b1, and the comparative light-emitting device b2.

Next, reliability tests were performed on the light-emitting devices. FIG. 45 shows results of the reliability tests. In FIG. 45, the vertical axis represents normalized luminance (%) with an initial luminance of 100%, and the horizontal axis represents driving time (h) of the devices. Note that in the reliability tests, the light-emitting devices were driven at a constant current of 2 mA.

Example 3

In this example, the case of fabricating light-emitting devices each using a guest material that emits light with a wavelength longer than those of the light-emitting devices described in Example 1 and Example 2 will be described below. Note that bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]) was used as the guest material in this example. The device structures of the light-emitting devices described in this example are illustrated in FIG. 15, and a fabrication method thereof is similar to that in Example 2.

The chemical formulae of materials used for in this example are shown below. Specific structures of the light-emitting devices are shown in Table 16 below.

[Chemical Formulae 5]

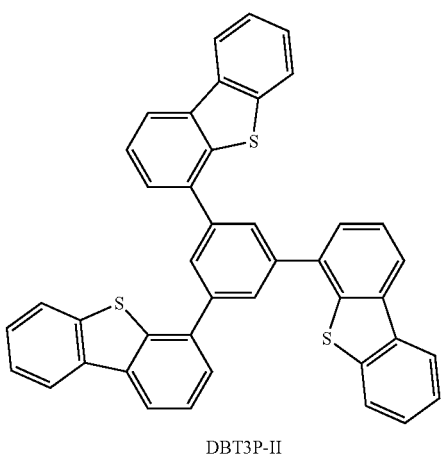

DBT3P-II

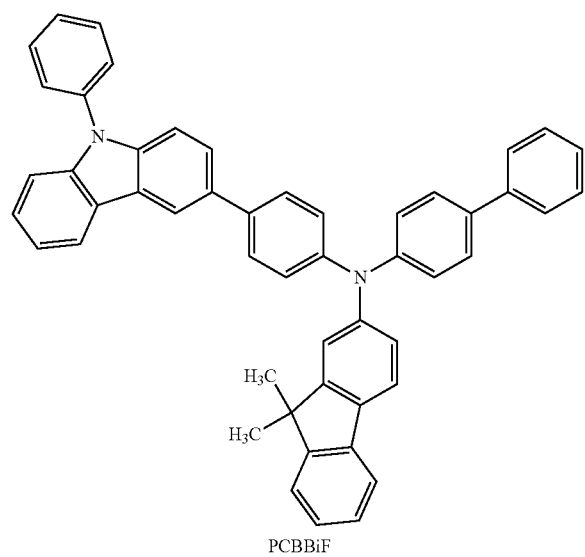
PCBBiF
9mDBtBPNfpr
BPAFLP
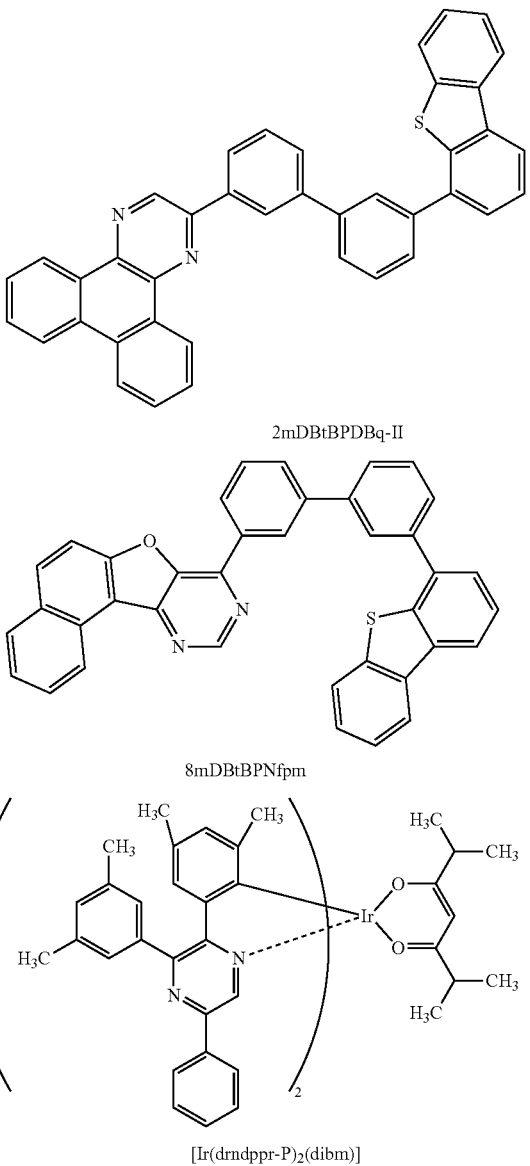
2mDBtBPDBq-II
8mDBtBPNfpm
[Ir(drndppr-P)₂(dibm)]
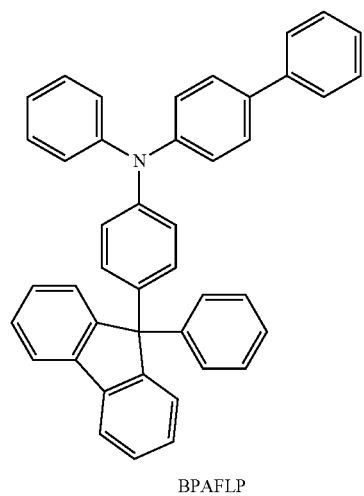
NBphen

TABLE 16

| | First electrode | Hole-injection layer | Hole-transport layer | Light-emitting layer | Electron-transport layer | | Electron-injection layer | Second electrode |
|---|---|---|---|---|---|---|---|---|
| Light-emitting device 8 | ITSO (70 nm) | DBT3P-II:MoOx (2:1 75 nm) | BPAFLP (20 nm) | * | 9mDBtBPNfpr (30 nm) | NBphen (15 nm) | LiF (1 nm) | Al (200 nm) |
| Comparative light-emitting device b1 | ITSO (70 nm) | DBT3P-II:MoOx (2:1 75 nm) | BPAFLP (20 nm) | ** | 2mDBTBPDBq-II (30 nm) | NBphen (15 nm) | LiF (1 nm) | Al (200 nm) |
| Comparative light-emitting device b2 | ITSO (70 nm) | DBT3P-II:MoOx (2:1 75 nm) | BPAFLP (20 nm) | *** | 8mDBtBPNfpm (30 nm) | NBphen (15 nm) | LiF (1 nm) | Al (200 nm) |

* 9mDBtBPNfpr:PCBBiF:[Ir(dmdppr-P)$_2$(dihm)] (0.75:0.25:0.1 40 nm)
** 2mDBTBPDBq-II:PCBBiF:[Ir(dmdppr-P)$_2$(dibm)] (0.75:0.25:0.1 40 nm)
*** 8mDBtBPNfpm:PCBBiF:[Ir(dmdppr-P)$_2$(dihm)] (0.75:0.25:0.1 40 nm)

Note that BPAFLP in Table 16 is an abbreviation for 4-phenyl-4'-(9-phenylfluoren-9-yl)triphenylamine. In addition, 9mDBtBPNfpr is an abbreviation for 9-[(3'-dibenzothiophen-4-yl)biphenyl-3-yl]naphtho[1',2':4,5]furo[2,3-b]pyrazine, 2mDBTBPDBq-II is an abbreviation for 2-[3'-(dibenzothiophen-4-yl)biphenyl-3-yl]dibenzo[f,h]quinoxaline, 8mDBtBPNfpm is an abbreviation for 8-[3'-(dibenzothiophen-4-yl)(1,1'-biphenyl-3-yl)]naphtho[1',2':4,5]furo[3,2-d]pyrimidine, and PCBBiF is an abbreviation for N-(1,1'-biphenyl-4-yl)-N-[4-(9-phenyl-9H-carbazol-3-yl)phenyl]-9,9-dimethyl-9H-fluoren-2-amine.

<<Operation Characteristics of Light-Emitting Devices>>

The operation characteristics of a light-emitting device 8 and a comparative light-emitting device b1, and a comparative light-emitting device b2 were measured at room temperature. The results are shown in FIG. 46 to FIG. 49.

Table 17 shows the initial values of main characteristics of the light-emitting devices at around 1000 cd/m$^2$.

Figure 50:
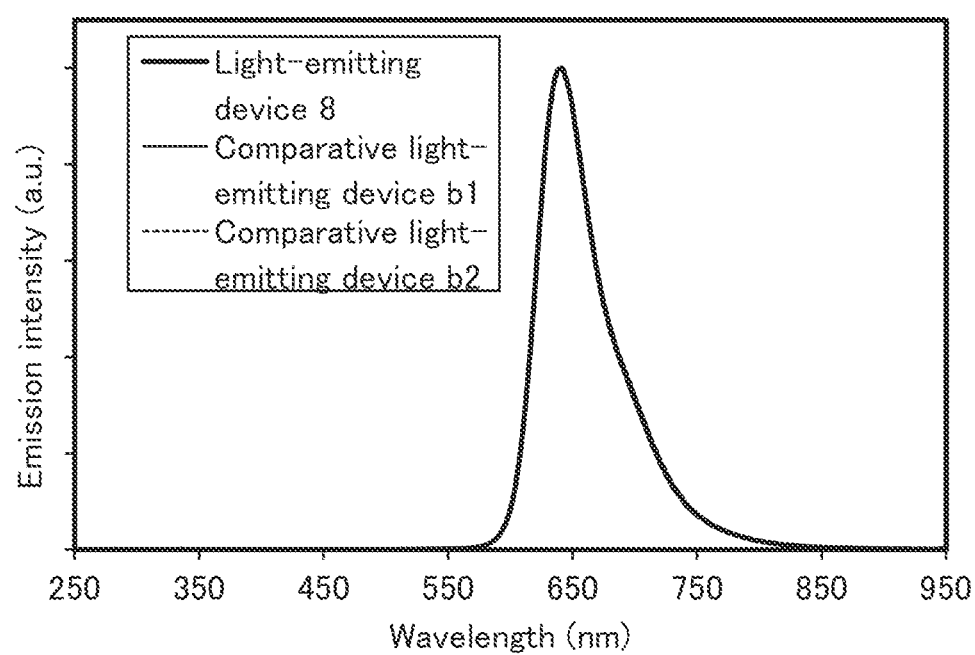
FIG. 50 shows the emission spectra of the light-emitting device 8, the comparative light-emitting device b1, and the comparative light-emitting device b2.

FIG. 50 shows emission spectra when current at a current density of 2.5 mA/cm$^2$ was supplied to the light-emitting devices. As shown in FIG. 50, the emission spectrum of each light-emitting device has a peak at around 640 nm, which is presumably derived from light emission of [Ir(dmdppr-P)$_2$(dibm)] contained in the light-emitting layer 913.

Figure 51:
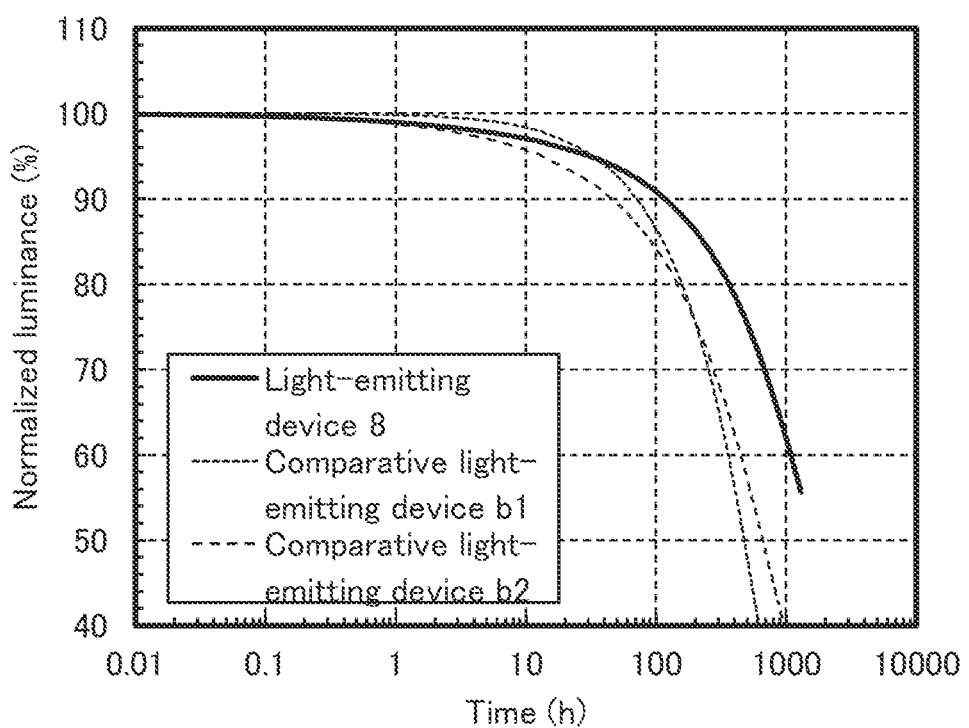
FIG. 51 is a graph showing the reliabilities of the light-emitting device 8, the comparative light-emitting device b1, and the comparative light-emitting device b2.
Figure 52:
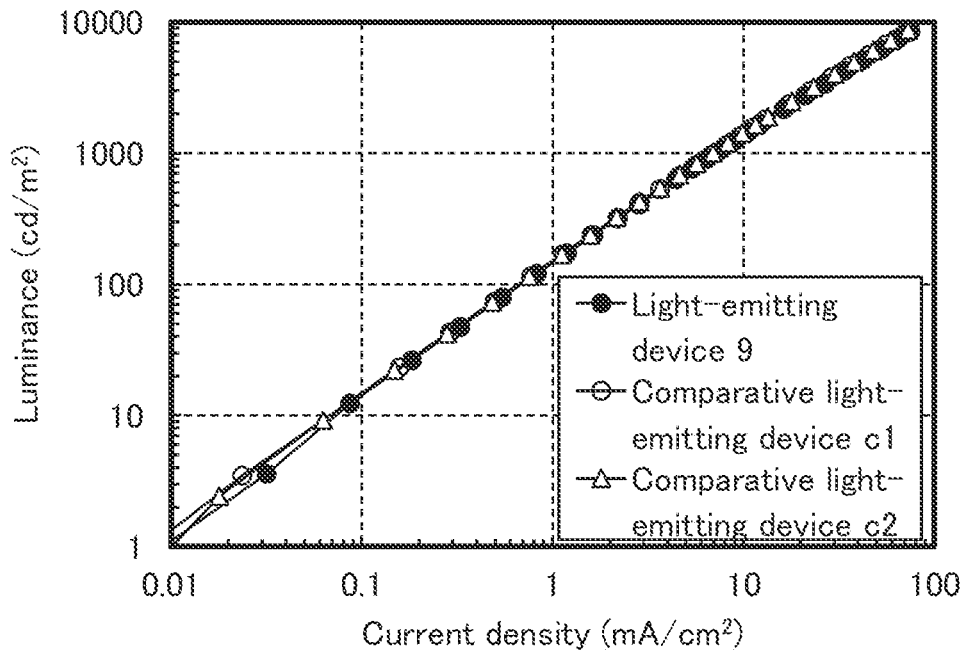
FIG. 52 is a graph showing the luminance-current density characteristics of a light-emitting device 9, a comparative light-emitting device c1, and a comparative light-emitting device c2.
Figure 53:
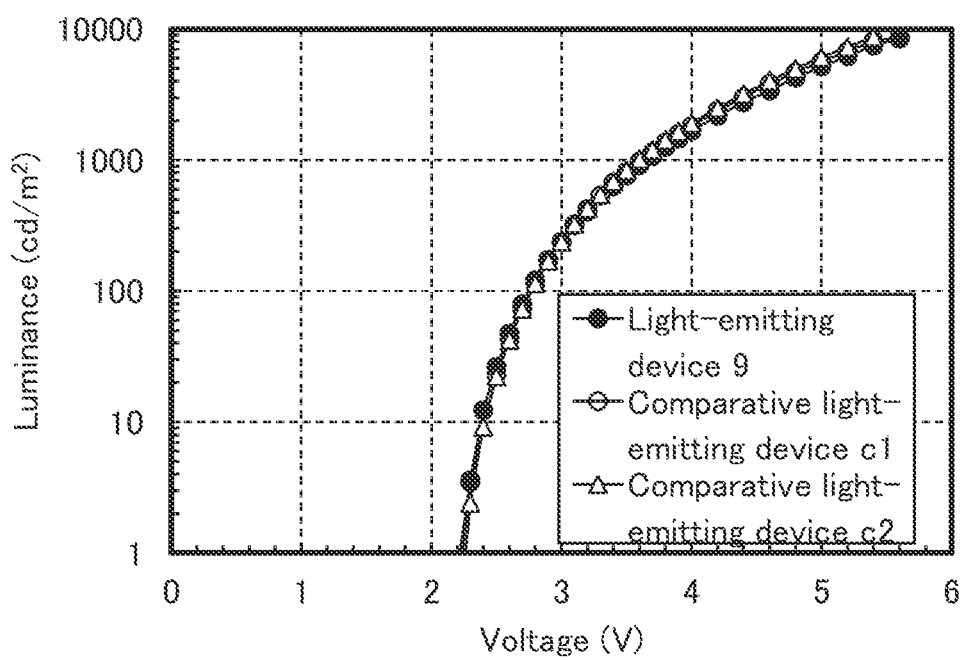
FIG. 53 is a graph showing the luminance-voltage characteristics of the light-emitting device 9, the comparative light-emitting device c1, and the comparative light-emitting device c2.
Figure 54:
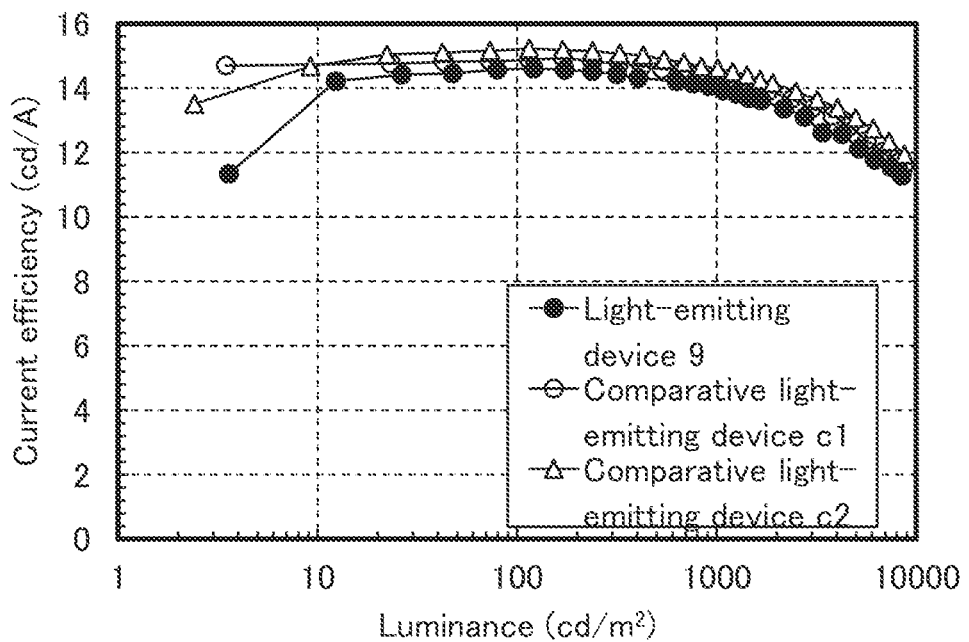
FIG. 54 is a graph showing the current efficiency-luminance characteristics of the light-emitting device 9, the comparative light-emitting device c1, and the comparative light-emitting device c2.
Figure 55:
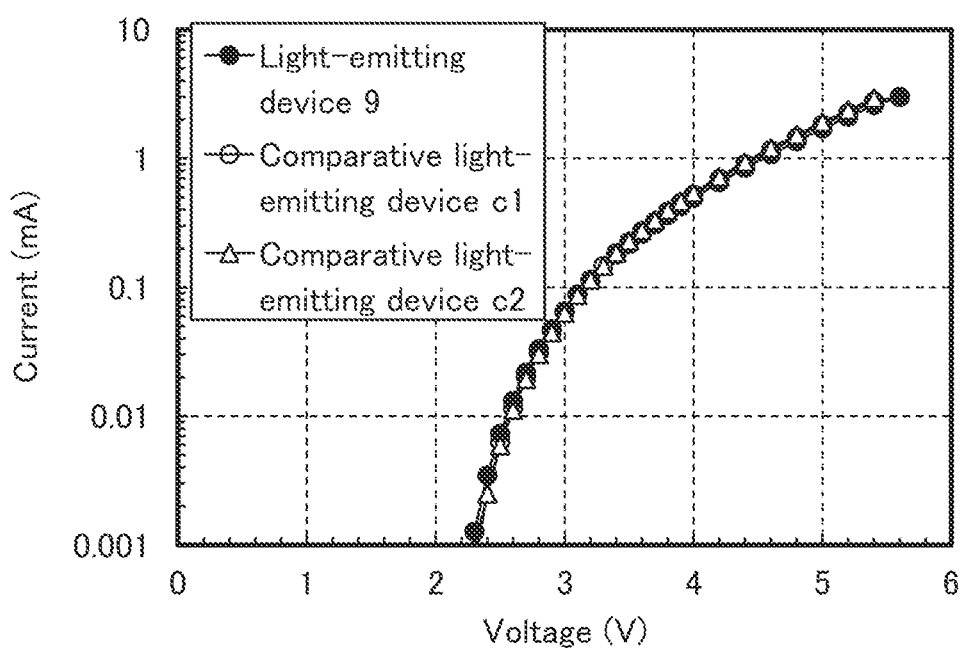
FIG. 55 is a graph showing the current-voltage characteristics of the light-emitting device 9, the comparative light-emitting device c1, and the comparative light-emitting device c2.

Next, reliability tests were performed on the light-emitting devices. FIG. 51 shows results of the reliability tests. In FIG. 51, the vertical axis represents normalized luminance (%) with an initial luminance of 100%, and the horizontal axis represents driving time (h) of the devices. Note that in the reliability tests, the light-emitting devices were driven at a constant current of 3 mA.

From the above results of the operation characteristics, the normalized external quantum efficiency and normalized

TABLE 17

| | Voltage (V) | Current (mA) | Current density (mA/cm2) | Chromaticity (cd/m$^2$) | Luminance (x, y) | Current efficiency (cd/A) | Power efficiency (lm/W) | External quantunm efficiency (%) |
|---|---|---|---|---|---|---|---|---|
| Light-emitting device 8 | 3.2 | 0.25 | 6.2 | (0.71, 0.29) | 930 | 15 | 15 | 26 |
| Comparative light-emitting device b1 | 3.7 | 0.29 | 7.2 | (0.71, 0.29) | 1000 | 14 | 12 | 25 |
| Comparative light-emitting device b2 | 3.7 | 0.31 | 7.7 | (0.71, 0.29) | 1000 | 13 | 11 | 22 | lifetime (LT70) of each of the light-emitting devices were calculated. The results are shown in Table 18. The normalized values were obtained with reference to the values of the comparative light-emitting device b1.

TABLE 18

|  | Host material | Normalized external quantum efficiency | Normalized lifetime (LT70) |
| --- | --- | --- | --- |
| Light-emitting device 8 | 9mDBtBPNfpr | 1.034 | 2.689 |
| Comparative light-emitting device b1 | 2mDBTBPDBq-II | 1.000 | 1.000 |

TABLE 18-continued

|  | Host material | Normalized external quantum efficiency | Normalized lifetime (LT70) |
| --- | --- | --- | --- |
| Comparative light-emitting device b2 | 8mDBtBPNfpm | 0.876 | 1.094 |

The $T_{H(edge)}$ and the $S'_{H(edge)}$ of a mixed material of PCBBiF and the host material shown in Table 18 that is contained in the light-emitting layer of the corresponding light-emitting device fabricated in this example (an exciplex when the exciplex is formed) and the $T_{D(edge)}$ of the guest material ([Ir(ppy)$_2$(4dppy)]) contained therein were obtained in a manner similar to that of Example 1. The results are shown in Table 19. The $T_{D(edge)}$ of [Ir(dmdppr-P)$_2$(dibm)] is 1.974 eV.

TABLE 19

|  | Host material | $T_{H(edge)}$ [eV] | $T_{H(edge)}$-$T_{D(edge)}$ [eV]* | $S'_{H(edge)}$ [eV] | $S'_{H(edge)}$-$T_{H(edge)}$ [eV] |
| --- | --- | --- | --- | --- | --- |
| Light-emitting device 8 | 9mDBtBPNfpr | 2.175 | 0.201 | 2.583 | 0.408 |
| Comparative light-emitting device b1 | 2mDBTBPDBq-II | 2.455 | 0.481 | 2.743 | 0.288 |
| Comparative light-emitting device b2 | 8mDBtBPNfpm | 2.475 | 0.501 | 2.621 | 0.146 |

*$T_{D(edge)}$ = 1.974 [eV] (Absorption edge: 628 nm)

The normalized lifetime of the light-emitting device 8 is longer than those of the comparative light-emitting devices b1 and b2 as shown in Table 18. According to the results in Table 19, only the light-emitting device 8 satisfies both the conditions of Formula (1) and Formula (2) shown in Embodiment 1, where the value ($T_{H(edge)}$-$T_{D(edge)}$) is greater than or equal to 0.07 eV and less than or equal to 0.27 eV and the value ($S'_{H(edge)}$-$T_{H(edge)}$) is greater than or equal to 0.2 eV and less than or equal to 0.5 eV; thus, the light-emitting device 8 has a long lifetime.

Example 4

In this example, the case will be described in which a light-emitting device using a guest material that emits light having a long wavelength was fabricated in a manner similar to that of the light-emitting device described in Example 3. Note that bis[4,6-dimethyl-2-(2-quinolinyl-κN)phenyl-κC] (2,4-pentanedionato-κ$^2$O,O')iridium(III) (abbreviation: [Ir(dmpqn)$_2$(acac)]) was used as a guest material in this example. The device structure of the light-emitting device described in this example is illustrated in FIG. 15, and a fabrication method thereof is similar to that in Example 2.

The chemical formulae of materials used in the light-emitting devices in this example are shown below. Specific structures of the light-emitting devices are shown in Table 20 below.

[Chemical Formulae 6]
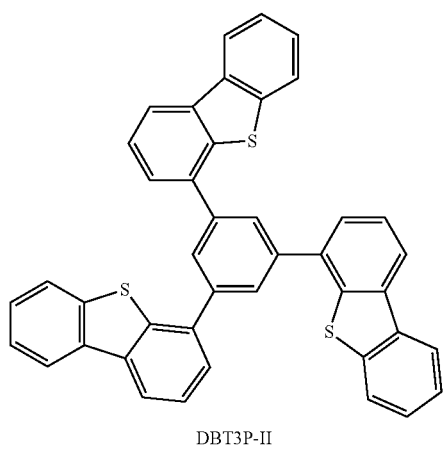
DBT3P-II
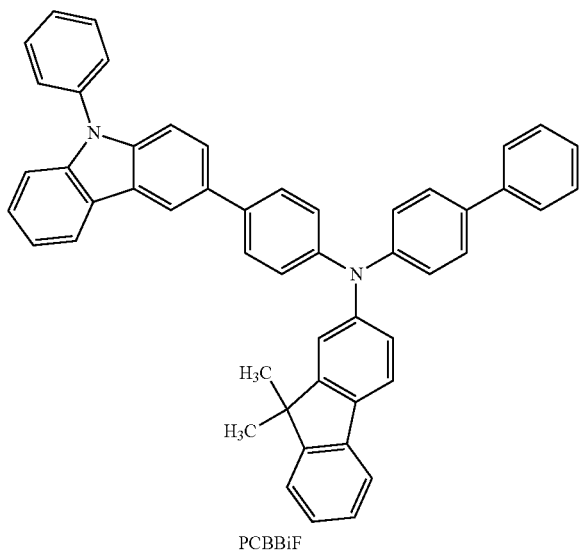
PCBBiF
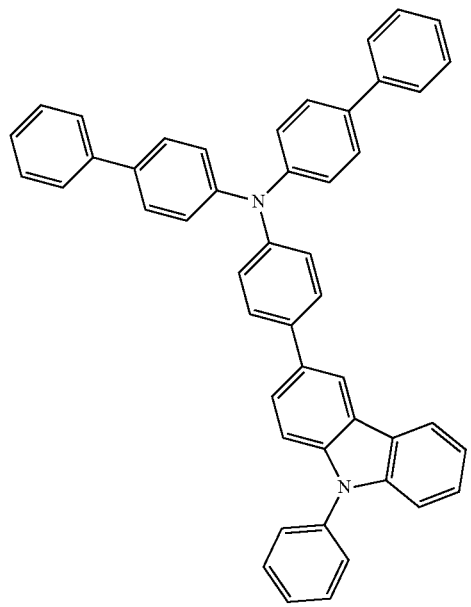
PCBBi1BP
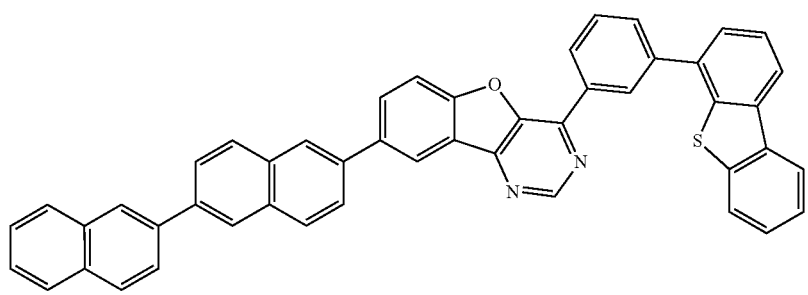
8(βN2)-4mDBtPBfpm -continued

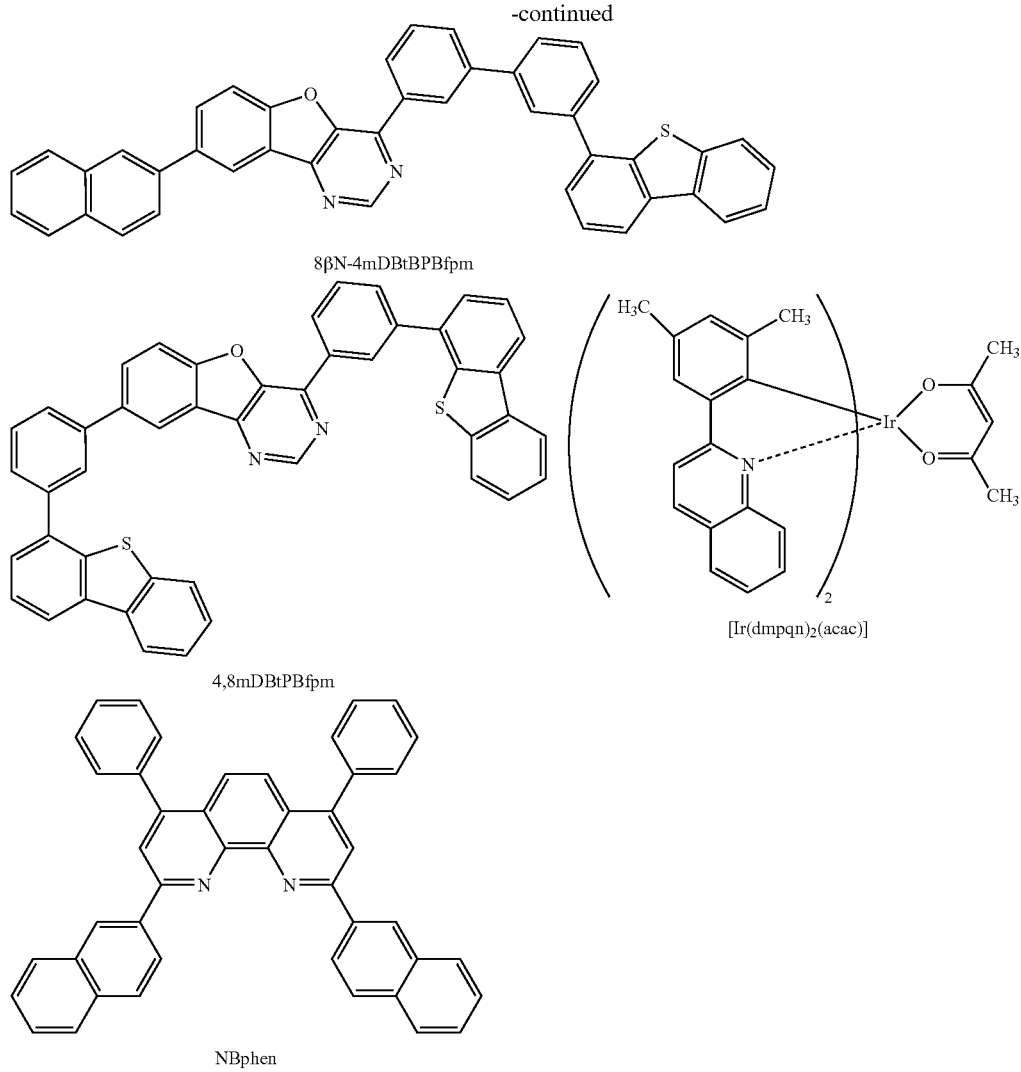

| | First electrode | Hole-injection layer | Hole-transport layer | Light-emitting layer | Electron-transport layer | Electron-injection layer | Second electrode |
|---|---|---|---|---|---|---|---|
| Light-emitting device 9 | ITSO (70 nm) | DBT3P-II: MoOx (2:1 60 nm) | PCBBiIBP (20 nm) | * | 8(βN2)-4mDBtPBfpm (25 nm) | NBphen (15 nm) | LiF (1 nm) | Al (200 nm) |
| Comparative light-emitting device c1 | ITSO (70 nm) | DBT3P-II: MoOx (2:1 60 nm) | PCBBiIBP (20 nm) | ** | 4,8mDBtP2Bfpm (25 nm) | NBphen (15 nm) | LiF (1 nm) | Al (200 nm) |
| Comparative light-emitting device c2 | ITSO (70 nm) | DBT3P-II: MoOx (2:1 60 nm) | PCBBiIBP (20 nm) | *** | 8βN-4mDBtBPBfpm (25 nm) | NBphen (15 nm) | LiF (1 nm) | Al (200 nm) |

\* 8(βN2)-4mDBtPBfpm:PCBBiF:[Ir(dmpqn)$_2$(acac)] (0.75:0.25:0.1 40 nm)

\*\* 4,8mDBtP2Bfpm:PCBBiF:[Ir(dmpqn)$_2$(acac)] (0.75:0.25:0.1 40 nm)

\*\*\* 8βN-4mDBtBPBfpm:PCBBiF:[Ir(dmpqn)$_2$(acac)] (0.75:0.25:0.1 40 nm)

Note that PCBBi1BP in Table 20 is an abbreviation for 4,4'-diphenyl-4"-(9-phenyl-9H-carbazol-3-yl)triphenylamine, 8(βN2)-4mDBtPBfpm is an abbreviation for 8-[(2,2'-binaphthalen)-6-yl]-4-[3-(dibenzothiophen-4-yl)phenyl]-[1]benzofuro[3,2-d]pyrimidine, 4,8mDBtP2Bfpm is an abbreviation for 4,8-bis[3-(dibenzothiophen-4-yl)phenyl]-[1]benzofuro[3,2-d]pyrimidine, and 8βN-4mDBtBPBfpm is an abbreviation for 4-[3'-(dibenzothiophen-4-yl)biphenyl-3-yl]-8-(naphthalen-2-yl)-[1]benzofuro[3,2-d]pyrimidine.

<<Operation Characteristics of Light-Emitting Devices>>

The operation characteristics of a light-emitting device 9, a comparative light-emitting device c1, and a comparative light-emitting device c2 that were fabricated were measured at room temperature. The results are shown in FIG. 52 to FIG. 55.

Table 21 shows the initial values of main characteristics of the light-emitting devices at around 1000 cd/m².

TABLE 21

|  | Voltage (V) | Current (mA) | Current density (mA/cm²) | Chromaticity (x, y) | Luminance (cd/m²) | Current efficiency (cd/A) | Power efficiency (lm/W) | External quantunm efficiency (%) |
|---|---|---|---|---|---|---|---|---|
| Light-emitting device 9 | 3.7 | 0.31 | 7.7 | (0.68, 0.32) | 1100 | 14 | 12 | 16 |
| Comparative light-emitting device c1 | 3.6 | 0.27 | 6.8 | (0.68, 0.32) | 970 | 14 | 12 | 16 |
| Comparative light-emitting device c2 | 3.6 | 0.28 | 6.9 | (0.68, 0.32) | 1100 | 14 | 12 | 16 |

Figure 56:
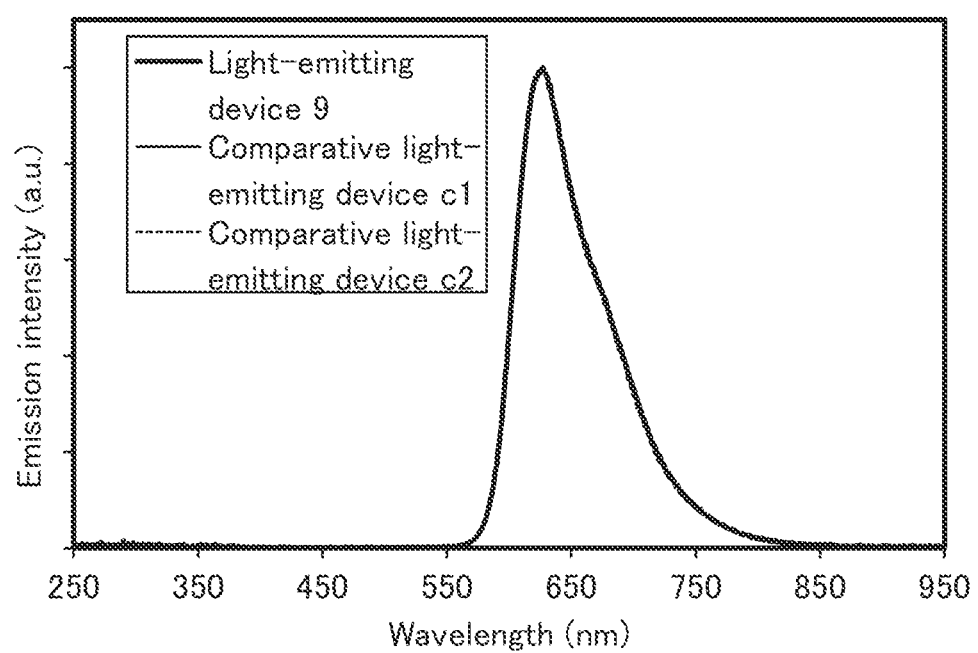
FIG. 56 shows the emission spectra of the light-emitting device 9, the comparative light-emitting device c1, and the comparative light-emitting device c2.

FIG. 56 shows emission spectra when a current at a current density of 2.5 mA/cm² was supplied to the light-emitting devices. As shown in FIG. 56, the emission spectrum of each light-emitting device has a peak at around 626 nm, which is presumably derived from light emission of [Ir(dmpqn)$_2$(acac)] contained in the light-emitting layer 913.

Figure 57:
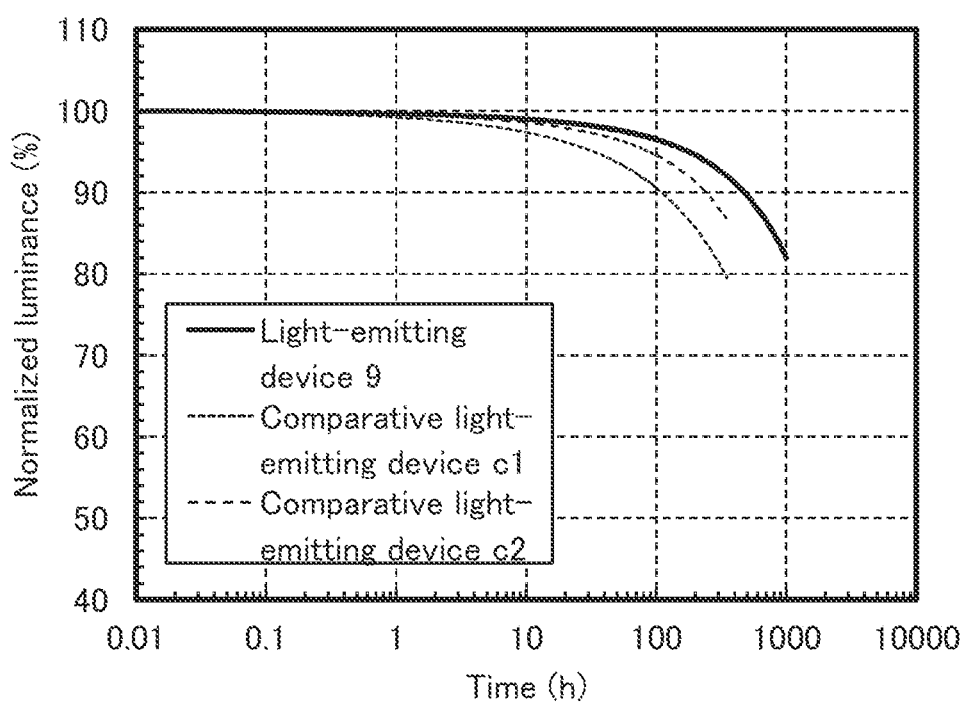
FIG. 57 is a graph showing the reliabilities of the light-emitting device 9, the comparative light-emitting device c1, and the comparative light-emitting device c2.
Figure 58:
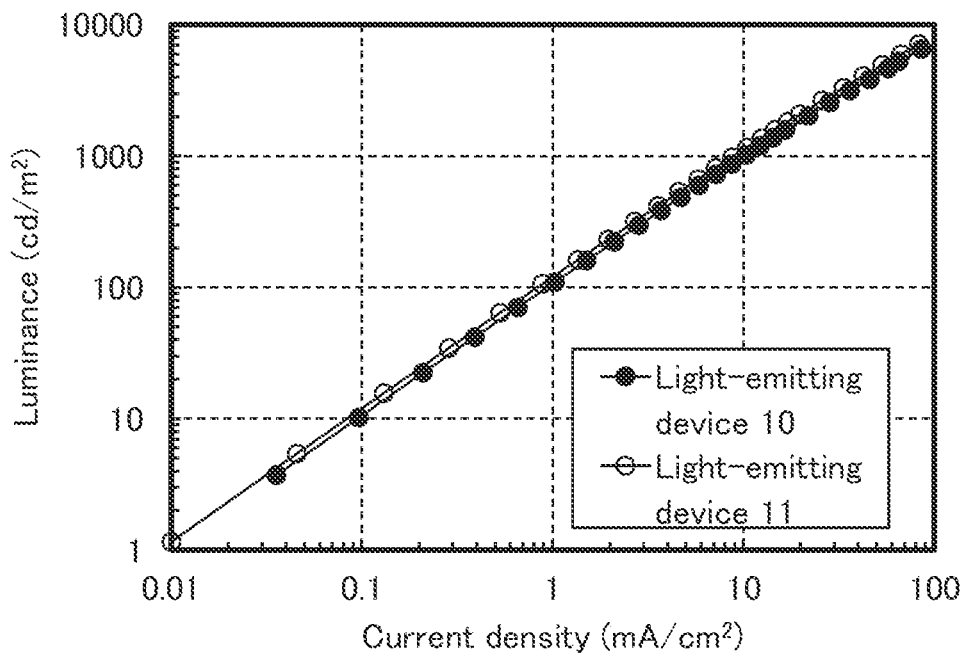
FIG. 58 is a graph showing the luminance-current density characteristics of a light-emitting device 10 and a light-emitting device 11.
Figure 59:
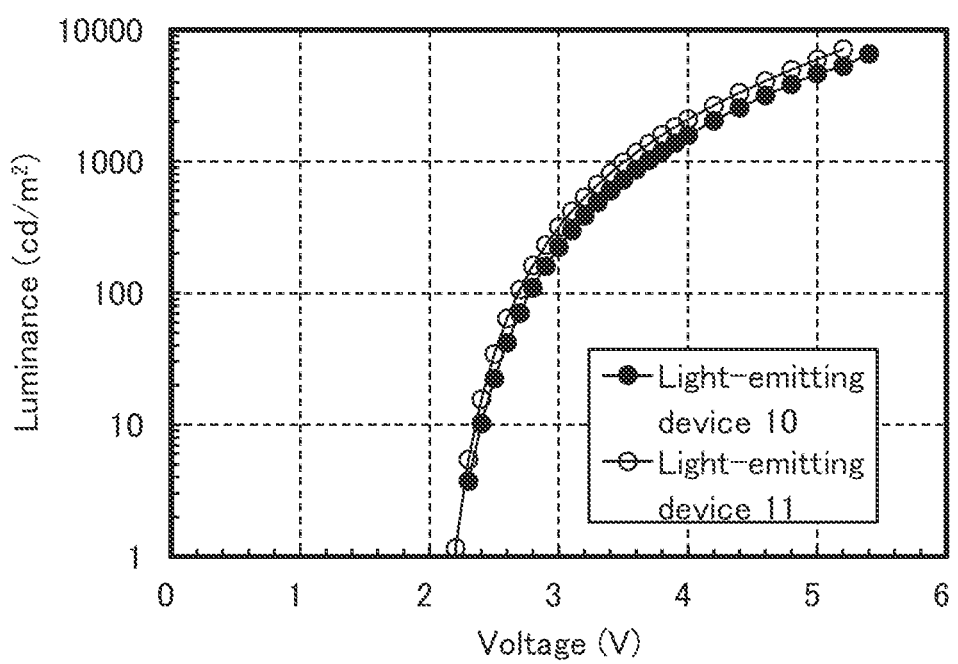
FIG. 59 is a graph showing the luminance-voltage characteristics of the light-emitting device 10 and the light-emitting device 11.
Figure 60:
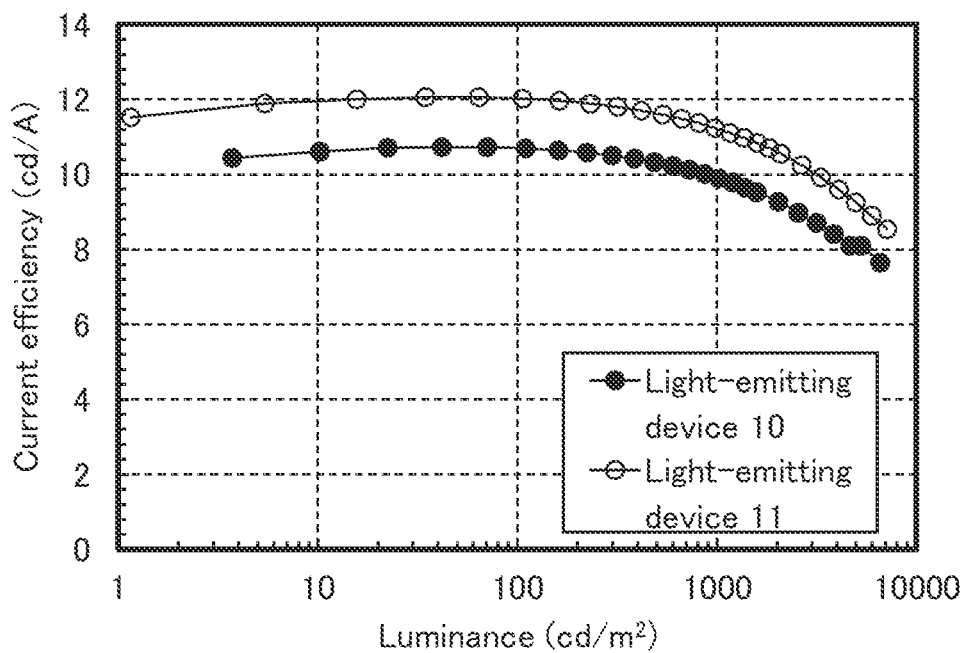
FIG. 60 is a graph showing the current efficiency-luminance characteristics of the light-emitting device 10 and the light-emitting device 11.
Figure 61:
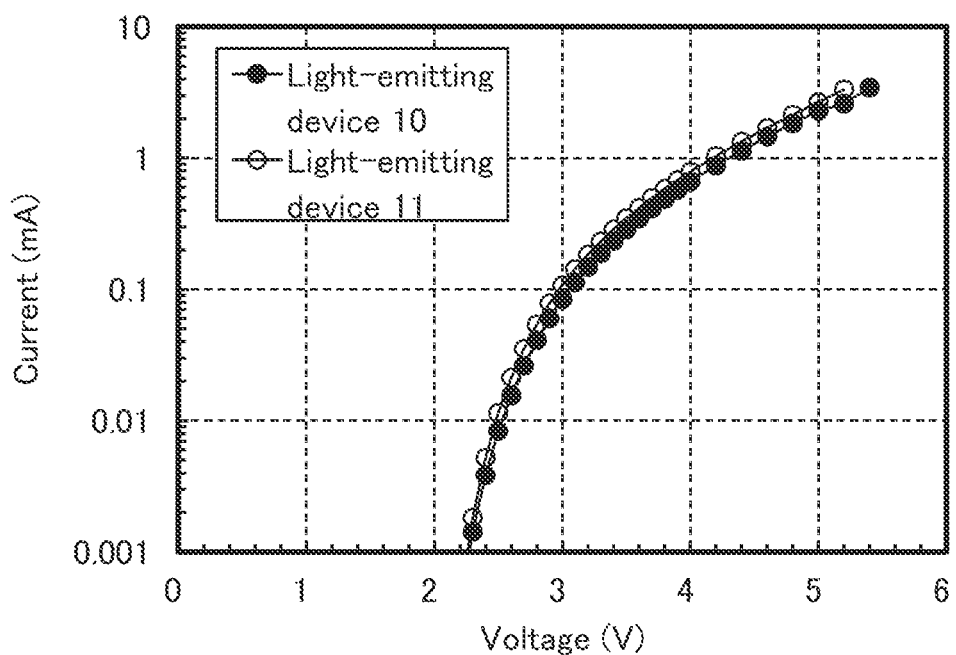
FIG. 61 is a graph showing the current-voltage characteristics of the light-emitting device 10 and the light-emitting device 11.

Next, reliability tests were performed on the light-emitting devices. FIG. 57 shows results of the reliability tests. In FIG. 57, the vertical axis represents normalized luminance (%) with an initial luminance of 100%, and the horizontal axis represents driving time (h) of the devices. Note that in the reliability tests, the light-emitting devices were driven at a constant current of 3 mA.

From the above results of the operation characteristics, the normalized external quantum efficiency and normalized lifetime (LT70) of each of the light-emitting devices were calculated. The results are shown in Table 22. The normalized values were obtained with reference to the values of the comparative light-emitting device c1.

TABLE 22

|  | Host material | Normalized external quantum efficiency | Normalized lifetime (LT90) |
|---|---|---|---|
| Light-emitting device 9 | 8(βN2)-4mDBtPBfpm | 1.034 | 4.300 |
| Comparative light-emitting device c1 | 4,8mDBtP2Bfpm | 1.000 | 1.000 |

TABLE 22-continued

|  | Host material | Normalized external quantum efficiency | Normalized lifetime (LT90) |
|---|---|---|---|
| Comparative light-emitting device c2 | 8βN-4mDBtBPBfpm | 0.876 | 2.182 |

The $T_{H(edge)}$ and the $S'_{H(edge)}$ of a mixed material of PCBBiF and the host material shown in Table 22 that is contained in the light-emitting layer of the corresponding light-emitting device fabricated in this example (an exciplex when the exciplex is formed) and the $T_{D(edge)}$ of the guest material ([Ir(dmpqn)$_2$(acac)]) contained therein were obtained in a manner similar to that of Example 1. The results are shown in Table 23. The $T_{D(edge)}$ of [Ir(dmpqn)$_2$(acac)] is 2.039 eV.

TABLE 23

|  | Host material | $T_{H(edge)}$ [eV] | $T_{H(edge)}$-$T_{D(edge)}$ [eV]* |
|---|---|---|---|
| Light-emitting device 9 | 8(βN2)-4mDBtPBfpm | 2.288 | 0.249 |
| Comparative light-emitting device c1 | 4,8mDBtP2Bfpm | 2.701 | 0.662 |
| Comparative light-emitting device c2 | 8βN-4mDBtBPBfpm | 2.485 | 0.445 |

*$T_{D(edge)}$ = 2.039 [eV] (Absorption edge: 608 nm)

The normalized lifetime of the light-emitting device 9 is longer than those of the comparative light-emitting devices c1 and c2 as shown in Table 22. The value ($S'_{H(edge)}$-$T_{H(edge)}$) of the light-emitting device 9 is estimated to be approximately 0.4 eV; thus, according to the results in Table 23, only the light-emitting device 9 satisfies both the conditions of Formula (1) and Formula (2) shown in Embodiment 1, where the value ($T_{H(edge)}$-$T_{D(edge)}$) is greater than or equal to 0.07 eV and less than or equal to 0.27 eV and the value ($S'_{H(edge)}$-$T_{H(edge)}$) is greater than or equal to 0.2 eV and less than or equal to 0.5 eV; thus, the light-emitting device 9 has a long lifetime.

Reference Synthesis Example 1

Described in this example will be a method for synthesizing 4-[3-(dibenzothiophen-4-yl)phenyl]-8-(naphthalen-2-yl)-[1]benzofuro[3,2-d]pyrimidine (abbreviation: 8βN-4mDBtPBfpm), which is the organic compound used in Example 2. The structural formula of 8βN-4mDBtPBfpm is shown below.

[Chemical Formula 7]

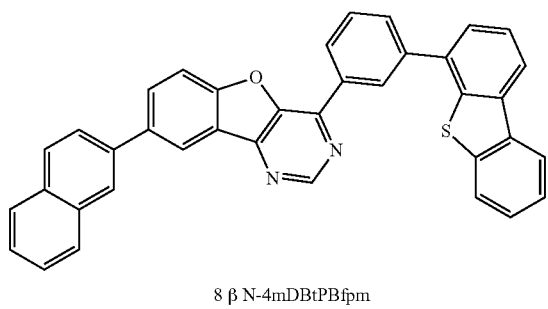

8 β N-4mDBtPBfpm

Synthesis of 4-[3-(dibenzothiophen-4-yl)phenyl]-8-(naphthalen-2-yl)-[1]benzofuro[3,2-d]pyrimidine (Abbreviation: 8βN-4mDBtPBfpm)

First, 1.5 g of 8-chloro-4-[3-(dibenzothiophen-4-yl)phenyl]-[1]benzofuro[3,2-d]pyrimidine, 0.73 g of 2-naphthaleneboronic acid, 1.5 g of cesium fluoride, and 32 mL of mesitylene were put into a 100-mL three-neck flask. The air in the flask was replaced with nitrogen. After adding of 70 mg of 2'-(dicyclohexylphosphino)acetophenone ethylene ketal and 89 mg of tris(dibenzylideneacetone)dipalladium (0) (abbreviation: Pd$_2$(dba)$_3$), the mixture was heated under a nitrogen stream at 120° C. for 5 hours. Water was added to the obtained reaction mixture and filtered, and the residue was washed with water and then with ethanol.

The residue was dissolved in toluene and filtered through a filter aid filled with Celite, alumina, and Celite in this order. The solvent of the obtained solution was concentrated and recrystallized to give 1.5 g of a target pale yellow solid in a yield of 64%. Synthesis Scheme (a-1) is shown below.

[Chemical Formula 8]

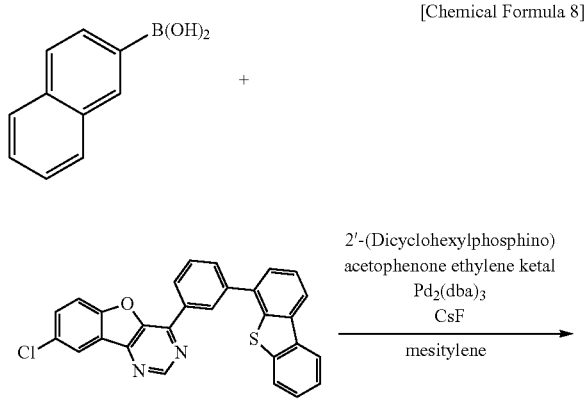

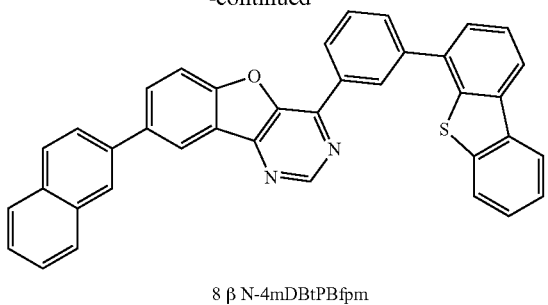

8 β N-4mDBtPBfpm

By a train sublimation method, 1.5 g of the obtained pale yellow solid was purified. In the purification by sublimation, the solid was heated at 290° C. under a pressure of 2.0 Pa with an argon gas flow rate of 10 mL/min. After the purification by sublimation, 0.60 g of a target yellow solid was obtained at a collection rate of 39%.

Analysis results by nuclear magnetic resonance ($^1$H-NMR) spectroscopy of the obtained yellow solid are shown below.

$^1$H-NMR. δ (TCE-d$_2$): 7.45-7.50 (m, 4H), 7.57-7.62 (m, 2H), 7.72-7.93 (m, 8H), 8.03 (d, 1H), 8.10 (s, 1H), 8.17 (d, 2H), 8.60 (s, 1H), 8.66 (d, 1H), 8.98 (s, 1H), 9.28 (s, 1H).

Reference Synthesis Example 2

Described in this example will be a method for synthesizing 8-[3'-(dibenzothiophen-4-yl) (1,1'-biphenyl-3-yl)]naphtho[1',2':4,5]furo[3,2-d]pyrimidine (abbreviation: 8mDBtBPNfpm), which is the organic compound used in Example 2. The structure of 8mDBtBPNfpm is shown below.

[Chemical Formula 9]

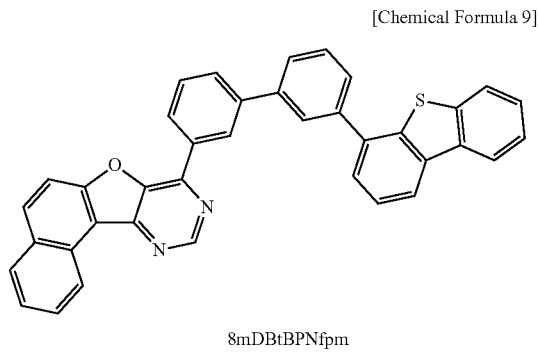 [SMILES: c1cc(-c2cccc(-c3cccc4c3sc3ccccc34)c2)cc(-c2ncnc3c2oc2ccc4ccccc4c23)c1]

8mDBtBPNfpm

Step 1: Synthesis of ethyl 1-amino-naphtho[2,1-b]furan-2-carboxylate

First, 4.0 g of 2-hydroxynaphthalene-1-carbonitrile and 6.6 g of potassium carbonate were put into a flask, the air in the flask was replaced with nitrogen, 30 mL of DMF and 4.0 g of ethyl bromoacetate were added, and the mixture was heated at 80° C. for 16 hours. The obtained reaction mixture was added to 100 mL of iced water for rapid cooling, the mixture was stirred for 1 hour, and then filtered. The obtained residue was washed with water, and recrystallized with ethanol and water, whereby 4.4 g of a target substance (brown solid) was obtained in a yield of 72%. Synthesis Scheme (b-1) of Step 1 is shown below.

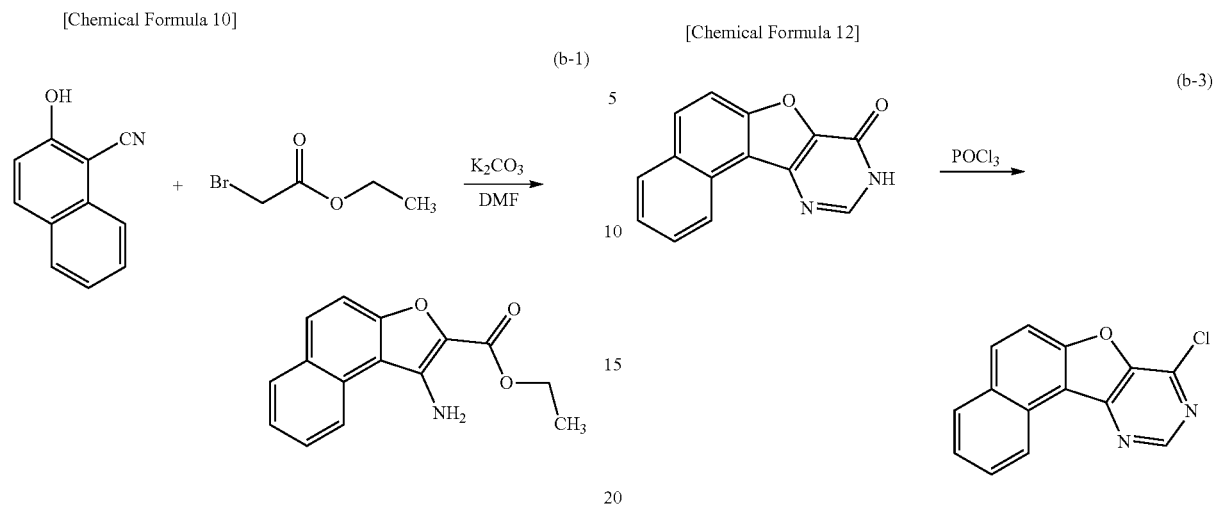

Step 2: Synthesis of Naphtho[1',2':4,5]furo[3,2-d]pyrimidin-8(9H)-one

Next, 4.4 g of ethyl 1-amino-naphtho[2,1-b]furan-2-carboxylate synthesized in Step 1, 1.8 g of formamidine acetate, and 25 mL of formamide were put into a flask, and the mixture was heated at 160° C. for 8 hours. To the obtained reaction mixture was added 100 mL of water and the mixture was filtered. The residue was washed with water to give 3.9 g of a target substance (brown solid) in a yield of 96%. Synthesis Scheme (b-2) of Step 2 is shown below.

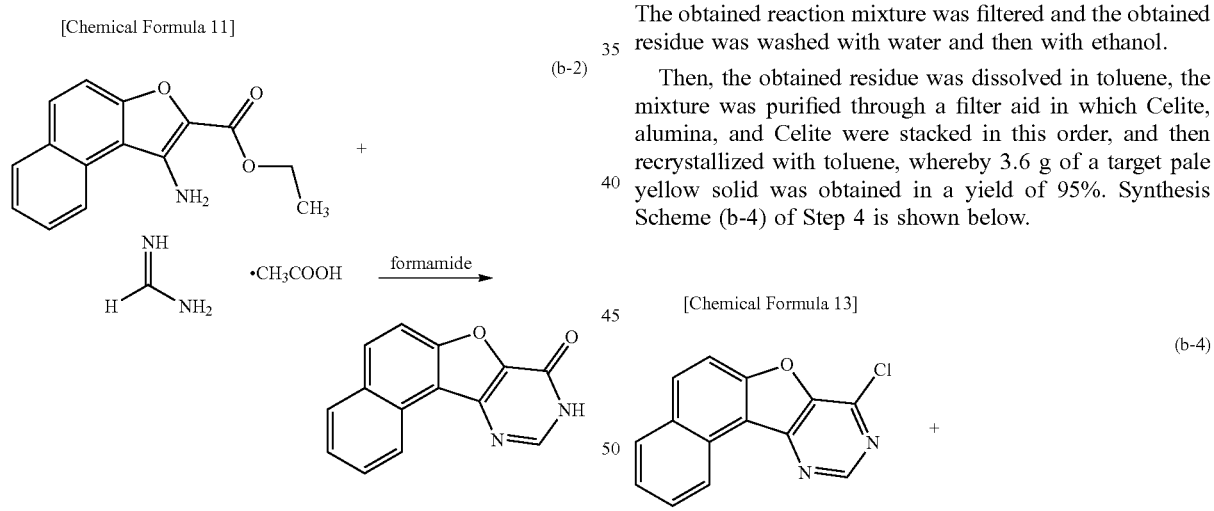

Step 3: Synthesis of 8-chloro-naphtho[1',2':4,5]furo[3,2-d]pyrimidine

Next, 3.9 g of naphtho[1',2':4,5]furo[3,2-d]pyrimidin-8(9H)-one synthesized in Step 2 and 15 mL of phosphoryl chloride were put into a flask, and the mixture was heated under a nitrogen stream at 100° C. for 6 hours. The obtained reaction mixture was added to 100 mL of iced water for rapid cooling, 330 mL of a 3M sodium hydroxide aqueous solution was added, and the mixture was stirred for 1 hour. This mixture was filtered and the residue was washed with ethanol to give 1.8 g of a target substance (yellow solid) in a yield of 42%. Synthesis Scheme (b-3) of Step 3 is shown below.

Step 4: Synthesis of 8mDBtBPNfpm

Next, 1.8 g of 8-chloro-naphtho[1',2':4,5]furo[3,2-d]pyrimidine synthesized in Step 3, 2.9 g of 3-(dibenzothiophen-4-yl)phenylboronic acid, 15 mL of a 2M potassium carbonate aqueous solution, 150 mL of toluene, and 15 mL of ethanol were put into a flask, and the air in the flask was replaced with nitrogen. To this mixture was added 0.29 g of tetrakis(triphenylphosphine)palladium(0), and the mixture was heated under a nitrogen stream at 95° C. for 12 hours. The obtained reaction mixture was filtered and the obtained residue was washed with water and then with ethanol.

Then, the obtained residue was dissolved in toluene, the mixture was purified through a filter aid in which Celite, alumina, and Celite were stacked in this order, and then recrystallized with toluene, whereby 3.6 g of a target pale yellow solid was obtained in a yield of 95%. Synthesis Scheme (b-4) of Step 4 is shown below.

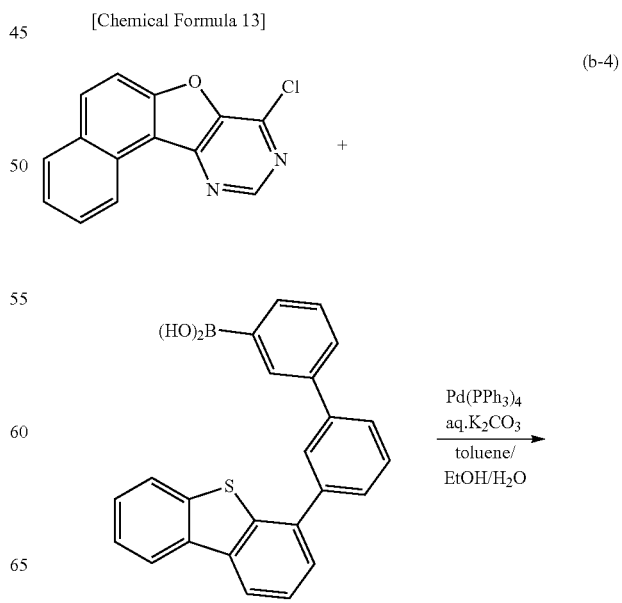

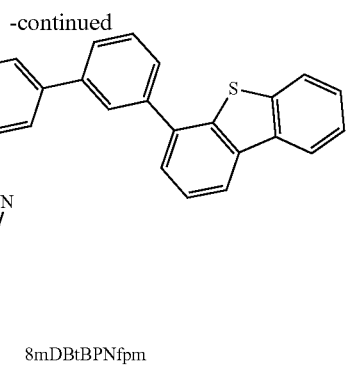

8mDBtBPNfpm

By a train sublimation method, 3.6 g of the obtained pale yellow solid was purified. In the purification by sublimation, the pale yellow solid was heated at 310° C. under a pressure of 2.7 Pa with an argon flow rate of 5 mL/min. After the purification by sublimation, 2.7 g of a pale yellow solid was obtained at a collection rate of 73%.

Analysis results by nuclear magnetic resonance ($^1$H-NMR) spectroscopy of the obtained pale yellow solid are shown below.

$^1$H-NMR. δ (TCE-$d_2$): 7.45-7.52 (m, 2H), 7.60-7.71 (m, 4H), 7.74-7.86 (m, 6H), 7.92 (d, 1H), 8.05 (d, 1H), 8.12 (d, 1H), 8.16 (s, 1H), 8.19-8.22 (m, 2H), 8.64 (d, 1H), 8.96 (s, 1H), 9.23 (d, 1H), 9.32 (s, 1H).

Reference Synthesis Example 3

A method for synthesizing 9-[(3'-dibenzothiophen-4-yl)biphenyl-3-yl]naphtho[1',2':4,5]furo[2,3-b]pyrazine (abbreviation: 9mDBtBPNfpr), which is the organic compound used in Example 3, will be described. The structure of 9mDBtBPNfpr is shown below.

[Chemical Formula 14]

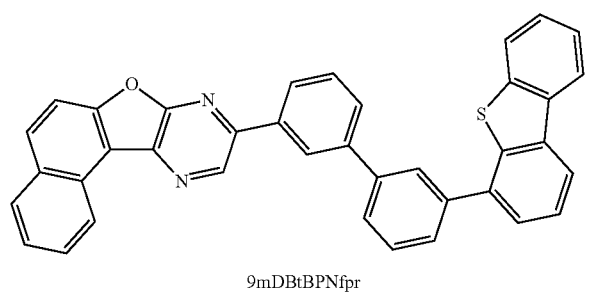

9mDBtBPNfpr

Step 1: Synthesis of 6-chloro-3-(2-methoxynaphthalen-1-yl)pyrazin-2-amine

First, into a three-neck flask equipped with a reflux pipe were put 4.37 g of 3-bromo-6-chloropyrazin-2-amine, 4.23 g of 2-methoxynaphthalene-1-boronic acid, 4.14 g of potassium fluoride, and 75 mL of dehydrated tetrahydrofuran, and the air in the flask was replaced with nitrogen. The mixture in the flask was degassed by being stirred under reduced pressure, and then 0.57 g of tris(dibenzylideneacetone)dipalladium(0) (abbreviation: Pd$_2$(dba)$_3$) and 4.5 mL of tri-tert-butylphosphine (abbreviation: P(tBu)$_3$) were added thereto. The mixture was stirred at 80° C. for 54 hours to be reacted.

After a certain period of time, the obtained mixture was subjected to suction filtration and the filtrate was concentrated. Then, purification by silica gel column chromatography using toluene:ethyl acetate=9:1 as a developing solvent was performed, so that 2.19 g of a target pyrazine derivative (yellowish white powder) was obtained in a yield of 36%. Synthesis Scheme (c-1) of Step 1 is shown below.

[Chemical Formula 15]

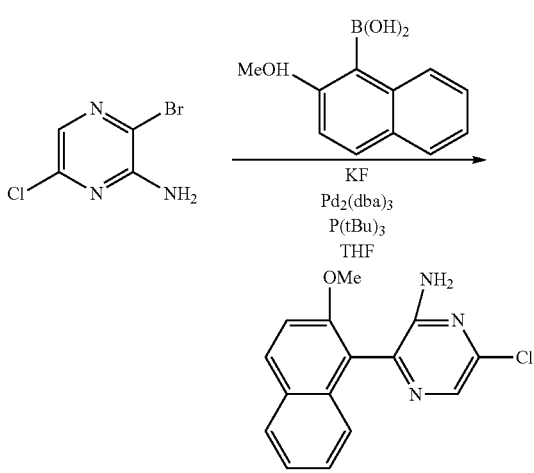

(c-1)

Step 2: Synthesis of 9-chloronaphtho[1',2':4,5]furo[2,3-b]pyrazine

Next, into a three-neck flask were put 2.18 g of 6-chloro-3-(2-methoxynaphthalen-1-yl)pyrazin-2-amine obtained in Step 1, 63 mL of dehydrated tetrahydrofuran, and 84 mL of a glacial acetic acid, and the air in the flask was replaced with nitrogen. After the flask was cooled down to −10° C., 2.8 mL of tert-butyl nitrite was dripped, and the mixture was stirred at −10° C. for 30 minutes and at 0° C. for 3 hours. After a certain period of time, 250 mL of water was added to the obtained suspension and suction filtration was performed, so that 1.48 g of a target pyrazine derivative (yellowish white powder) was obtained in a yield of 77%. Synthesis Scheme (c-2) of Step 2 is shown below.

[Chemical Formula 16]

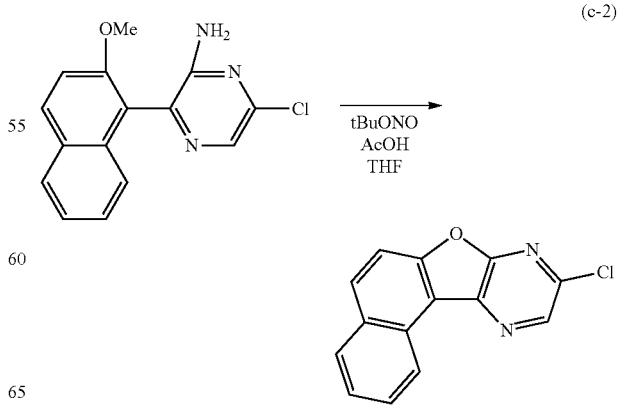

(c-2)

Step 3: Synthesis of 9-[(3'-dibenzothiophen-4-yl)biphenyl-3-yl]naphtho[1',2':4,5]furo[2,3-b]pyrazine
(Abbreviation: 9mDBtBPNfpr)

Into a three-neck flask were put 1.48 g of 9-chloronaphtho[1',2':4,5]furo[2,3-b]pyrazine obtained in Step 2, 3.41 g of 3'-(4-dibenzothiophene)-1,1'-biphenyl-3-boronic acid, 8.8 mL of a 2M potassium carbonate aqueous solution, 100 mL of toluene, and 10 mL of ethanol, and the air in the flask was replaced with nitrogen. The mixture in the flask was degassed by being stirred under reduced pressure, and then 0.84 g of bis(triphenylphosphine)palladium(II) dichloride (abbreviation: $Pd(PPh_3)_2Cl_2$) was added thereto. The mixture was stirred at 80° C. for 18 hours to be reacted.

After a certain period of time, the obtained suspension was subjected to suction filtration and was washed with water and ethanol. The obtained solid was dissolved in toluene, and the mixture was filtered through a filter aid in which Celite, alumina, and Celite were stacked in this order and was recrystallized with a mixed solvent of toluene and hexane, so that 2.66 g of a target pale yellow solid was obtained in a yield of 82%.

By a train sublimation method, 2.64 g of the obtained pale yellow solid was purified. In the purification by sublimation, the solid was heated at 315° C. under a pressure of 2.6 Pa with an argon gas flow rate of 15 mL/min. After the purification by sublimation, 2.34 g of a target pale yellow solid was obtained in a yield of 89%. Synthesis Scheme (c-3) of Step 3 is shown below.

Analysis results by nuclear magnetic resonance ($^1$H-NMR) spectroscopy of the pale yellow solid obtained in Step 3 are shown below.

$^1$H-NMR. δ ($CD_2Cl_2$): 7.47-7.51 (m, 2H), 7.60-7.69 (m, 5H), 7.79-7.89 (m, 6H), 8.05 (d, 1H), 8.10-8.11 (m, 2H), 8.18-8.23 (m, 3H), 8.53 (s, 1H), 9.16 (d, 1H), 9.32 (s, 1H).

Example 5

In this example, the case will be described in which light-emitting devices using a guest material that emits light having a long wavelength were fabricated in a manner similar to that of the light-emitting device described in Example 3. Note that bis{4,6-dimethyl-2-[5-(4-cyano-2-methylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-mCP)$_2$(dpm)]) was used as a guest material in this example. The device structure of the light-emitting device described in this example is illustrated in FIG. 15, and a fabrication method thereof is similar to that in Example 2.

The chemical formulae of materials used in the light-emitting devices in this example are shown below. Specific structures of the light-emitting devices are shown in Table 24 below.

[Chemical Formula 17]

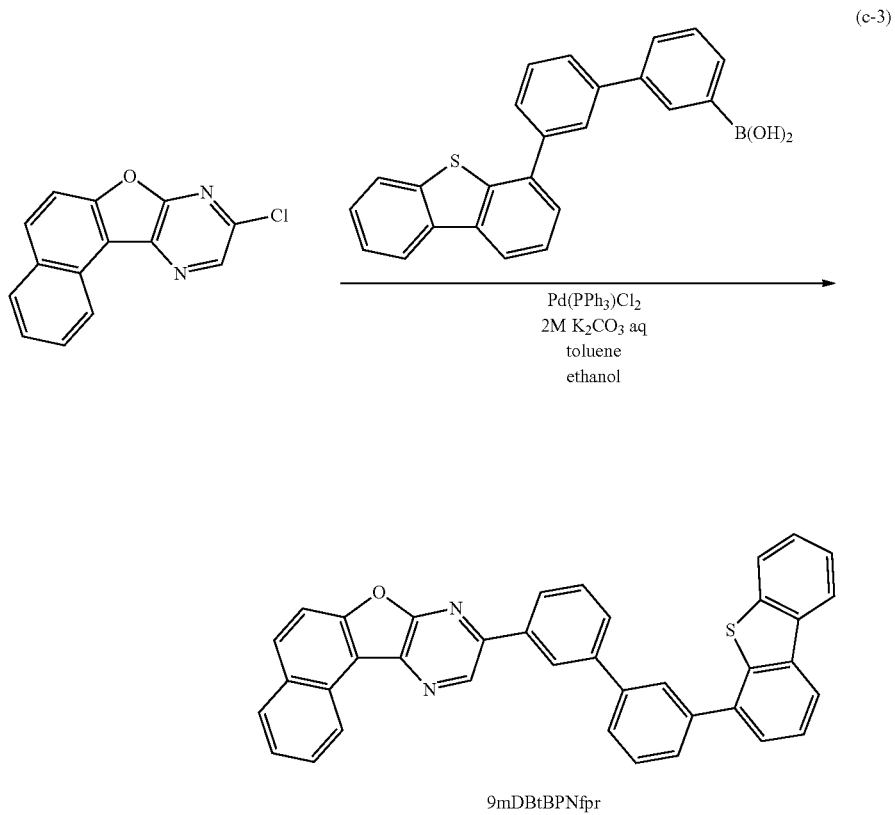

9mDBtBPNfpr

[Chemical Formula 18]
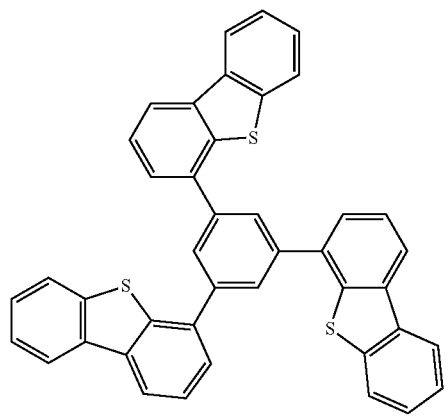
DBT3P-II
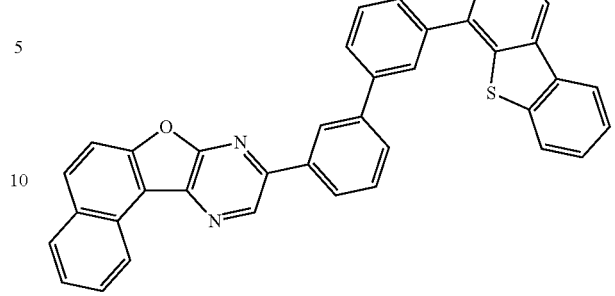
9mDBtBPNfpr
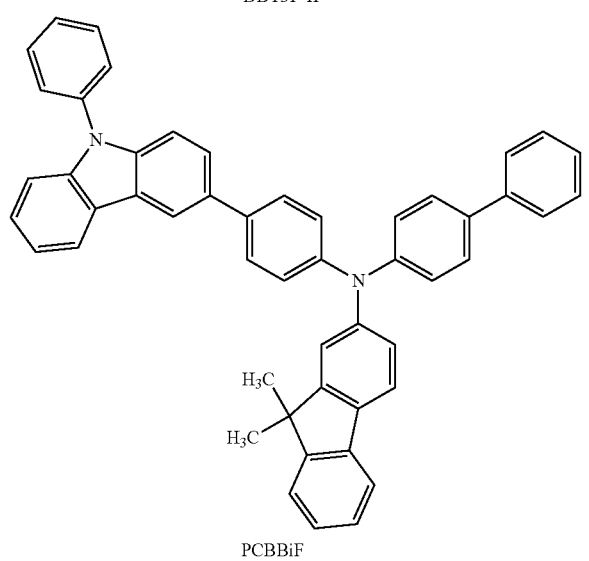
PCBBiF
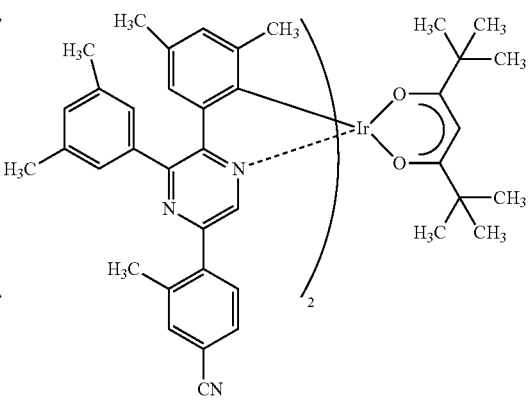
[Ir(dmdppr-mCP)$_2$(dpm)]
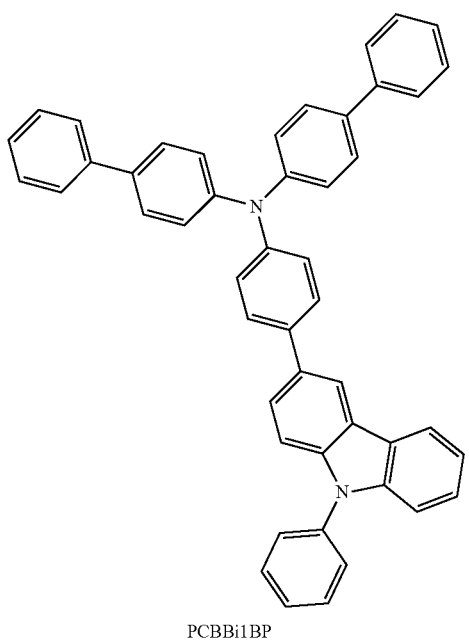
PCBBi1BP
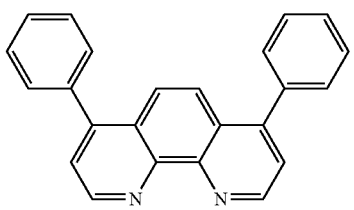
Bphen

TABLE 24

| | First electrode | Hole-injection layer | Hole-transport layer | Light-emitting layer | Electron-transport layer | Electron-injection layer | Second electrode |
|---|---|---|---|---|---|---|---|
| Light-emitting device 10 | ITSO (70 nm) | DBT3P-II:MoOx (2:1 70 nm) | PCBBi1BP (20 nm) | * | 9mDBtBPNfpr (30 nm) | NBphen (15 nm) | LiF (1 nm) | Al (200 nm) |
| Light-emitting device 11 | | | | ** | | | |

* 9mDBtBPNfpr:PCBBiF:[Ir(dmdppr-mCP)$_2$(dpm)] (0:8:0.2:0.1 40 nm)
** 9mDBtBPNfpr:PCBBiF:[Ir(dmdppr-mCP)$_2$(dpm)] (0.8:0.2:0.05 40 nm)

Note that PCBBi1BP in Table 24 is an abbreviation for 4,4'-diphenyl-4"-(9-phenyl-9H-carbazol-3-yl)triphenylamine, and 9mDBtBNfpr is an abbreviation for 9-[(3'-dibenzothiophen-4-yl)biphenyl-3-yl]naphtho[1',2':4,5]furo[2,3-b]pyrazine.

<<Operation Characteristics of Light-Emitting Devices>>

The operation characteristics of a light-emitting device 10 and a light-emitting device 11 that were fabricated were measured at room temperature. The results are shown in FIG. 58 to FIG. 61.

Table 25 shows the initial values of main characteristics of the light-emitting devices at around 1000 cd/m$^2$.

TABLE 25

| | Voltage (V) | Current (mA) | Current density (mA/cm$^2$) | Chromaticity (x, y) | Luminance (cd/m$^2$) | Current efficiency (cd/A) | Power efficiency (lm/W) | External quantumn efficiency (%) |
|---|---|---|---|---|---|---|---|---|
| Light-emitting device 10 | 3.7 | 0.41 | 10.0 | (0.71, 0.29) | 1000 | 9.9 | 8.4 | 26 |
| Light-emitting device 11 | 3.5 | 0.35 | 8.7 | (0.70, 0.30) | 980 | 11 | 10 | 27 |

Figure 62:
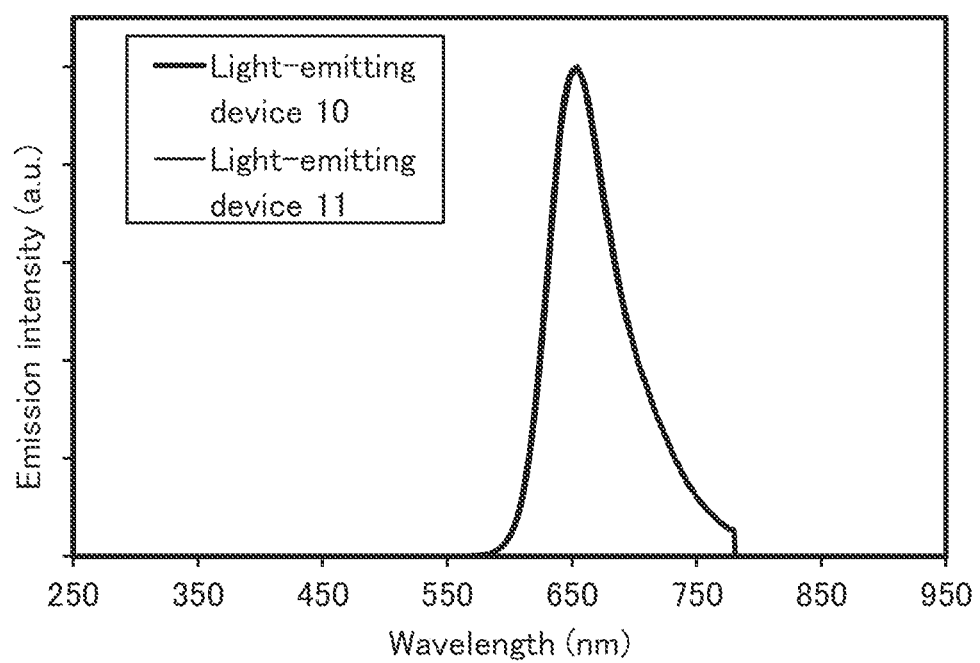
FIG. 62 shows the emission spectra of the light-emitting device 10 and the light-emitting device 11.

FIG. 62 shows emission spectra when a current with a density of 2.5 mA/cm$^2$ was supplied to each of the light-emitting devices. As shown in FIG. 62, the emission spectra of the light-emitting devices 10 and 11 have a peak at around 654 nm and a peak at around 652 nm, respectively, which are presumably derived from light emission of [Ir(dmdppr-mCP)$_2$(dpm)] contained in the light-emitting layer 913. The measurement results of the external quantum efficiencies show that both the light-emitting devices have high efficiency.

Figure 63:
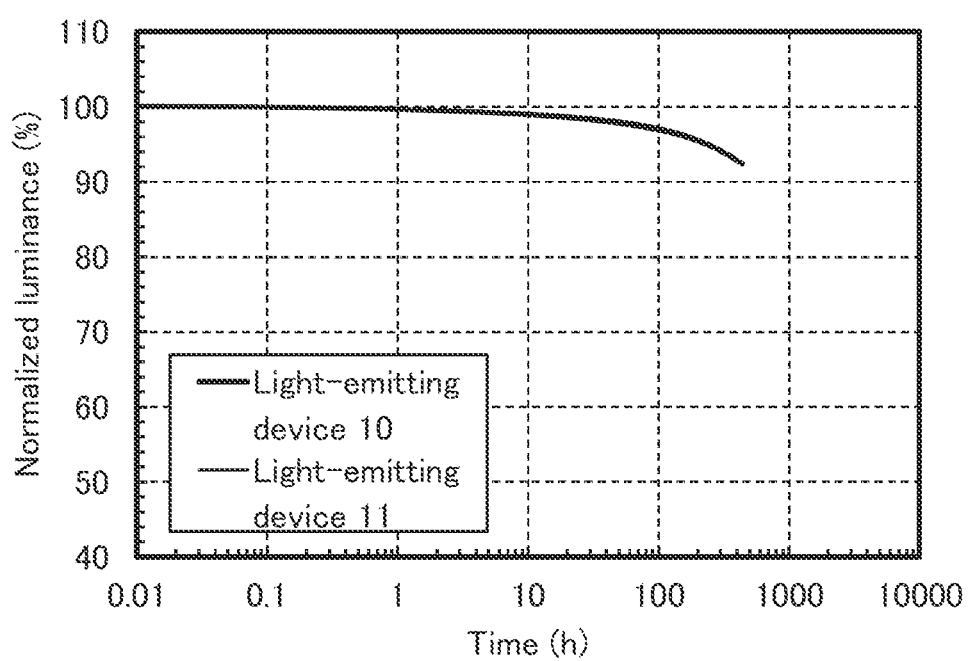
FIG. 63 is a graph showing the reliabilities of the light-emitting device 10 and the light-emitting device 11.

Next, reliability tests were performed on the light-emitting devices. FIG. 63 shows results of the reliability tests. In FIG. 63, the vertical axis represents normalized luminance (%) with an initial luminance of 100%, and the horizontal axis represents driving time (h) of the devices. Note that in the reliability tests, the light-emitting devices were driven at a constant current of 3 mA (75 mA/cm$^2$).

According to the results of the above operation characteristics, the lifetimes (LT95) of the light-emitting devices 10 and 11 were 235 hours and 252 hours, respectively. Although the light-emitting devices were driven at a current density as high as 75 mA/cm$^2$, the light-emitting devices each had a significantly long lifetime.

The T$_{H(edge)}$ and the S'$_{H(edge)}$ of a mixed material of PCBBiF and 9mDBtBPNfpr that is contained in the light-emitting layer of the corresponding light-emitting device fabricated in this example (an exciplex when the exciplex is formed) and the T$_{D(edge)}$ of the guest material ([Ir(dmdppr-mCP)$_2$(dpm)]) contained therein were obtained in a manner similar to that of Example 1. The results are shown in Table 26. The T$_{D(edge)}$ of [Ir(dmdppr-mCP)$_2$(dpm)] is 1.953 eV.

TABLE 26

| | Host material | T$_{H(edge)}$ [eV] | T$_{H(edge)}$-T$_{D(edge)}$ [eV]* | S'$_{H(edge)}$ [eV] | S'$_{H(edge)}$-T$_{H(edge)}$ [eV] |
|---|---|---|---|---|---|
| Light-emitting devices 10 and 11 | 9mDBtBPNfpr | 2.175 | 0.222 | 2.583 | 0.408 |

*T$_{D(edge)}$ = 1.953 [eV] (Absorption edge: 635 nm)

The light-emitting devices 10 and 11 each have high emission efficiency and a long lifetime. According to the results in Table 26, each of the light-emitting devices 10 and 11 satisfies both the conditions of Formula (1) and Formula (2) shown in Embodiment 1, where the value ($T_{H(edge)}-T_{D(edge)}$) is greater than or equal to 0.07 eV and less than or equal to 0.27 eV and the value ($S'_{H(edge)}-T_{H(edge)}$) is greater than or equal to 0.2 eV and less than or equal to 0.5 eV; thus, the light-emitting devices 10 and 11 each have a long lifetime.

Reference Synthesis Example 4

Described in this example will be a method for synthesizing bis{4,6-dimethyl-2-[5-(4-cyano-2-methylphenyl)-3-(3,5-dimethylphenyl)-2-pyrazinyl-κN]phenyl-κC}(2,2,6,6-tetramethyl-3,5-heptanedionato-κ²O,O')iridium(III) (abbreviation: [Ir(dmdppr-mCP)₂(dpm)]), which is the organometallic complex used in Example 5. The structure of [Ir(dmdppr-mCP)₂(dpm)] is shown below.

that 1.16 g of a target pyrazine derivative Hdmdppr-mCP (abbreviation) (white solid) was obtained in a yield of 65%. Synthesis Scheme (d-1) of Step 1 is shown below.

[Chemical Formula 20]

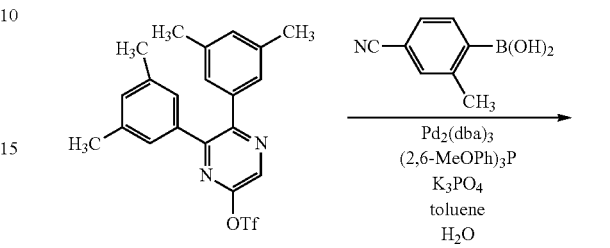

d-1

[Chemical Formula 19]

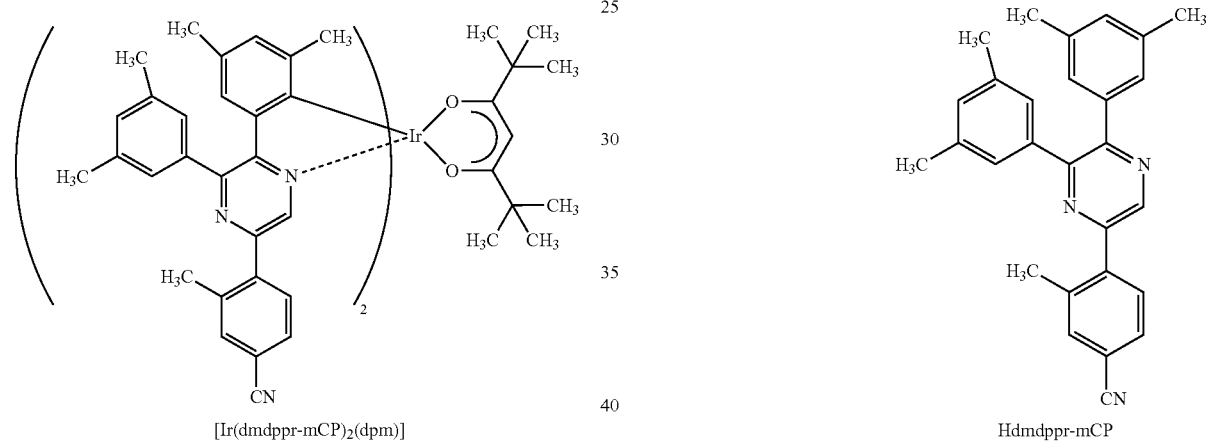

[Ir(dmdppr-mCP)₂(dpm)]

Hdmdppr-mCP

Step 1: Synthesis of 5-(4-cyano-2-methylphenyl)-2,3-bis(3,5-dimethylphenyl)pyrazine (Abbreviation: Hdmdppr-mCP)

First, 1.97 g of 5,6-bis(3,5-dimethylphenyl)pyrazin-2-yl trifluoromethanesulfonate, 0.89 g of 4-cyano-2-methylphenylboronic acid, 3.48 g of tripotassium phosphate, 37 mL of toluene, and 3.7 mL of water were put into a three-neck flask, and the air in the flask was replaced with nitrogen. The mixture in the flask was degassed by being stirred under reduced pressure, 0.042 g of tris(dibenzylideneacetone)dipalladium(0) and 0.082 g of tris(2,6-dimethoxyphenyl)phosphine were added thereto, and the mixture was refluxed for 7 hours. After a certain period of time, extraction was performed with toluene. Then, purification by silica gel column chromatography using hexane:ethyl acetate=5:1 (volume ratio) as a developing solvent was performed, so Step 2: Synthesis of di-μ-chloro-tetrakis{4,6-dimethyl-2-[5-(4-cyano-2-methylphenyl)-3-(3,5-dimethylphenyl)-2-pyrazinyl-κN]phenyl-κC}diiridium(III) (Abbreviation: [Ir(dmdppr-mCP)₂Cl]₂)

Next, 15 mL of 2-ethoxyethanol, 5 mL of water, 1.16 g of Hdmdppr-mCP (abbreviation) obtained in Step 1 described above, and 0.42 g of iridium chloride hydrate (IrCl₃·H₂O) (produced by Furuya Metal Co., Ltd.) were put into a recovery flask equipped with a reflux pipe, and the air in the flask was replaced with argon. After that, the mixture was irradiated with microwaves (2.45 GHz, 100 W) for 2 hours to cause a reaction. After a certain period of time, the obtained residue was suction-filtered and washed with methanol to give 1.12 g of a dinuclear complex [Ir(dmdppr-mCP)₂Cl]₂ (orange-brown solid) in a yield of 76%. Synthesis Scheme (d-2) of Step 2 is shown below.

[Chemical Formula 21]

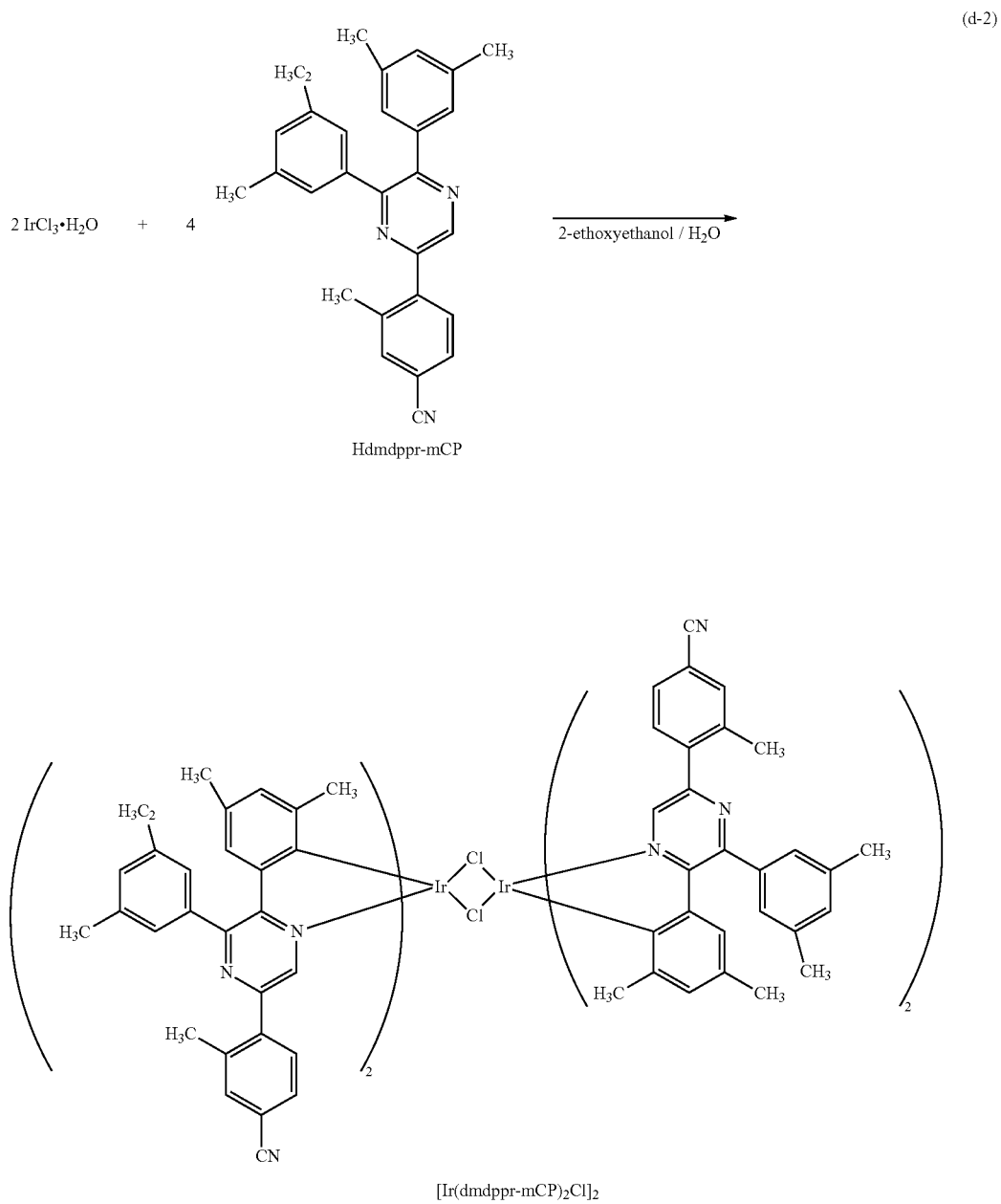

Step 3: Synthesis of [Ir(dmdppr-mCP)₂(dpm)]

Furthermore, 20 mL of 2-ethoxyethanol, 1.11 g of [Ir(dmdppr-mCP)₂Cl]₂ (abbreviation), which is the dinuclear complex obtained in Step 2 described above, 0.29 g of dipivaloylmethane (abbreviation: Hdpm), and 0.56 g of sodium carbonate were put into a recovery flask equipped with a reflux pipe, and the air in the flask was replaced with argon. After that, the mixture was irradiated with microwaves (2.45 GHz, 100 W) for 2 hours to cause a reaction. The solvent was distilled off, the obtained residue was purified by silica gel column chromatography using dichloromethane as a developing solvent, and then recrystallization was performed with a mixed solvent of dichloromethane and methanol to give 0.60 g of the organometallic complex [Ir(dmdppr-mCP)₂(dpm)] as a dark red solid in a yield of 48%.

By a train sublimation method, 0.60 g of the obtained dark red solid was purified. In the purification by sublimation, the solid was heated at 315° C. under a pressure of 2.6 Pa with an argon gas flow rate of 10.5 mL/min. After the purification by sublimation, 0.48 g of a target dark red solid was obtained in a yield of 80%. Synthesis Scheme (d-3) of Step 3 is shown below.

[Chemical Formula 22]
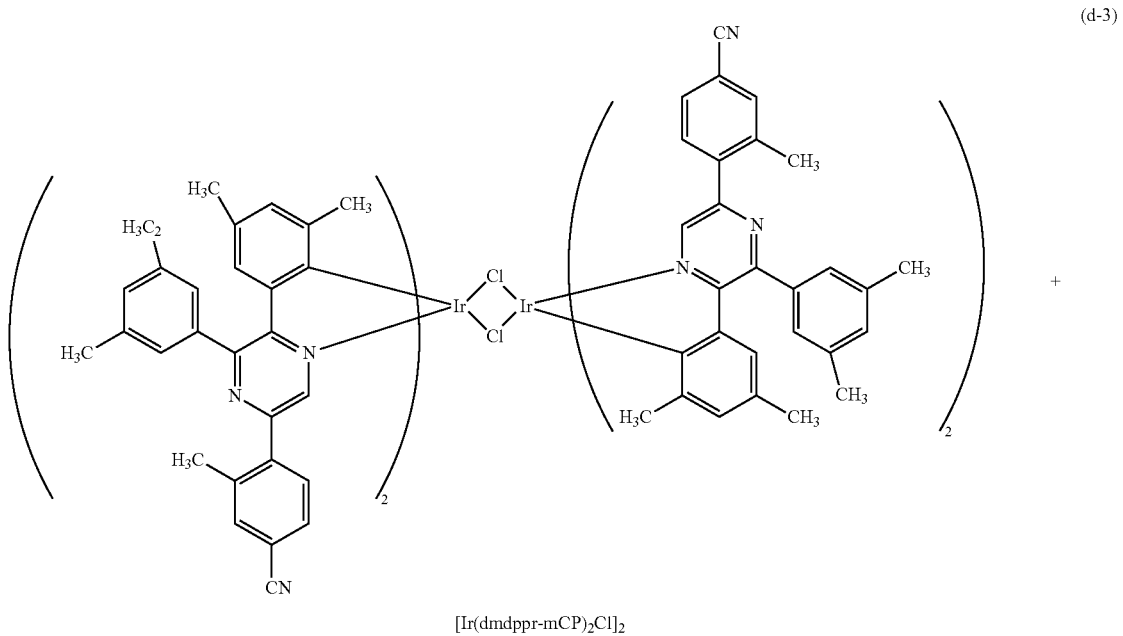
[Ir(dmdppr-mCP)₂Cl]₂
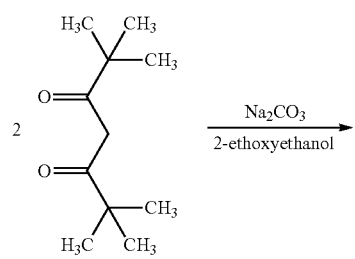
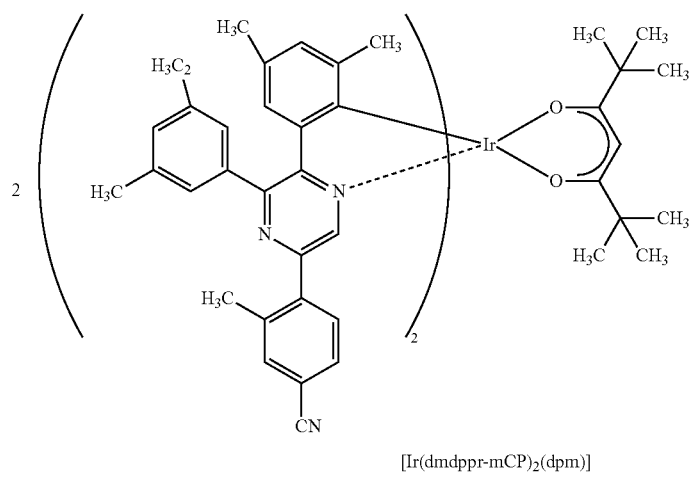
[Ir(dmdppr-mCP)₂(dpm)]

Figure 64:
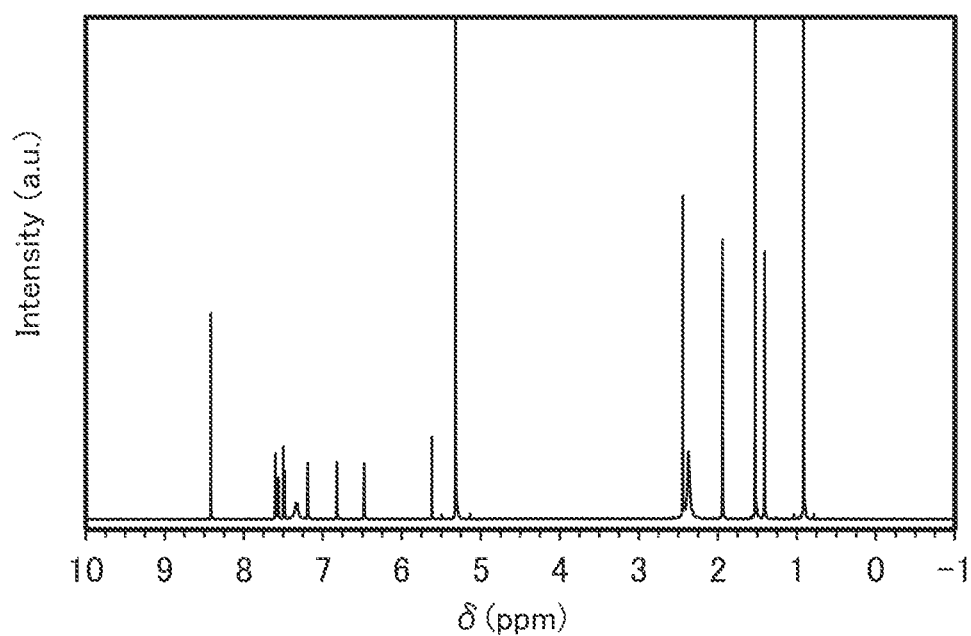
FIG. 64 is the $^1$H-NMR chart of an organic compound [Ir(dmdppr-mCP)$_2$(dpm)].

Note that results of the analysis by nuclear magnetic resonance spectrometry ($^1$H-NMR) of the dark red solid obtained in Step 3 are shown below. The $^1$H-NMR chart is shown in FIG. 64. These results reveal that [Ir(dmdppr-mCP)$_2$(dpm)], the organometallic complex represented by Structural Formula (101), was obtained.

$^1$H-NMR. δ (CD$_2$Cl$_2$): 0.91 (s, 18H), 1.41 (s, 6H), 1.94 (s, 6H), 2.37 (s, 12H), 2.45 (s, 6H), 5.62 (s, 1H), 6.48 (s, 2H), 6.82 (s, 2H), 7.19 (s, 2H), 7.36 (s, 4H), 7.49 (d, 2H), 7.57 (d, 2H), 7.60 (s, 2H), 8.42 (s, 2H).

Reference Synthesis Example 5

A synthesis method of bis {4,6-dimethyl-2-[5-(3-cyano-2-methylphenyl)-3-(3,5-dimethylphenyl)-2-pyrazinyl-κN]phenyl-κC}(2,2,6,6-tetramethyl-3,5-heptanedionato-κ²O,O')iridium(III) (abbreviation: [Ir(dmdppr-m3 CP)$_2$(dpm)]), the organometallic complex that can be used in the light-emitting device of one embodiment of the present invention, will be described. The structure of [Ir(dmdppr-m3CP)$_2$(dpm)] is shown below.

[Chemical Formula 23]

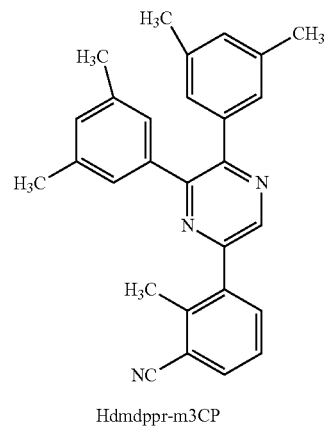

[Ir(dmdppr-m3CP)$_2$(dpm)]

that 1.57 g of a target pyrazine derivative Hdmdppr-m3CP (abbreviation) (white solid) was obtained in a yield of 80%. Synthesis Scheme (e-1) of Step 1 is shown below.

[Chemical Formula 24]

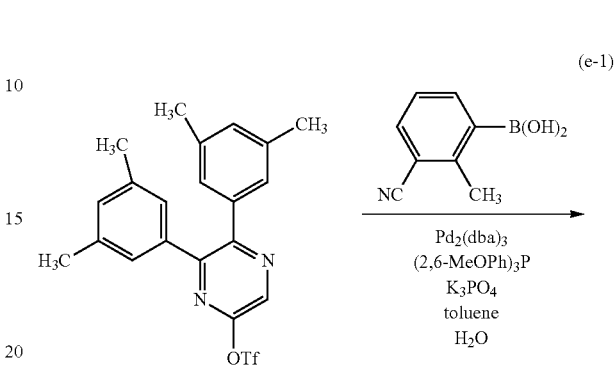

Hdmdppr-m3CP

Step 1: Synthesis of 5-(3-cyano-2-methylphenyl)-2,3-bis(3,5-dimethylphenyl)pyrazine (Abbreviation: Hdmdppr-m3CP)

First, 2.15 g of 5,6-bis(3,5-dimethylphenyl)pyrazin-2-yl trifluoromethanesulfonate, 0.95 g of 3-cyano-2-methylphenylboronic acid, 3.76 g of tripotassium phosphate, 40 mL of toluene, and 4.0 mL of water were put into a three-neck flask, and the air in the flask was replaced with nitrogen. The mixture in the flask was degassed by being stirred under reduced pressure, 0.045 g of tris(dibenzylideneacetone)dipalladium(0) and 0.087 g of tris(2,6-dimethoxyphenyl)phosphine were added thereto, and the mixture was refluxed for 7.5 hours. After a certain period of time, extraction was performed with toluene. Then, purification by silica gel column chromatography using hexane:ethyl acetate=5:1 (volume ratio) as a developing solvent was performed, so Step 2: Synthesis of di-μ-chloro-tetrakis{4,6-dimethyl-2-[5-(3-cyano-2-methylphenyl)-3-(3,5-dimethylphenyl)-2-pyrazinyl-κN]phenyl-κC}diiridium(III) (Abbreviation: [Ir(dmdppr-m3 CP)$_2$Cl]$_2$)

Next, 15 mL of 2-ethoxyethanol, 5 mL of water, 1.57 g of Hdmdppr-m3CP (abbreviation) obtained in Step 1 described above, and 0.57 g of iridium chloride hydrate (IrCl$_3$·H$_2$O) (produced by Furuya Metal Co., Ltd.) were put into a recovery flask equipped with a reflux pipe, and the air in the flask was replaced with argon. After that, the mixture was irradiated with microwaves (2.45 GHz, 100 W) for 2 hours to cause a reaction. After a certain period of time, the obtained residue was suction-filtered and washed with methanol to give 1.44 g of a dinuclear complex [Ir(dmdppr-m3CP)$_2$Cl]$_2$ (abbreviation) (reddish orange solid) in a yield of 73%. Synthesis Scheme (e-2) of Step 2 is shown below.

[Chemical Formula 25]

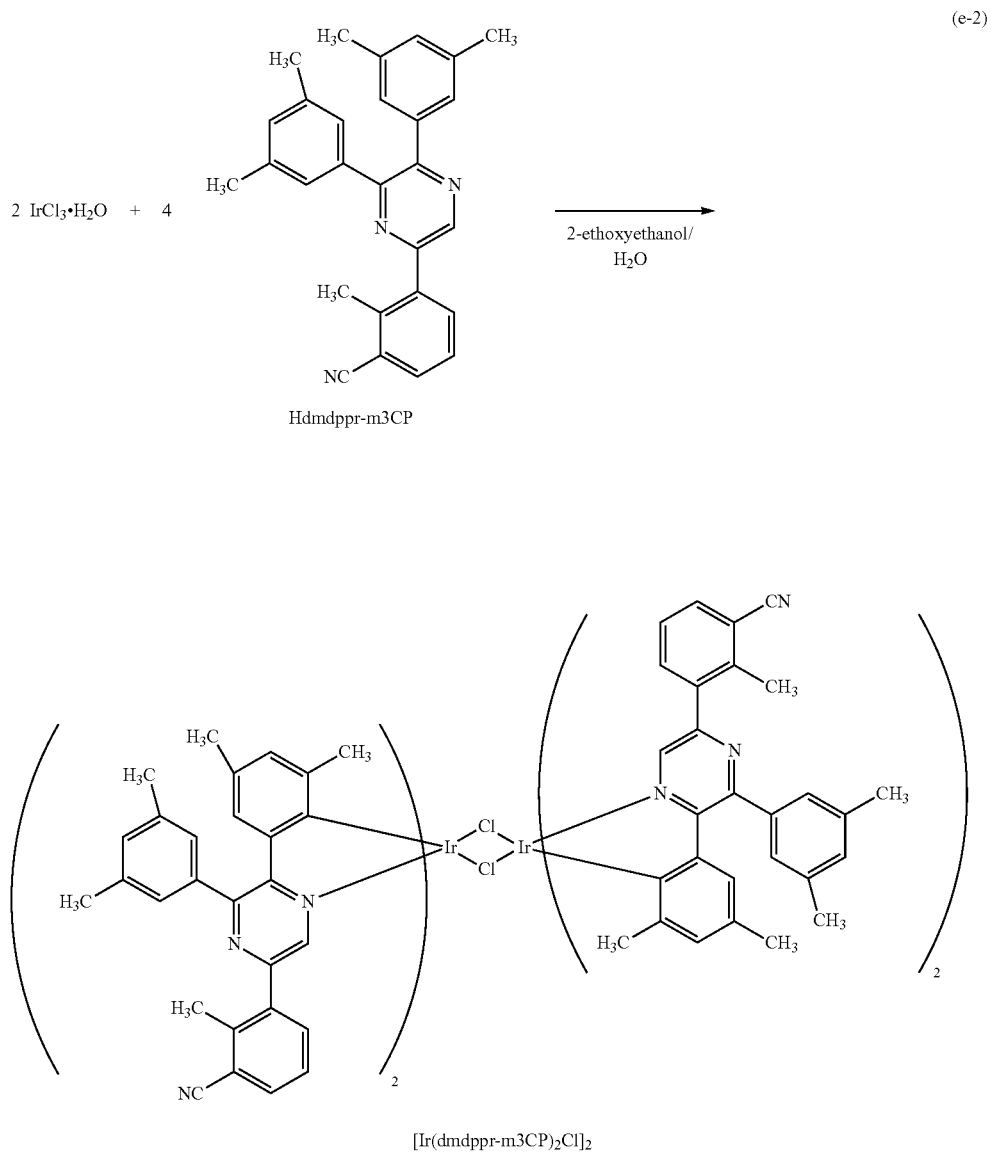

Step 3: Synthesis of bis{4,6-dimethyl-2-[5-(3-cyano-2-methylphenyl)-3-(3,5-dimethylphenyl)-2-pyrazinyl-κN]phenyl-κC}(2,2,6,6-tetramethyl-3,5-heptanedionato-κ²O,O')iridium(III) (Abbreviation: [Ir(dmdppr-m3CP)₂(dpm)])

Furthermore, 20 mL of 2-ethoxyethanol, 1.44 g of [Ir(dmdppr-m3CP)₂Cl]₂ (abbreviation), which is the dinuclear complex obtained in Step 2 described above, 0.39 g of dipivaloylmethane (abbreviation: Hdpm), and 0.74 g of sodium carbonate were put into a recovery flask equipped with a reflux pipe, and the air in the flask was replaced with argon. After that, the mixture was irradiated with microwaves (2.45 GHz, 100 W) for 2 hours to cause a reaction. The solvent was distilled off, the obtained residue was purified by silica gel column chromatography using dichloromethane as a developing solvent, and then recrystallization was performed with a mixed solvent of dichloromethane and methanol to give 1.01 g of [Ir(dmdppr-m3CP)₂(dpm)] (abbreviation) (dark red solid) in a yield of 61%. By a train sublimation method, 0.96 g of the obtained dark red solid was purified. In the purification by sublimation, the solid was heated at 305° C. under a pressure of 2.6 Pa with an argon gas flow rate of 10.5 mL/min. After the purification by sublimation, 0.71 g of a target dark red solid was obtained in a yield of 74%. Synthesis Scheme (e-3) of Step 3 is shown below.

[Chemical Formula 26]

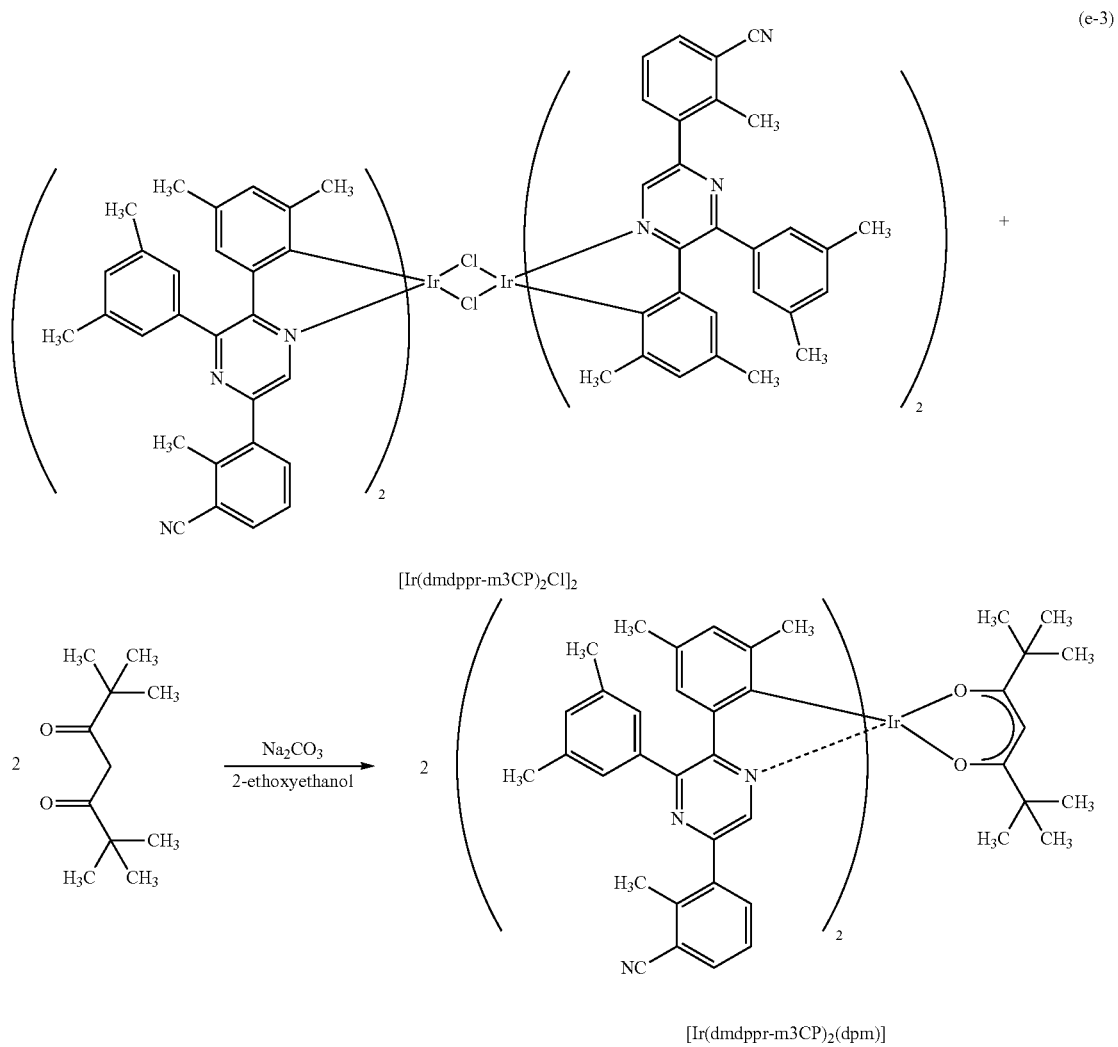

Figure 65:
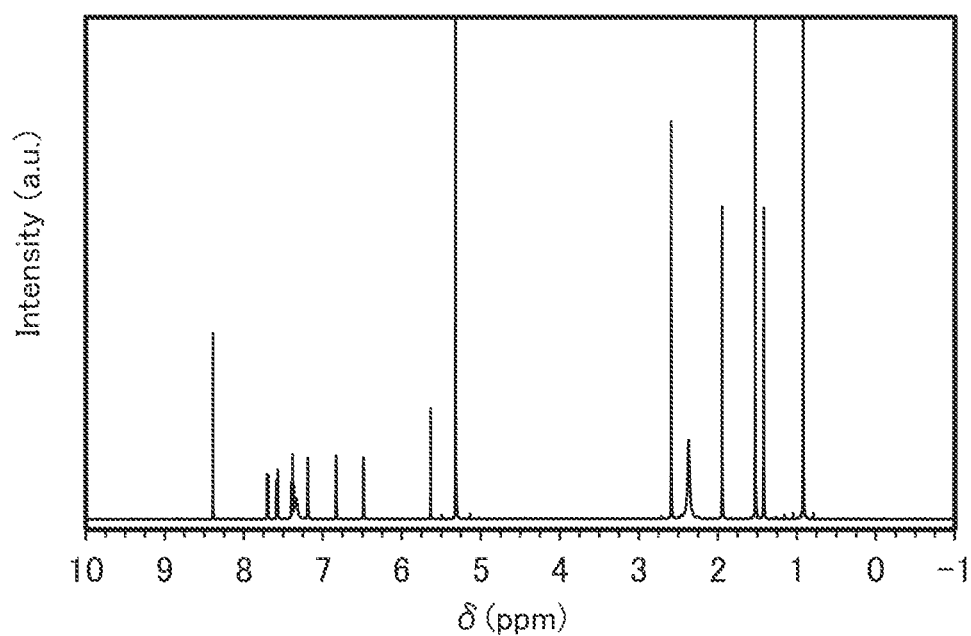
FIG. 65 is the $^1$H-NMR chart of an organic compound [Ir(dmdppr-m3CP)$_2$(dpm)].

Note that results of the analysis of the dark red solid obtained in Step 3 by nuclear magnetic resonance spectrometry ($^1$H-NMR) are shown below. The $^1$H-NMR chart is shown in FIG. 65. These results reveal that [Ir(dmdppr-m3CP)$_2$(dpm)], the organometallic complex represented by Structural Formula (100), was obtained.

$^1$H-NMR. δ (CD$_2$Cl$_2$): 0.92 (s, 18H), 1.42 (s, 6H), 1.95 (s, 6H), 2.37 (s, 12H), 2.59 (s, 6H), 5.64 (s, 1H), 6.49 (s, 2H), 6.83 (s, 2H), 7.19 (s, 2H), 7.34-7.40 (m, 6H), 7.58 (d, 2H), 7.70 (d, 2H), 8.39 (s, 2H).

EXPLANATION OF REFERENCE

101: first electrode, 102: second electrode, 103: EL layer, 103a, 103b: EL layer, 104: charge generation layer, 111, 111a, 111b: hole-injection layer, 112, 112a, 112b: hole-transport layer, 113, 113a, 113b: light-emitting layer, 114, 114a, 114b: electron-transport layer, 115, 115a, 115b: electron-injection layer, 200R, 200G, 200B: optical distance, 201: first substrate, 202: transistor (FET), 203R, 203G, 203B, 203W: light-emitting device, 204: EL layer, 205: second substrate, 206R, 206G, 206B: color filter, 206R', 206G', 206B': color filter, 207: first electrode, 208: second electrode, 209: black layer (black matrix), 210R, 210G: conductive layer, 301: first substrate, 302: pixel portion, 303: driver circuit portion (source line driver circuit), 304a, 304b: driver circuit portion (gate line driver circuit), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting device, 318: space, 900: substrate, 901: first electrode, 902: EL layer, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting device, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4200: lighting device, 4201: substrate, 4202: light-emitting device, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 5101: light, 5102: wheel cover, 5103: door, 5104: display portion, 5105: steering wheel, 5106: gear lever, 5107: seat, 5108: inner rearview mirror, 5109: windshield, 7000: housing, 7001: display portion, 7002: second display portion, 7003: speaker, 7004: LED lamp, 7005: operation key, 7006: connection terminal, 7007: sensor, 7008: microphone, 7009: switch, 7010: infrared port, 7011: recording medium reading portion, 7014: antenna, 7015: shutter button, 7016: image receiving portion, 7022, 7023: operation button, 7024: connection terminal, 7025: band, 7026: microphone, 7029: sensor, 7030: speaker, 7050: icon, 7051, 7052, 7053, 7054: information, 7111: remote controller, 9310: portable information terminal, 9311: display portion, 9312: display region, 9313: hinge, 9315: housing This application is based on Japanese Patent Application Serial No. 2018-172929 filed with Japan Patent Office on Sep. 14, 2018, the entire contents of which are hereby incorporated by reference.

The invention claimed is:

1. A light-emitting device comprising:
an EL layer between a pair of electrodes,
wherein the EL layer includes a light-emitting layer,
wherein the light-emitting layer contains a first organic compound, a second organic compound, and a light-emitting substance,
wherein a T1 level ($T_{D(edge)}$) and a T1 level ($T_{H(edge)}$) satisfy Formula (1):

$$0.07 \text{ eV} \leq T_{H(edge)} - T_{D(edge)} \leq 0.27 \text{ eV} \quad (1),$$

wherein a difference between an S1 level ($S'_{H(edge)}$) and the T1 level ($T_{H(edge)}$) satisfies Formula (2):

$$0.2 \text{ eV} \leq S'_{H(edge)} - T_{H(edge)} \leq 0.5 \text{ eV} \quad (2)$$

wherein the T1 level ($T_{H(edge)}$) represents the lower of T1 levels derived from emission edges on a short wavelength side of phosphorescent spectra of the first organic compound and the second organic compound,
wherein the T1 level ($T_{D(edge)}$) represents a T1 level derived from an absorption edge of an absorption spectrum of the light-emitting substance, and
wherein the S1 level ($S'_{H(edge)}$) represents an S1 level derived from an emission edge on a short wavelength side of a fluorescent spectrum of a mixed material of the first organic compound and the second organic compound.

2. A light-emitting device comprising:
an EL layer between a pair of electrodes,
wherein the EL layer includes a light-emitting layer,
wherein the light-emitting layer contains a first organic compound, a second organic compound, and a light-emitting substance,
wherein a T1 level ($T_{D(edge)}$) and a T1 level ($T_{H(edge)}$) satisfy Formula (3):

$$0.07 \text{ eV} \leq T_{H(edge)} - T_{D(edge)} \leq 0.17 \text{ eV} \quad (3)$$

wherein a difference between an S1 level ($S'_{H(edge)}$) and the T1 level ($T_{H(edge)}$) satisfies Formula (4):

$$0.2 \text{ eV} \leq S'_{H(edge)} - T_{H(edge)} \leq 0.5 \text{ eV} \quad (4)$$

wherein the T1 level ($T_{H(edge)}$) represents the lower of T1 levels derived from emission edges on a short wavelength side of phosphorescent spectra of the first organic compound and the second organic compound,
wherein the T1 level ($T_{D(edge)}$) represents a T1 level derived from an absorption edge of an absorption spectrum of the light-emitting substance, and
wherein the S1 level ($S'_{H(edge)}$) represents an S1 level derived from an emission edge on a short wavelength side of a fluorescent spectrum of a mixed material of the first organic compound and the second organic compound.

3. The light-emitting device according to claim 1,
wherein the first organic compound and the second organic compound form an exciplex in combination, and
wherein the S1 level ($S'_{H(edge)}$) is derived from an emission edge on a short wavelength side of a fluorescent spectrum of the exciplex.

4. The light-emitting device according to claim 1, wherein the first organic compound is a π-electron deficient heteroaromatic compound.

5. The light-emitting device according to claim 1,
wherein the first organic compound has a pyridine ring structure, a diazine ring structure, or a triazine ring structure.

6. The light-emitting device according to claim 1,
wherein the first organic compound has a structure where an aromatic ring is fused to a furan ring of a furodiazine skeleton.

7. The light-emitting device according to claim 1,
wherein the light-emitting substance is a phosphorescent substance.

8. The light-emitting device according to claim 1,
wherein the second organic compound is a carbazole derivative.

9. The light-emitting device according to claim 8,
wherein the carbazole derivative is a bicarbazole derivative.

10. The light-emitting device according to claim 8,
wherein the carbazole derivative is a 3,3'-bicarbazole derivative.

11. A light-emitting apparatus comprising:
the light-emitting device according to claim 1; and
an FPC.

12. An electronic device comprising:
the light-emitting apparatus according to claim 11; and
at least one of a microphone, a camera, an operation button, an external connection portion, and a speaker.

13. A lighting device comprising:
the light-emitting device according to claim 1; and
at least one of a housing and a cover.

14. The light-emitting device according to claim 2,
wherein the first organic compound and the second organic compound form an exciplex in combination, and
wherein the S1 level ($S'_{H(edge)}$) is derived from an emission edge on a short wavelength side of a fluorescent spectrum of the exciplex.

15. The light-emitting device according to claim 2, wherein the first organic compound is a π-electron deficient heteroaromatic compound.

16. The light-emitting device according to claim 2,
wherein the first organic compound has a pyridine ring structure, a diazine ring structure, or a triazine ring structure.

17. The light-emitting device according to claim 2,
wherein the first organic compound has a structure where an aromatic ring is fused to a furan ring of a furodiazine skeleton.

18. The light-emitting device according to claim 2,
wherein the light-emitting substance is a phosphorescent substance.

19. The light-emitting device according to claim 2, wherein the second organic compound is a carbazole derivative.

20. The light-emitting device according to claim 19, wherein the carbazole derivative is a bicarbazole derivative.

21. The light-emitting device according to claim 19, wherein the carbazole derivative is a 3,3'-bicarbazole derivative.

* * * * *